US008772285B2

(12) United States Patent
Dorwald et al.

(10) Patent No.: US 8,772,285 B2
(45) Date of Patent: Jul. 8, 2014

(54) BENZOTHIAZOLES HAVING HISTAMINE H3 RECEPTOR ACTIVITY

(71) Applicants: Florencio Zaragoza Dorwald, Visp (CH); Inge Thoger Christensen, Lyngby (DK)

(72) Inventors: Florencio Zaragoza Dorwald, Visp (CH); Rolf Hohlweg, Humlebaek (DK); Inge Thoger Christensen, Lyngby (DK); Jane Marie Lundbeck, Glostrup (DK); Knud Erik Andersen, Brondby (DK)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

(21) Appl. No.: 13/660,045

(22) Filed: Oct. 25, 2012

(65) Prior Publication Data

US 2013/0079340 A1 Mar. 28, 2013

Related U.S. Application Data

(66) Division of application No. 12/294,756, Substitute for application No. PCT/EP2007/052751, filed on Mar. 22, 2007, now Pat. No. 8,394,842.

(60) Provisional application No. 60/787,478, filed on Mar. 30, 2006, provisional application No. 60/794,288, filed on Apr. 21, 2006, provisional application No. 60/903,503, filed on Feb. 26, 2007.

(30) Foreign Application Priority Data

Mar. 28, 2006 (EP) ..................................... 06111820
Apr. 10, 2006 (EP) ..................................... 06112425
Dec. 24, 2006 (EP) ..................................... 06026875

(51) Int. Cl.
*A61K 31/535* (2006.01)
*A61K 31/497* (2006.01)
*C07D 417/00* (2006.01)
*C07D 413/00* (2006.01)
*C07D 419/00* (2006.01)

(52) U.S. Cl.
USPC .................. 514/233.8; 514/254.08; 544/135; 544/368

(58) Field of Classification Search
CPC .............................. A61K 31/496; C07D 277/62
USPC .................. 514/233.8, 254.08; 544/135, 368
See application file for complete search history.

(56) References Cited

U.S. PATENT DOCUMENTS

| 6,130,217 A | 10/2000 | Arnold et al. |
| 2003/0073672 A1 | 4/2003 | Breitenbucher et al. |
| 2005/0059663 A1 | 3/2005 | Martin et al. |

FOREIGN PATENT DOCUMENTS

| DE | 2825407 A1 | 12/1978 |
| DE | 0621271 A1 | 10/1994 |
| EP | 0196005 A1 | 10/1986 |
| EP | 0295656 A1 | 12/1988 |
| EP | 0806419 A1 | 11/1997 |
| EP | 0927992 A1 | 7/1999 |
| EP | 1134220 A1 | 9/2001 |
| JP | 02-306916 A2 | 12/1990 |
| JP | 04-316565 A2 | 11/1992 |
| JP | 11-199573 A2 | 7/1999 |
| WO | WO 94/22846 A1 | 10/1994 |
| WO | WO 99/21845 A2 | 5/1999 |
| WO | WO 00/29409 A1 | 5/2000 |
| WO | WO 01/58897 A1 | 8/2001 |
| WO | WO 01/74773 A2 | 10/2001 |
| WO | WO 01/74810 A2 | 10/2001 |
| WO | WO 02/14271 A1 | 2/2002 |
| WO | WO 03/066604 A2 | 8/2003 |
| WO | WO 2004/101559 A1 | 11/2004 |
| WO | WO 2005/082089 A2 | 9/2005 |
| WO | WO 2005/116032 A2 | 12/2005 |
| WO | WO 2007/038367 A1 | 4/2007 |

OTHER PUBLICATIONS

Celanire et al.: "Keynote review: Histamine H3 receptor antagonists reach out for the clinic," Drug Discovery Today, vol. 10, No. 23/24, Dec. 2005, pp. 1613-1627.
Chemical Abstracts Service Registry. Reg. No. 496872-68-5, Mar. 4, 2003.
European Search Report, EP 06026875.2, Jul. 4, 2007.
European Search Report, EP 06111820.4, Sep. 18, 2006.
European Search Report, EP 06112425.1, Nov. 24, 2006.
Ganellin et al., "Synthesis of Potent Non-imidazole Histamine H3-Receptor Antagonists," Arch. Pharm. Pharm. Med. Chem., vol. 331, pp. 395-404 (1998).
Hancock, "The challenge of drug discovery of a GPCR target: Analysis of preclinical pharmacology of histamine H3 antogonists/inverse agonists," Biochemical Pharmacology, vol. 71, pp. 1103-1113 (2006).
Haugwitz et al., "Antiparasitic Agents. 5. Synthesis and Anthelmintic Activities of Novel 2-Heteroaromatic-Substituted Isothiocyanatobenzoxazoles and Benzothiazoles," J. Med. Chem., vol. 25, No. 8, pp. 969-974 (1982).
International Search Report and Written Opinion of the ISR, PCT/EP2007/052751, Jun. 27, 2007.

(Continued)

*Primary Examiner* — Sarah Pihonak
(74) *Attorney, Agent, or Firm* — Samuel B. Rollins

(57) ABSTRACT

Certain novel benzothiazoles and benzoxazoles, e.g., 2-(piperazin-1-yl)benzothiazoles and 2-(piperazin-1-yl)benzoxazoles, optionally substituted in the 3 and/or 4 positions of the piperazine rings, having histamine H3 antagonistic activity can be used in pharmaceutical compositions.

12 Claims, No Drawings

(56) References Cited

OTHER PUBLICATIONS

Kitbunnadaj et al., "Synthesis and Structure-Activity Relationships of Conformationally Constrained Histamine H3 Receptor Agonists," J. Med. Chem., vol. 46, No. 25, pp. 5445-5457 (2003).

Leurs et al., "The Histamine H3 Receptor: from Gene Cloning to H3 Receptor Drugs," Nature Reviews/Drug Discovery, vol. 4, pp. 107-120 (2005).

Leurs et al., "The medicinal chemistry and therapeutic potentials of ligands of the histamine H3 receptor," Progress in Drug Research, vol. 45, pp. 107-165 (1995).

Leurs et al., "Therapeutic potential of histamine H3 receptor agonists and antagonists," Trends in Pharmacological Sciences, vol. 19, No. 5, pp. 177-183 (1998).

Linney, et al., Design, Synthesis, and Structure-Activity Relationships of Novel Non-Imidazole Histamine H3 Receptor Antagonists, Journal of Medicinal Chemistry, vol. 43, No. 12, pp. 2362-2370 (2000).

Lovenberg et al., "Cloning and Functional Expression of the Human Histamine H3 Receptor," Molecular Pharmacology, vol. 55, pp. 1101-1107 (1999).

Mackins et al., "Therapeutic potential of H3-receptor agonists in myocardial infarction," Expert Opinion on Investigational Drugs, vol. 9, No. 11, pp. 2537-2542 (2000).

Malmlof et al., "Targeting of the Central Histaminergic System for Treatment of Obesity and Associated Metabolic Disorders," Drug Development Research, vol. 67, pp. 651-665 (2006).

McLeod et al., "Sch 50971, an Orally Active Histamine H3 Receptor Agonist, Inhibits Central Neurogenic Vascular Inflammation and Produces Sedation in the Guinea Pig," J. Pharmacol. Exp. Ther., vol. 287, No. 1, pp. 43-50 (1998).

Morisset et al., "High constitutive activity of native H3 receptors regulates histamine neurons in brain," Nature, vol. 408, pp. 860-864 (2000).

Sato et al.: "Benzoxazole Derivatives as Novel 5-HT3 Receptor Partial Agonists in the Gut," Journal of Medicinal Chemistry, vol. 41, No. 16, 1998, pp. 3015-3021.

Stark et al., "Developments of histamine H3-receptor antagonists," Drugs of the Future, vol. 21, No. 5, pp. 507-520 (1996).

Tafesse et al., "Synthesis and evaluation of pyridazinylpiperazines as vanilloid receptor 1 antagonists," Bioorganic & Medicinal Chemistry Letters, vol. 14, pp. 5513-5519 (2004).

Tozer et al., "Histamine H3 receptor antagonists," Expert Opinion on Therapeutic Patents, vol. 10, No. 7, pp. 1045-1055 (2000).

Verderame, "1,4-Disubstituted Piperazines. 3 Piperazinylbenzothiazoles," Journal of Medicinal Chemistry, 15(6):693-694 (1972).

Walczynski et al., "Non-Imidazole Histamine H3 Ligands, Part 2: New 2-Substituted Benzothiazoles as Histamine H3 Antagonists," Arch. Pharm. Pharm. Med. Chem., vol. 332, No. 11, 1999, pp. 389-398.

Walczynski et al., "Non-imidazole histamine H3 ligands. Part I. Synthesis of 2-(1-piperazinyl)- and 2-(hexahydro-1H-1,4-diazepin-1-yl)benzothiazole derivatives as H3-antagonists with H1 blocking activities," Il Farmaco, vol. 54, 1999, pp. 684-694.

Walczynski et al., "Non-imidazole histamine H3 ligands. Part III. New 4-n-propylpiperazines as non-imidazole histamine H3-antagonists," European Journal of Medicinal Chemistry, vol. 40, 2005, pp. 15-23.

Yamada et al.: "A New 5-HT3 Receptor Ligand. II. Structure-Activity Analysis of 5-HT3 Receptor Agonist Action in the Gut," Chemical and Pharmaceutical Bulletin, vol. 46, No. 3, 1998, pp. 445-451.

Yoshida et al.: "Orally Active Benzoxazole Derivative as 5-HT3 Receptor Partial Agonist for Treatment of Diarrhea-Predominant Irritable Bowel Syndrome," Journal of Medicinal Chemistry, 48, No. 22, 2005, pp. 7075-7079.

Zaragoza et al., "2-(4-Alkylpiperazin-1-yl)quinolines as a New Class of Imidazole-Free Histamine H3 Receptor Antagonists," Journal of Medicinal Chemistry, 48(1):306-311 (2005).

BENZOTHIAZOLES HAVING HISTAMINE H3 RECEPTOR ACTIVITY

FIELD OF THIS INVENTION

The present invention relates to novel benzothiazoles and benzoxazoles having histamine H3 antagonistic activity, to the use of these compounds in pharmaceutical compositions, to pharmaceutical compositions comprising the compounds, and to methods of treatment employing these compounds or compositions. The present compounds show a high and selective binding affinity for the histamine H3 receptor, indicating histamine H3 receptor antagonistic, inverse agonistic or agonistic activity. As a result, the compounds are useful for the treatment of diseases or disorders related to the histamine H3 receptor.

BACKGROUND OF THIS INVENTION

The existence of the histamine H3 receptor has been known for several years and the receptor is of current interest for the development of new medicaments (see, e.g., *Drugs Fut.* 1996; 21: 507-20; *Progress in Drug Research* 1995; 45: 107-65). Recently, the human histamine H3 receptor has been cloned, cf. *Molecular Pharmacology*, 1999; 55: 1101-7. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (i.e., it is active in the absence of an agonist; see, e.g., *Nature* 2000; 408: 860-4). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Several publications disclose the preparation and use of histamine H3 agonists and antagonists. Some of these are imidazole derivatives (see, e.g., *Drugs Fut* 1996; 21: 507-20; *Expert Opinion on Therapeutic Patents* 2000; 10: 1045-55). However, a variety of imidazole-free ligands of the histamine H3 receptor is also described (see, e.g., *Arch Pharm Pharm Med Chem* 1999; 332: 389-98; *J Med Chem* 2000; 43: 2362-70; *Arch Pharm Pharm Med Chem* 1998; 331: 395-404; *Il Farmaco* 1999; 54: 684-94; WO 99/42458, EP 0 978 512, WO 97/17345, U.S. Pat. No. 6,316,475, WO 01/66534, WO 01/74810, WO 01/44191, WO 01/74815, WO 01/74773, WO 01/74813, WO 01/74814 and WO 02/12190). The state of the art is also reviewed in *Drug Discovery Today*, 2005; 10: 1613-17 and *Nat Rev Drug Discov* 2005; 4: 107. In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of substituted benzothiazoles and benzoxazoles has a high and specific affinity to and potency at the histamine H3 receptor.

Due to their interaction with the histamine H3 receptor, the present compounds are useful in the treatment of a wide range of conditions and disorders in which an interaction with the histamine H3 receptor is beneficial. Thus, the compounds may find use, e.g., in the treatment of diseases of the central nervous system, the peripheral nervous system, the cardiovascular system, the pulmonary system, the gastrointestinal system and the endo-crinological system.

In U.S. Pat. No. 6,130,217, column 120, example 85, the intermediate 2-(4-methylpiperazin-1-yl)benzothiazol-7-ol is mentioned. No pharmacological properties are mentioned for this compound.

In JP 11199573, the following compounds are mentioned: 2-(piperazin-1-yl)-6-chlorobenzothiazole fumarate; 2-(piperazin-1-yl)-5-chlorobenzothiazole fumarate; 2-(4-methylpiperazin-1-yl)-5-methylbenzothiazole fumarate; 2-(piperazin-1-yl)-5-methylbenzo-thiazole fumarate; 2-(4-methylpiperazin-1-yl)-6-chlorobenzothiazole fumarate and 2-(4-methylpiperazin-1-yl)-5-chlorobenzothiazole dihydrochloride.

In JP 2869561, the following compounds are mentioned: 2-(piperazin-1-yl)-6-chloro-benzothiazole and 2-(piperazin-1-yl)-6-(o-chlorobenzylamino)benzothiazole hydrochloride. It is stated that the compounds are platelet adhesion inhibitors.

In JP 4316565, the following intermediates are mentioned: 2-(4-methylpiperazin-1-yl)-6-methoxybenzothiazole and 2-(4-methylpiperazin-1-yl)-6-hydroxybenzothiazole. No pharmacological properties are mentioned for these compounds.

The object of this invention is to overcome or ameliorate at least one of the disadvantages of the prior art, or to provide a useful alternative.

DEFINITIONS

In the structural formulae given herein and throughout the present specification, the following terms have the indicated meaning:

The term "hydroxy" shall mean the radical —OH, the term "oxy" shall mean the radical —O—, the term "oxo" shall mean the radical =O, the term "carbonyl" shall mean the radical —C(=O)—, the term "sulfinyl" shall mean the radical —S(=O)—, the term "sulfonyl" shall mean the radical —S(=O)$_2$—, the term "carboxy" shall mean the radical —(C=O)O— and —C(=O)OH, the term "amino" shall mean the radical —NH$_2$, the term "nitro" shall mean the radical —NO$_2$ and the term "cyano" shall mean the radical —CN.

The term "C$_{2-6}$-alkenyl" as used herein represents a branched or straight hydrocarbon group having from 2 to 6 carbon atoms and at least one double bond, e.g., C$_{2-6}$-alkenyl, C$_{3-6}$-alkenyl, and the like. Representative examples are ethenyl (or vinyl), propenyl (e.g., prop-1-enyl and prop-2-enyl), butadienyl (e.g., buta-1,3-dienyl), butenyl (e.g., but-1-en-1-yl and but-2-en-1-yl), pentenyl (e.g., pent-1-en-1-yl and pent-2-en-2-yl), hexenyl (e.g., hex-1-en-2-yl and hex-2-en-1-yl), 1-ethylprop-2-enyl, 1,1-(dimethyl)prop-2-enyl, 1-ethylbut-3-enyl, 1,1-(dimethyl)but-2-enyl, and the like.

The term "C$_{1-6}$-alkoxy" as used herein refers to the radical C$_{1-6}$-alkyl-O—. Representative examples are methoxy, ethoxy, propoxy (e.g., 1-propoxy and 2-propoxy), butoxy (e.g., 1-butoxy, 2-butoxy and 2-methyl-2-propoxy), pentoxy (1-pentoxy and 2-pentoxy), hexoxy (1-hexoxy and 3-hexoxy), and the like.

The term "$C_{1-6}$-alkoxy-$C_{1-6}$-alkyl" as used herein refers to $C_{1-6}$-alkyl substituted with $C_{1-6}$-alkoxy at any carbon atom. Representative examples are methoxymethyl, ethoxymethyl, 2-methoxyethyl, 2-ethoxyethyl, 3-methoxyprop-1-yl, and the like.

The term "$C_{1-6}$-alkoxycarbonyl" as used herein refers to the radical $C_{1-6}$-alkoxy-C(=O)—. Representative examples are methoxycarbonyl, ethoxycarbonyl, 1-propoxycarbonyl, 2-propoxycarbonyl, 1-butoxycarbonyl, 2-butoxycarbonyl, 2-methyl-2-propoxycarbonyl, 3-methylbutoxycarbonyl, 1-hexoxycarbonyl, and the like.

The term "$C_{1-6}$-alkyl" as used herein represents a saturated, branched or straight hydrocarbon group having from 1 to 6 carbon atoms, e.g., $C_{1-3}$-alkyl, $C_{1-4}$-alkyl, $C_{2-6}$-alkyl, $C_{3-6}$-alkyl, and the like. Representative examples are methyl, ethyl, propyl (e.g., prop-1-yl and prop-2-yl (or isopropyl)), butyl (e.g., 2-methylprop-2-yl (or tert-butyl), but-1-yl and but-2-yl), pentyl (e.g., pent-1-yl, pent-2-yl and pent-3-yl), 2-methylbut-1-yl, 3-methylbut-1-yl, hexyl (e.g., hex-1-yl), heptyl (e.g., hept-1-yl) and the like.

Analogously, the term "$C_{1-3}$-alkyl" as used herein represents a saturated, branched or straight hydrocarbon group having from 1 to 3 carbon atoms. Representative examples are methyl, ethyl, propyl (e.g., prop-1-yl and prop-2-yl (or isopropyl)) and the like.

The term "$C_{1-6}$-alkylcarbonyl" as used herein refers to the radical $C_{1-6}$-alkyl-C(=O)—. Representative examples are acetyl (e.g., methylcarbonyl), propionyl (e.g., ethylcarbonyl), butanoyl (e.g., prop-1-ylcarbonyl and prop-2-ylcarbonyl), and the like.

The term "$C_{1-6}$-alkylcarbonylamino" as used herein, refers to the radical $C_{1-6}$-alkyl-C(=O)—NH—. Representative examples are acetylamino, propionylamino, pivaloylamino, valeroylamino, and the like.

The term "$C_{1-6}$-alkylcarbonylamino-$C_{1-6}$-alkyl" as used herein, refers to $C_{1-6}$-alkyl substituted at any carbon atom with $C_{1-6}$-alkylcarbonylamino. Representative examples are acetylaminomethyl, 1-(acetylamino)ethyl, propionylaminomethyl, and the like.

The term "$C_{1-6}$-alkylcarboxy" as used herein refers to the radical $C_{1-6}$-alkyl-C(=O)O—. Representative examples are methylcarboxy, ethylcarboxy, propylcarboxy (e.g., prop-1-ylcarboxy, prop-2-ylcarboxy), and the like.

The term "$C_{1-6}$-alkylene" as used herein refers a branched or straight hydrocarbon group having from 1 to 6 carbon atoms and two free bonds. Representative examples are methylene, ethylene, propylenes, e.g., 1,3-propylene, and butylenes, e.g., 1,4-butylene (1,4-butanediyl), and the like.

Analogously, the term "$C_{1-4}$-alkylene" refers a branched or straight hydrocarbon group having from 1 to 4 carbon atoms and two free bonds.

The term "$C_{1-6}$-alkylsulfanyl" as used herein refers to the radical $C_{1-6}$-alkyl-S—. Representative examples are methylthio, ethylthio, propylthio (e.g., 1-propylthio, 2-propylthio and 3-propylthio), butylthio, pentylthio, hexylthio, and the like.

The term "$C_{1-6}$-alkylsulfinyl" as used herein refers to the radical $C_{1-6}$-alkyl-S(=O)—.

Representative examples are methylsulfinyl, ethylsulfinyl, propylsulfinyl, butylsulfinyl, pentylsulfinyl, hexylsulfinyl, and the like.

The term "$C_{1-6}$-alkylsulfonyl" as used herein refers to the radical $C_{1-6}$-alkyl-S(=O)$_2$—. Representative examples are methylsulfonyl, ethylsulfonyl, propylsulfonyl, butylsulfonyl, pentylsulfonyl, hexylsulfonyl, and the like.

The term "$C_{2-8}$-alkynyl" as used herein represents a branched or straight hydrocarbon group having from 2 to 8 carbon atoms and at least one triple bond. Representative examples are ethynyl, propynyl (e.g., prop-1-ynyl and prop-2-ynyl), butynyl (e.g., but-1-ynyl and but-2-ynyl), pentynyl (e.g., pent-1-ynyl and pent-2-ynyl), hexynyl (e.g., hex-1-ynyl and hex-2-ynyl), 1-ethylprop-2-ynyl, 1,1-(dimethyl)prop-2-ynyl, 1-ethylbut-3-ynyl, 1,1-(dimethyl)but-2-ynyl, and the like.

The term "aryl" as used herein is intended to include monocyclic, bicyclic or polycyclic carbocyclic aromatic rings. Representative examples are phenyl, naphthyl (e.g., naphth-1-yl and naphth-2-yl), anthryl (e.g., anthr-1-yl and anthr-9-yl), phenanthryl (e.g., phenanthr-1-yl and phenanthr-9-yl), and the like. Aryl is also intended to include monocyclic, bicyclic or polycyclic carbocyclic aromatic rings substituted with carbocyclic aromatic rings. Representative examples are biphenyl (e.g., biphenyl-2-yl, biphenyl-3-yl and biphenyl-4-yl), phenylnaphthyl (e.g. 1-phenylnaphth-2-yl and 2-phenylnaphth-1-yl), and the like. Aryl is also intended to include partially saturated bicyclic or polycyclic carbocyclic rings with at least one unsaturated moiety (e.g., a benzo moiety). Representative examples are, indanyl (e.g., indan-1-yl, indan-5-yl), indenyl (e.g., inden-1-yl and inden-5-yl), 1,2,3,4-tetrahydronaphthyl (e.g., 1,2,3,4-tetrahydronaphth-1-yl, 1,2,3,4-tetrahydronaphth-2-yl and 1,2,3,4-tetrahydronaphth-6-yl), 1,2-dihydronaphthyl (e.g., 1,2-dihydronaphth-1-yl, 1,2-dihydronaphth-4-yl and 1,2-dihydronaphth-6-yl), fluorenyl (e.g., fluoren-1-yl, fluoren-4-yl and fluoren-9-yl), and the like. Aryl is also intended to include partially saturated bicyclic or polycyclic carbocyclic aromatic rings containing one or two bridges. Representative examples are, benzonorbornyl (e.g., benzonorborn-3-yl and benzonorborn-6-yl), 1,4-ethano-1,2,3,4-tetrahydronapthyl (e.g., 1,4-ethano-1,2,3,4-tetrahydronapth-2-yl and 1,4-ethano-1,2,3,4-tetrahydronapth-10-yl), and the like. Aryl is also intended to include partially saturated bicyclic or polycyclic carbocyclic aromatic rings containing one or more spiro atoms. Representative examples are spiro-[cyclopentane-1,1'-indane]-4-yl, spiro[cyclopentane-1,1'-indene]-4-yl, spiro[piperidine-4,1'-indane]-1-yl, spiro[piperidine-3,2'-indane]-1-yl, spiro [piperidine-4,2'-indane]-1-yl, spiro-[piperidine-4,1'-indane]-3'-yl, spiro[pyrrolidine-3,2'-indane]-1-yl, spiro[pyrrolidine-3,1'-(3',4'-dihydronaphthalene)]-1-yl, spiro[piperidine-3,1'-(3',4'-dihydronaphthalene)]-1-yl, spiro-[piperidine-4,1'-(3', 4'-dihydronaphthalene)]-1-yl, spiro[imidazolidine-4,2'-indane]-1-yl, spiro-[piperidine-4,1'-indene]-1-yl, and the like.

The term "arylcarbonyl" as used herein refers to the radical aryl-C(=O)—. Representative examples are benzoyl, naphthylcarbonyl, 4-phenylbenzoyl, anthrylcarbonyl, phenanthrylcarbonyl, and the like.

The term "arylcarbonylamino" as used herein, refers to the radical aryl-C(=O)—NH—. Representative examples are benzoylamino, naphthylcarbonylamino, 4-phenylbenzoylamino, and the like.

The term "arylcarbonylamino-$C_{1-6}$-alkyl" as used herein, refers to $C_{1-6}$-alkyl substituted at any carbon atom with arylcarbonylamino. Representative examples are benzoylaminomethyl, naphthylcarbonylaminomethyl, 2-(4-phenylbenzoylamino)ethyl, and the like.

The term "cyano-$C_{1-6}$-alkyl" as used herein refers to $C_{1-6}$-alkyl, substituted at any carbon atom(s) with cyano. Representative examples are cyanomethyl, 2-cyanoethyl, and the like.

The term "C$_{5-8}$-cycloalkenyl" as used herein represents a partially saturated monocyclic carbocyclic ring having from 5 to 8 carbon atoms and at least one double bond. Representative examples are cyclopentenyl, cyclohexenyl, cycloheptenyl, cyclooctenyl, cyclohex-1,3-dienyl, and the like.

Obviously, the term "C$_{5-8}$-cycloalkenyl-C$_{2-6}$-alkenyl" is a combination of C$_{5-8}$-cycloalkenyl and C$_{2-6}$-alkenyl as defined herein.

Obviously, the term "C$_{5-8}$-cycloalkenyl-C$_{1-6}$-alkyl" is a combination of C$_{5-8}$-cycloalkenyl and C$_{1-6}$-alkyl as defined herein.

Obviously, the term "C$_{5-8}$-cycloalkenyl-C$_{2-6}$-alkynyl" is a combination of C$_{5-8}$-cycloalkenyl and C$_{2-6}$-alkynyl as defined herein.

The term "C$_{3-8}$-cycloalkyl" as used herein represents a saturated monocyclic carbocyclic ring having from 3 to 8 carbon atoms, e.g., C$_{3-6}$-alkyl, and the like. Representative examples are cyclopropyl, cyclobutyl, cyclopentyl, cyclohexyl, cycloheptyl, cyclooctyl, and the like. C$_{3-8}$-cycloalkyl is also intended to represent a saturated bicyclic carbocyclic ring having from 4 to 8 carbon atoms. Representative examples are decahydronaphthalenyl, bicycle[3.3.0]octanyl, and the like. C$_{3-8}$-cycloalkyl is also intended to represent a saturated carbocyclic ring having from 3 to 8 carbon atoms and containing one or two carbon bridges. Representative examples are adamantyl, norbornanyl, nortricyclyl, bicyclo[3.2.1]octanyl, bicyclo[2.2.2]octanyl, tricyclo[5.2.1.0/2,6]decanyl, bicyclo[2.2.1]heptyl, and the like. C$_{3-8}$-cycloalkyl is also intended to represent a saturated carbocyclic ring having from 3 to 8 carbon atoms and containing one or more spiro atoms. Representative examples are spiro[2.5]octanyl, spiro[4.5]decanyl, and the like.

Obviously, the term "C$_{3-8}$-cycloalkyl-C$_{2-6}$-alkenyl" is a combination of C$_{3-8}$-cycloalkyl and C$_{2-6}$-alkenyl as defined herein.

Obviously, the term "C$_{3-8}$-cycloalkyl-C$_{1-6}$-alkyl" is a combination of C$_{1-6}$-cycloalkyl and C$_{1-6}$-alkyl. Representative examples are cyclopropylmethyl, 2-cyclohexylethyl, 3-cyclopentyl-prop-1-yl, 1-cyclohexylethyl, adamantylmethyl, and the like. In this substituent, the non-cyclic alkyl group preferably has not more than 3 carbon atoms.

Obviously, the term "C$_{3-8}$-cycloalkyl-C$_{2-6}$-alkynyl" is a combination of C$_{3-8}$-cycloalkyl and C$_{2-6}$-alkynyl as defined herein.

Obviously, the term "di(C$_{3-8}$-cycloalkyl)-C$_{1-6}$-alkyl" is a combination of two C$_{3-8}$-cycloalkyl groups and one C$_{1-6}$-alkyl group as defined herein.

The term "halo-C$_{1-6}$-alkyl" as used herein refers to C$_{1-6}$-alkyl, substituted one or more times at any carbon atom(s) with any halogen. Representative examples are trifluoromethyl, 2,2,2-trifluoroethyl, and the like.

The term "halo-C$_{1-6}$-alkoxy" as used herein refers to C$_{1-6}$-alkoxy, substituted one or more times at any carbon atom(s) with any halogen. Representative examples are trifluoromethoxy and 2,2,2-trifluoroethoxy, and the like.

The term "halogen" or "halo" means fluorine, chlorine, bromine or iodine.

The term "heteroaryl" as used herein is intended to include monocyclic heterocyclic aromatic rings containing one or more heteroatoms selected from nitrogen, oxygen, sulfur, SO and S(=O)$_2$. Representative examples are pyrrolyl (e.g., pyrrol-1-yl, pyrrol-2-yl and pyrrol-3-yl), furanyl (e.g., furan-2-yl and furan-3-yl), thienyl (e.g., thien-2-yl and thien-3-yl), oxazolyl (e.g., oxazol-2-yl, oxazol-4-yl and oxazol-5-yl), thiazolyl (e.g., thiazol-2-yl, thiazol-4-yl and thiazol-5-yl), imidazolyl (e.g., imidazol-2-yl, imidazol-4-yl and imidazol-5-yl), pyrazolyl (e.g., pyrazol-1-yl, pyrazol-3-yl and pyrazol-5-yl), isoxazolyl (e.g., isoxazol-3-yl, isoxazol-4-yl and isoxazol-5-yl), isothiazolyl (e.g., isothiazol-3-yl, isothiazol-4-yl and isothiazol-5-yl), 1,2,3-triazolyl (e.g., 1,2,3-triazol-1-yl, 1,2,3-triazol-4-yl and 1,2,3-triazol-5-yl), 1,2,4-triazolyl (e.g., 1,2,4-triazol-1-yl, 1,2,4-triazol-3-yl and 1,2,4-triazol-5-yl), 1,2,3-oxadiazolyl(e.g., 1,2,3-oxa-diazol-4-yl and 1,2,3-oxadiazol-5-yl), 1,2,4-oxadiazolyl(e.g., 1,2,4-oxadiazol-3-yl and 1,2,4-oxa-diazol-5-yl), 1,2,5-oxadiazolyl (e.g., 1,2,5-oxadiazol-3-yl and 1,2,5-oxadiazol-4-yl), 1,3,4-oxadi-azolyl (e.g., 1,3,4-oxadiazol-2-yl and 1,3,4-oxadiazol-5-yl), 1,2,3-thiadiazolyl(e.g., 1,2,3-thia-diazol-4-yl and 1,2,3-thiadiazol-5-yl), 1,2,4-thiadiazolyl(e.g., 1,2,4-thiadiazol-3-yl and 1,2,4-thia-diazol-5-yl), 1,2,5-thiadiazolyl (e.g., 1,2,5-thiadiazol-3-yl and 1,2,5-thiadiazol-4-yl), 1,3,4-thia-diazolyl (e.g., 1,3,4-thiadiazol-2-yl and 1,3,4-thiadiazol-5-yl), tetrazolyl (e.g., tetrazol-1-yl and tetrazol-5-yl), pyranyl (e.g., pyran-2-yl), pyridinyl (e.g., pyridine-2-yl, pyridine-3-yl and pyridine-4-yl), pyridazinyl (e.g., pyridazin-2-yl and pyridazin-3-yl), pyrimidinyl (e.g., pyrimidin-2-yl, pyrimidin-4-yl and pyrimidin-5-yl), pyrazinyl, 1,2,3-triazinyl, 1,2,4-triazinyl, 1,3,5-triazinyl, thiadiazinyl, azepinyl, azecinyl, and the like. Heteroaryl is also intended to include bicyclic heterocyclic aromatic rings containing one or more heteroatoms selected from nitrogen, oxygen, sulfur, S(=O) and S(=O)$_2$. Representative examples are indolyl (e.g., indol-1-yl, indol-2-yl, indol-3-yl and indol-5-yl), isoindolyl, benzofuranyl (e.g., benzo[b]furan-2-yl, benzo[b]furan-3-yl, benzo[b]furan-5-yl, benzo[c]furan-2-yl, benzo[c]furan-3-yl and benzo[c]furan-5-yl), benzothienyl (e.g., benzo[b]thien-2-yl, benzo[b]thien-3-yl, benzo[b]thien-5-yl, benzo[c]thien-2-yl, benzo[c]thien-3-yl and benzo[c]thien-5-yl), indazolyl (e.g., indazol-1-yl, indazol-3-yl and indazol-5-yl), indolizinyl (e.g., indolizin-1-yl and indolizin-3-yl), benzopyranyl (e.g., benzo[b]pyran-3-yl, benzo[b]pyran-6-yl, benzo[c]pyran-1-yl and benzo[c]pyran-7-yl), benzimidazolyl (e.g., benzimidazol-1-yl, benzimidazol-2-yl and benzimidazol-5-yl), benzothiazolyl (e.g., benzothiazol-2-yl and benzothiazol-5-yl), benzisothiazolyl, benzoxazolyl, benzisoxazolyl, benzoxazinyl, benzotriazolyl, naphthyridinyl (e.g., 1,8-naphthyridin-2-yl, 1,7-naphthyridin-2-yl and 1,6-naphthyridin-2-yl), phthalazinyl (e.g., phthalazin-1-yl and phthalazin-5-yl), pteridinyl, purinyl (e.g., purin-2-yl, purin-6-yl, purin-7-yl, purin-8-yl and purin-9-yl), quinazolinyl (e.g., quinazolin-2-yl, quinazolin-4-yl and quinazolin-6-yl), cinnolinyl, quinoliny (e.g., quinolin-2-yl, quinolin-3-yl, quinolin-4-yl and quinolin-6-yl), isoquinolinyl (e.g., isoquinolin-1-yl, isoquinolin-3-yl and isoquinolin-4-yl), quinoxalinyl (e.g., quinoxalin-2-yl and quinoxalin-5-yl), pyrrolopyridinyl (e.g., pyrrolo[2,3-b]pyridinyl, pyrrolo[2,3-c]pyridinyl and pyrrolo[3,2-c]pyridinyl), furopyridinyl (e.g., furo[2,3-b]pyridinyl, furo[2,3-c]pyridinyl and furo[3,2-c]pyridinyl), thienopyridinyl (e.g., thieno[2,3-b]pyridinyl, thieno[2,3-c]pyridinyl and thieno[3,2-c]pyridinyl), imidazopyridinyl (e.g., imidazo[4,5-b]pyridinyl, imidazo[4,5-c]pyridinyl, imidazo[1,5-a]pyridinyl and imidazo[1,2-a]-pyridinyl), imidazopyrimidinyl (e.g., imidazo[1,2-a]pyrimidinyl and imidazo[3,4-a]pyrimidinyl), pyrazolopyridinyl (e.g., pyrazolo[3,4-b]pyridinyl, pyrazolo[3,4-c]pyridinyl and pyrazolo[1,5-a]-pyridinyl), pyrazolopyrimidinyl (e.g., pyrazolo[1,5-a]pyrimidinyl and pyrazolo[3,4-d]-pyrimidinyl), thiazolopyridinyl (e.g., thiazolo[3,2-d]pyridinyl), thiazolopyrimidinyl (e.g., thiazolo[5,4-d]pyrimidinyl), imidazothiazolyl (e.g., imidazo[2,1-b]thiazolyl), triazolopyridinyl (e.g., triazolo[4,5-b]pyridinyl), triazolopyrimidinyl (e.g., 8-azapurinyl), and the like. Heteroaryl is also intended to include polycyclic heterocyclic aromatic rings containing one or more heteroatoms selected from nitrogen, oxygen, sulfur, S(=O) and S(=O)$_2$. Representative examples are carbazolyl (e.g., carbazol-2-yl, carbazol-3-yl, carbazol-9-yl), phenoxazinyl (e.g., phenoxazin-10-yl), phenazinyl (e.g., phenazin-5-yl), acridinyl (e.g., acridin-9-yl and acridin-10-yl), phenolthiazinyl (e.g., phenothiazin-10-yl), carbolinyl (e.g., pyrido[3,4-b]indol-1-yl, pyrido[3,4-b]indol-3-yl), phenanthrolinyl (e.g., phenanthrolin-5-yl), and the like. Heteroaryl is also intended to include partially saturated monocyclic, bicyclic or polycyclic heterocyclic rings containing one or more heteroatoms selected from nitrogen, oxygen, sulfur, $S(=O)$ and $S(=O)_2$. Representative examples are pyrrolinyl, pyrazolinyl, imidazolinyl (e.g., 4,5-dihydroimidazol-2-yl and 4,5-dihydroimidazol-1-yl), indolinyl (e.g., 2,3-dihydroindol-1-yl and 2,3-dihydroindol-5-yl), dihydrobenzofuranyl (e.g., 2,3-dihydrobenzo[b]furan-2-yl and 2,3-dihydrobenzo[b]furan-4-yl), dihydrobenzothienyl (e.g., 2,3-dihydrobenzo[b]thien-2-yl and 2,3-dihydrobenzo[b]thien-5-yl), 4,5,6,7-tetrahydrobenzo[b]furan-5-yl), dihydrobenzopyranyl (e.g., 3,4-dihydrobenzo[b]pyran-3-yl, 3,4-dihydrobenzo[b]pyran-6-yl, 3,4-dihydrobenzo[c]pyran-1-yl and dihydrobenzo[c]pyran-7-yl), 2,3-dihydrobenzo[1,4]dioxin-6-yl, 2,3-dihydrobenzo[1,4]dioxin-5-yl, 2,3-dihydrobenzo[1,4]dioxin-2-yl, benzo[1,3]dioxol-4-yl, benzo[1,3]dioxol-5-yl, benzo[1,3]dioxol-2-yl; 3,4-dihydro-2Hbenzo[1,4]oxazin-7-yl; 4-methyl-3,4-dihydro-2Hbenzo[1,4]oxazin-7-yl, oxazolinyl (e.g., 4,5-dihydrooxazol-2-yl, 4,5-dihydrooxazol-4-yl and 4,5-dihydrooxazol-5-yl), isoxazolinyl, oxazepinyl, tetrahydroindazolyl (e.g., 4,5,6,7-tetrahydroindazol-1-yl, 4,5,6,7-tetrahydroindazol-3-yl, 4,5,6,7-tetrahydroindazol-4-yl and 4,5,6,7-tetrahydroindazol-6-yl), tetrahydrobenzimidazolyl (e.g., 4,5,6,7-tetrahydrobenzimidazol-1-yl and 4,5,6,7-tetrahydrobenzimidazol-5-yl), tetrahydroimidazo[4,5-c]pyridyl (e.g., 4,5,6,7-tetrahydroimidazo[4,5-c]pyrid-1-yl, 4,5,6,7-tetrahydroimidazo[4,5-c]pyrid-5-yl and 4,5,6,7-tetrahydroimidazo[4,5-c]pyrid-6-yl), tetrahydroquinolinyl (e.g., 1,2,3,4-tetrahydroquinolinyl and 5,6,7,8-tetrahydroquinolinyl), tetrahydroisoquinolinyl (e.g., 1,2,3,4-tetrahydroisoquinolinyl and 5,6,7,8-tetrahydroi-soquinolinyl), tetrahydroquinoxalinyl (e.g., 1,2,3,4-tetrahydroquinoxalinyl and 5,6,7,8-tetrahydroquinoxalinyl), and the like. Heteroaryl is also intended to include partially saturated bicyclic or polycyclic heterocyclic rings containing one or more spiro atoms. Representative examples are spiro[isoquinoline-3,1'-cyclohexan]-1-yl, spiro[piperidine-4,1'benzo[c]thiophen]-1-yl, spiro[piperidine-4,1'benzo[c]furan]-1-yl, spiro[piperidine-4,3'benzo[b]furan]-1-yl, spiro-[piperidine-4,3'-coumarin]-1-yl, and the like.

The term "heteroarylcarbonyl" as used herein refers to the radical heteroaryl-$C(=O)-$. Representative examples are pyridinylcarbonyl (e.g., pyridin-2-ylcarbonyl and pyridin-4-yl-carbonyl), quinolinylcarbonyl (e.g., 2-(quinolin-2-yl)carbonyl and 1-(quinolin-2-yl)carbonyl), imidazolylcarbonyl (e.g., imidazol-2-ylcarbonyl and imidazol-5-ylcarbonyl), and the like.

The term "heteroarylcarbonylamino" as used herein, refers to the radical heteroaryl-$C(=O)-NH-$. Representative examples are pyridinylcarbonylamino (e.g., pyridin-2-ylcarbonyl-amino and pyridin-4-ylcarbonylamino), quinolinyl-carbonylamino (e.g., 2-(quinolin-2-yl)-carbonylamino and 1-(quinolin-2-yl)carbonylamino), and the like.

The term "heteroarylcarbonylamino-$C_{1-6}$-alkyl" as used herein, refers to $C_{1-6}$-alkyl substituted at any carbon atom with heteroarylcarbonylamino. Representative examples are pyridinylcarbonylaminomethyl (e.g., pyridin-2-ylcarbonyl-aminomethyl and pyridin-4-yl-carbonylaminomethyl), 2-(quinolinylcarbonylamino)ethyl (e.g., 2-(2-(quinolin-2-yl)carbonyl-amino)ethyl and 2-(1-(quinolin-2-yl)carbonylamino)ethyl), and the like.

The term "heterocyclyl" as used herein represents a saturated 3 to 8 membered monocyclic ring, containing one or more heteroatoms selected from nitrogen, oxygen, sulfur, $S(=O)$ and $S(=O)_2$. Representative examples are aziridinyl (e.g., aziridin-1-yl), azetidinyl (e.g., azetidin-1-yl and azetidin-3-yl), oxetanyl, pyrrolidinyl (e.g., pyrrolidin-1-yl, pyrrolidin-2-yl and pyrrolidin-3-yl), imidazolidinyl (e.g., imidazolidin-1-yl, imidazolidin-2-yl and imidazolidin-4-yl), oxazolidinyl (e.g., oxazolidin-2-yl, oxazolidin-3-yl and oxazolidin-4-yl), thiazolidinyl (e.g., thiazolidin-2-yl, thiazolidin-3-yl and thiazolidin-4-yl), isothiazolidinyl, 1,1-dioxo-isothiazolidin-2-yl, piperidinyl (e.g., piperidin-1-yl, piperidin-2-yl, piperidin-3-yl and piperidin-4-yl), homopiperidinyl (e.g., homopiperidin-1-yl, homopiperidin-2-yl, homopiperidin-3-yl and homopiperidin-4-yl), piperazinyl (e.g., piperazin-1-yl and piperazin-2-yl), morpholinyl (e.g., morpholin-2-yl, morpholin-3-yl and morpholin-4-yl), thiomorpholinyl (e.g., thiomorpholin-2-yl, thiomorpholin-3-yl and thiomorpholin-4-yl), 1-oxo-thiomorpholinyl, 1,1-dioxo-thiomorpholinyl, tetrahydrofuranyl (e.g., tetrahydrofuran-2-yl and tetrahydrofuran-3-yl), tetrahydrothienyl, tetrahydro-1,1-dioxothienyl, tetrahydropyranyl (e.g., 2-tetrahydropyranyl), tetrahydrothiopyranyl (e.g., 2-tetrahydrothiopyranyl), 1,4-dioxanyl, 1,3-dioxanyl, and the like. Heterocyclyl is also intended to represent a saturated 6 to 12 membered bicyclic ring containing one or more heteroatoms selected from nitrogen, oxygen, sulfur, $S(=O)$ and $S(=O)_2$. Representative examples are octahydroindolyl (e.g., octahydroindol-1-yl, octahydroindol-2-yl, octahydroindol-3-yl and octahydroindol-5-yl), decahydroquinolinyl (e.g., decahydroquinolin-1-yl, decahydroquinolin-2-yl, decahydroquinolin-3-yl, decahydroquinolin-4-yl and decahydroquinolin-6-yl), decahydroquinoxalinyl (e.g., decahydroquinoxalin-1-yl, decahydroquinoxalin-2-yl and decahydroquinoxalin-6-yl) and the like. Heterocyclyl is also intended to represent a saturated 6 to 12 membered ring containing one or more heteroatoms selected from nitrogen, oxygen, sulfur, $S(=O)$ and $S(=O)_2$ and having one or two bridges. Representative examples are 3-azabicyclo[3.2.2]nonyl, 2-azabicycle[2.2.1]-heptyl, 3-azabicyclo[3.1.0]hexyl, 2,5-diazabicyclo[2.2.1]heptyl, atropinyl, tropinyl, quinuclidinyl, 1,4-diazabicyclo[2.2.2]octanyl, and the like. Heterocyclyl is also intended to represent a 6 to 12 membered saturated ring containing one or more heteroatoms selected from nitrogen, oxygen, sulfur, $S(=O)$ and $S(=O)_2$ and containing one or more spiro atoms. Representative examples are 1,4-dioxaspiro[4.5]decanyl (e.g., 1,4-dioxaspiro[4.5]decan-2-yl and 1,4-dioxaspiro[4.5]decan-7-yl), 1,4-dioxa-8-azaspiro[4.5]decanyl (e.g., 1,4-dioxa-8-azaspiro[4.5]decan-2-yl and 1,4-dioxa-8-azaspiro[4.5]decan-8-yl), 8-azaspiro[4.5]decanyl (e.g., 8-azaspiro[4.5]decan-1-yl and 8-azaspiro[4.5]decan-8-yl), 2-azaspiro[5.5]undecanyl (e.g., 2-azaspiro[5.5]undecan-2-yl), 2,8-diazaspiro[4.5]decanyl (e.g., 2,8-diaza-spiro[4.5]decan-2-yl and 2,8-diazaspiro[4.5]decan-8-yl), 2,8-diazaspiro[5.5]undecanyl (e.g., 2,8-diazaspiro[5.5]undecan-2-yl), 1,3,8-triazaspiro[4.5]decanyl (e.g., 1,3,8-triazaspiro[4.5]-decan-1-yl and 1,3,8-triazaspiro[4.5]decan-3-yl, 1,3,8-triazaspiro[4.5]decan-8-yl), and the like.

The term "heterocyclyl-$C_{1-6}$-alkoxy" as used herein refers to the radical heterocyclyl-$C_{1-6}$-alkoxy. Representative examples are piperidin-1-ylmethoxy, 2-(piperidin-1-yl)ethoxy, 3-(piperidin-1-yl)prop-3-oxy, piperazin-1-ylmethoxy, 2-(piperazin-1-yl)ethoxy, 3-(piperazin-1-yl)prop- 3-oxy, morpholin-1-ylmethoxy, 2-(morpholin-1-yl)ethoxy, 3-(morpholin-1-yl)prop-3-oxy, and the like.

The term "heterocyclyl-$C_{1-6}$-alkyl" as used herein refers to the radical heterocyclyl-$C_{1-6}$-alkyl. Representative examples are piperidin-1-ylmethyl, 2-(piperidin-1-yl)ethyl, hydroxy-3-(piperidin-1-yl)propyl, piperazin-1-ylmethyl, 2-(piperazin-1-yl)ethyl, 3-hydroxy-3-(piperazin-1-yl)propyl, morpholin-1-ylmethyl, 2-(morpholin-1-yl)ethyl, 3-hydroxy-3-(morpholin-1-yl)propyl, and the like.

The term "heterocyclylcarbonyl" as used herein refers to the radical heterocyclyl-C(=O)—. Representative examples are piperidinylcarbonyl (e.g., piperidin-2-ylcarbonyl, piperidin-3-ylcarbonyl and piperidin-4-ylcarbonyl), piperazinylcarbonyl (e.g., piperazin-1-yl-carbonyl and piperazin-2-ylcarbonyl), and the like.

The term "hydroxy-$C_{1-6}$-alkyl" as used herein refers to $C_{1-6}$-alkyl substituted one or more times at any carbon atom(s) with hydroxyl. Representative examples are hydroxymethyl, hydroxyethyl (e.g., 1-hydroxyethyl and 2-hydroxyethyl), and the like.

The term "bridge" as used herein represents a connection in a saturated or partly saturated ring between two atoms of such ring that are not neighbors through a chain of 1 to 4 atoms selected from carbon, nitrogen, oxygen and sulfur. Representative examples of such connecting chains are —$CH_2$—, —$CH_2CH_2$—, —$CH_2NHCH_2$—, —$CH_2CH_2CH_2$—, —$CH_2OCH_2$—, and the like.

The term "spiro atom" as used herein represents a carbon atom in a saturated or partly saturated ring that connects both ends of a chain of 3 to 8 atoms selected from carbon, nitrogen, oxygen and sulfur. Representative examples are —$(CH_2)_5$—, —$(CH_2)_3$—, —$(CH_2)_4$—, —$CH_2NHCH_2CH_2$—, —$CH_2CH_2NHCH_2CH_2$—, —$CH_2NHCH_2CH_2CH_2$—, —$CH_2CH_2OCH_2$—, —$OCH_2CH_2O$—, and the like.

The term "optionally substituted" as used herein means that the groups in question are either unsubstituted or substituted with one or more of the substituents specified. When the group(s) in question are substituted with more than one substituent, the substituents may be the same or different.

Certain of the defined terms may occur more than once in the structural formulae, and upon such occurrence each term shall be defined independently of the other. Certain of the defined terms may occur in combinations, and it is to be understood that the first mentioned radical is a substituent on the subsequently mentioned radical, where the point of substitution, i.e. the point of attachment to another part of the molecule, is on the last mentioned of the radicals.

The term "solvate" as used herein is a complex of defined stoichiometry formed by a solute (in casu, a compound according to the present invention) and a solvent. Solvents are those commonly used in the pharmaceutical art, by way of example, water, ethanol, acetic acid, and the like. The term "hydrate" refers to the complex where the solvent molecule is water.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

The terms "disease", "condition" and "disorder" as used herein are used interchangeably to specify a state of a patient which is not the normal physiological state of man.

The term "medicament" as used herein means a pharmaceutical composition suitable for administration of the pharmaceutically active compound to a patient.

The term "prodrug" as used herein includes biohydrolyzable amides and biohydrolyzable esters and also encompasses a) compounds in which the biohydrolyzable functionality in such a prodrug is encompassed in the compound according to the present invention, and b) compounds which may be oxidized or reduced biologically at a given functional group to yield drug substances according to the present invention. Examples of these functional groups include 1,4-dihydropyridine, N-alkylcarbonyl-1,4-dihydropyridine, 1,4-cyclohexadiene, tert-butyl, and the like.

The term "biohydrolyzable ester" as used herein is an ester of a drug substance (in this invention, a compound of formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to (I) in plasma. Many examples of such are known in the art and include by way of example lower alkyl esters (e.g., $C_{1-4}$-alkyl esters), lower acyloxyalkyl esters, lower alkoxyacyloxyalkyl esters, alkoxyacyloxy esters, alkyl acylamino alkyl esters, and choline esters.

The term "biohydrolyzable amide" as used herein is an amide of a drug substance (in this invention, a compound of general formula I) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

The term "pharmaceutically acceptable" as used herein means suited for normal pharmaceutical applications, i.e. giving rise to no adverse events in patients etc.

The term "effective amount" as used herein means a dosage which is sufficient in order for the treatment of the patient to be effective compared with no treatment.

The term "therapeutically effective amount" of a compound as used herein means an amount sufficient to cure, alleviate or partially arrest the clinical manifestations of a given disease and its complications. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

The term "metabolite" as used herein is any intermediate or product resulting from metabolism.

The term "metabolism" as used herein refer to the biotransformation of a drug substance (in this invention, a compound of general formula I) administered to a patient.

The representative examples mentioned above are specific embodiments of this invention.

SUMMARY OF THIS INVENTION

The invention relates to compounds of the general formula I specified in the claims below. The compounds of this invention differ structurally from the known compounds.

The invention also relates to the use of said compounds in therapy, and in particular to pharmaceutical compositions comprising said compounds.

In another embodiment, the invention relates to methods of treatment, the method comprising administering to a subject in need thereof an effective amount of one or more compounds according to formula I.

In a still further embodiment, the invention relates to the use of compounds according to formula I in the manufacture of medicaments.

DESCRIPTION OF THE PREFERRED EMBODIMENTS

Due to their interaction with the histamine H3 receptor, the compounds of this invention as defined in the claims below and elsewhere in this specification are useful in the treatment of a wide range of conditions and disorders in which an interaction with the histamine H3 receptor is beneficial. Thus, the compounds may find use, e.g., in the treatment of diseases of the central nervous system, the peripheral nervous system, the cardiovascular system, the pulmonary system, the gastrointestinal system and the endocrinological system.

In the following, different, individual embodiments and clauses of this invention are mentioned and these individual embodiments and clauses can be combined in any appropriate way and/or order:

a) $R^1$ is cyclopentyl, cyclopropyl or isopropyl.
b) $R^1$ is $C_{1-6}$-alkyl or $C_{3-8}$-cycloalkyl.
c) $R^2$ is hydrogen.
d) $R^1$ and $R^2$ are together 1,4-butylene.
e) $R^1$ and $R^2$ are together $C_{1-6}$-alkylene, preferably $C_{1-4}$-alkylene.
f) $R^3$ is hydrogen.
g) $R^3$ is not hydrogen.
h) $R^4$ is hydrogen.
i) $R^4$ is not hydrogen.
j) $R^5$ is chloro, cyano, N,N-dimethylaminocarbonyl, N,N-dimethylaminomethyl, methoxy, 5-methyl-[1,2,4]oxodiazol-3-yl, morpholin-4-ylcarbonyl, morpholin-4-ylmethyl, 5-phenyl-[1,2,4]oxodiazol-3-yl, piperidin-1-ylcarbonyl, piperidin-1-ylmethyl, 5-pyridin-4-yl-[1,2,4]-oxodiazol-3-yl or pyrrolidin-1-ylmethyl.
k) $R^5$ is halogen, cyano, $C_{1-6}$-alkoxy, heterocyclyl-$C_{1-6}$-alkyl, heterocyclylcarbonyl or a group of the general formula —Y—(CH$_2$)$_s$—(C=O), —NR$^7$R$^8$, wherein $R^7$, $R^8$, r, s and Y each is as defined herein.
l) $R^5$ is heteroaryl optionally substituted with $C_{1-6}$-alkyl, aryl or heteroaryl.
m) $R^5$ is hydrogen.
n) $R^5$ is not hydrogen.
o) $R^6$ is chloro, cyano, N,N-dimethylaminocarbonyl, N,N-dimethylaminomethyl, methoxy, 5-methyl-[1,2,4]oxodiazol-3-yl, morpholin-4-ylcarbonyl, morpholin-4-ylmethyl, 5-phenyl-[1,2,4]oxodiazol-3-yl, piperidin-1-ylcarbonyl, piperidin-1-ylmethyl, 5-pyridin-4-yl-[1,2,4]-oxodiazol-3-yl or pyrrolidin-1-ylmethyl.
p) $R^6$ is halogen, cyano, $C_{1-6}$-alkoxy, heterocyclyl-$C_{1-6}$-alkyl, heterocyclylcarbonyl or a group of the general formula —Y—(CH$_2$), —(C=O), —NR$^7$R$^8$, wherein $R^7$, $R^8$, r, s and Y each is as defined herein.
q) $R^6$ is heteroaryl optionally substituted with $C_{1-6}$-alkyl, aryl or heteroaryl.
r) $R^6$ is hydrogen.
s) $R^6$ is not hydrogen.
t) At least two of the symbols $R^3$, $R^4$, $R^5$ and $R^6$ are different from hydrogen.
u) $R^7$ is methyl.
v) $R^7$ is $C_{1-6}$-alkyl.
w) $R^8$ is methyl.
x) $R^8$ is $C_{1-6}$-alkyl.
y) X is oxy (—O—).
z) X is sulphur (—S—).
aa) Y is a bond.
bb) m is 0.
cc) m is 1.
dd) m is 2.
ee) r is 0 or 1.
ff) s is 0 or 1.

Combining the above individual embodiments results in further embodiments and the present invention relates to all possible combinations of the above individual embodiments and all possible combinations with the individual claims below. It is obvious for the skilled art worker which of these embodiments that cannot be combined.

Examples of specific compounds of formula I are
1) 6-chloro-2-(4-cyclopentylpiperazin-1-yl)benzothiazole,
2) 2-(4-isopropylpiperazin-1-yl)-6-methoxybenzothiazole,
3) 2-(4-cyclopropylpiperazin-1-yl)-6-methoxybenzothiazole,
4) 2-(6-methoxybenzothiazol-2-yl)octahydropyrido[1,2-a]pyrazine,
5) 2-(4-isopropylpiperazin-1-yl)benzothiazole-6-carbonitrile,
6) [2-(4-isopropylpiperazin-1-yl)benzothiazol-6-yl]piperidin-1-ylmethanone,
7) 2-(4-isopropylpiperazin-1-yl)benzothiazole-6-carboxylic acid dimethylamide,
8) [2-(4-isopropylpiperazin-1-yl)benzothiazol-6-yl]morpholin-4-ylmethanone,
9) 2-(4-isopropylpiperazin-1-yl)-6-piperidin-1-ylmethylbenzothiazole,
10) 2-(4-isopropylpiperazin-1-yl)-6-(morpholin-4-ylmethyl)benzothiazole,
11) [2-(4-isopropylpiperazin-1-yl)benzothiazol-6-ylmethyl]dimethylamine,
12) 2-(4-isopropylpiperazin-1-yl)-6-(5-methyl-[1,2,4]oxadiazol-3-yl)benzothiazole,
13) 2-(4-isopropylpiperazin-1-yl)-6-(5-phenyl-[1,2,4]oxadiazol-3-yl)benzothiazole,
14) 2-(4-isopropylpiperazin-1-yl)-6-(5-pyridin-4-yl-[1,2,4]oxadiazol-3-yl)benzothiazole,
15) 2-(4-cyclopentylpiperazin-1-yl)benzothiazole-6-carbonitrile,
16) [2-(4-cyclopropylpiperazin-1-yl)benzothiazol-6-ylmethyl]dimethylamine,
17) 2-(4-cyclopropylpiperazin-1-yl)-6-(pyrrolidin-1-ylmethyl)benzothiazole,
18) 2-(4-cyclopropylpiperazin-1-yl)-6-(morpholin-4-ylmethyl)benzothiazole,
19) 2-(4-cyclopropylpiperazin-1-yl)-6-(piperidin-1-ylmethyl)benzothiazole,
20) N-[2-(4-cyclopropylpiperazin-1-yl)benzothiazol-6-yl]acetamide,
21) [2-(4-cyclopropylpiperazin-1-yl)benzothiazol-6-yl]-(4-methylpiperazin-1-yl)methanone,
22) 2-(4-cyclopropylpiperazin-1-yl)-6-(3,4-dimethoxyphenyl)benzothiazole, 23) 2-(4-cyclopropylpiperazin-1-yl)-6-(6-methoxypyridin-3-yl)benzothiazole,
24) 6-(5-chloro-2-methoxypyridin-4-yl)-2-(4-cyclopropylpiperazin-1-yl)benzothiazole,
25) 2-(6-piperidin-1-ylmethylbenzothiazol-2-yl)octahydropyrido[1,2-a]pyrazine,
26) N-{4-[2-(4-cyclopropylpiperazin-1-yl)benzothiazol-6-yl]phenyl}acetamide,
27) cyclopropyl-[2-(4-cyclopropylpiperazin-1-yl)benzothiazol-6-ylmethyl]amine,
28) 2-(4-cyclopropylpiperazin-1-yl)-6-(1,1-dioxo-1$\lambda^6$-isothiazolidin-2-ylmethyl)benzothiazole,
29) 2-(4-cyclopropylpiperazin-1-yl)-6-(1,1-dioxo-1$\lambda^6$-isothiazolidin-2-yl)benzothiazole,
30) 2-(4-isopropylpiperazin-1-yl)benzothiazole-5-carbonitrile,
31) 2-(4-isopropylpiperazin-1-yl)-5-pyrrolidin-1-ylmethylbenzothiazole,
32) [2-(4-isopropylpiperazin-1-yl)benzothiazol-5-ylmethyl]dimethylamine,
33) [2-(4-isopropylpiperazin-1-yl)benzothiazol-5-yl]pyrrolidin-1-ylmethanone,
34) 5-(1,1-dioxo-1$\lambda^6$-isothiazolidin-2-ylmethyl)-2-(4-isopropylpiperazin-1-yl)benzothiazole,
35) 2-(4-cyclopropylpiperazin-1-yl)benzooxazole-5-carbonitrile,
36) [2-(4-cyclopropylpiperazin-1-yl)benzoxazol-5-yl]pyrrolidin-1-ylmethanone,
37) 2-(4-cyclopropylpiperazin-1-yl)-5-(1,1-dioxo-1$\lambda^6$-isothiazolidin-2-ylmethyl)benzoxazole,
38) 2-(4-cyclopropylpiperazin-1-yl)-5-pyrrolidin-1-ylmethylbenzoxazole and
39) [2-(4-cyclopropylpiperazin-1-yl)benzoxazol-5-ylmethyl]dimethylamine,
and, in one aspect, this invention relates specifically to each of these compounds individually. In another aspect, this invention relates specifically to a pharmaceutically acceptable salt of each of these compounds individually, more specifically to the specific salts mentioned in the specific examples below.

In an embodiment of this invention, all except 4, preferably all except 3, more preferred all except 2, and most preferred all except 1, of the symbols mentioned in claim 1 below are those groups or moieties present in a compound of formula I mentioned individually in any one of the examples below and the remaining symbol or symbols is/are those mentioned in any of the individual embodiments a) through w).

The compounds of the present invention interact with the histamine H3 receptor and are accordingly particularly useful in the treatment of a variety of diseases or conditions in which histamine H3 interactions are beneficial.

In one aspect, the invention provides the use of a compound according to formula I in a pharmaceutical composition. The pharmaceutical composition may in another aspect of the invention comprise, as an active ingredient, at least one compound according to formula I together with one or more pharmaceutically acceptable carriers or excipients. In another aspect, the invention provides such a pharmaceutical composition in unit dosage form, comprising from about 0.05 mg to about 1000 mg, e.g., from about 0.1 mg to about 500 mg, such as from about 0.5 mg to about 200 mg of the compound according to formula I.

In another aspect, the invention provides the use of a compound of formula I as defined above for the preparation of a pharmaceutical composition for the treatment of diseases and disorders in which an inhibition of the H3 histamine receptor has a beneficial effect.

In another aspect, the invention provides the use of a compound of formula I for the preparation of a pharmaceutical composition having histamine H3 antagonistic activity or histamine H3 inverse agonistic activity.

In another aspect the invention provides the use of a compound of formula I for the preparation of a pharmaceutical composition for the reduction of weight.

In another aspect, the invention provides the use of a compound of formula I for the preparation of a pharmaceutical composition for the treatment of overweight or obesity.

In another aspect, the invention provides the use of a compound of formula I for the preparation of a pharmaceutical composition for the suppression of appetite or for satiety induction.

In another aspect, the invention provides the use of a compound of formula I for the preparation of a pharmaceutical composition for the prevention and/or treatment of disorders and diseases related to overweight or obesity, such as dyslipidaemia, coronary heart disease, gallbladder disease, osteoarthritis and various types of cancer such as endometrial, breast, prostate and colon cancers.

In another aspect, the invention provides the use of a compound of formula I for the preparation of a pharmaceutical composition for the prevention and/or treatment of eating disorders, such as bulimia or binge eating.

In another aspect, the invention provides the use of a compound of formula I for the preparation of a pharmaceutical composition for the treatment of IGT (Impaired glucose tolerance).

In another aspect, the invention provides the use of a compound of formula I for the preparation of a pharmaceutical composition for the treatment of type 2 diabetes.

In another aspect, the invention provides the use of a compound of formula I for the preparation of a pharmaceutical composition for the delaying or prevention of the progression from IGT to type 2 diabetes.

In another aspect, the invention provides the use of a compound of formula I for the preparation of a pharmaceutical composition for the delaying or prevention of the progression from non-insulin requiring type 2 diabetes to insulin requiring type 2 diabetes.

In another aspect, the invention provides the use of a compound of formula I for the preparation of a pharmaceutical composition for the treatment of diseases and disorders in which a stimulation of the H3 histamine receptor has a beneficial effect.

In another aspect, the invention provides the use of a compound of formula I for the preparation of a pharmaceutical composition having histamine H3 agonistic activity.

In another aspect, the invention provides the use of a compound of formula I for the preparation of a pharmaceutical composition for the treatment of allergic rhinitis, ulcer or anorexia.

In another aspect, the invention provides the use of a compound of formula I for the preparation of a pharmaceutical composition for the treatment of Alzheimer's disease, narcolepsy, attention deficit disorders or reduced wakefulness, or for the regulation of sleep.

In another aspect, the invention relates to the use of a compound of formula I for the preparation of a pharmaceutical preparation for the treatment of airway disorders, such as asthma, for regulation of gastric acid secretion, or for treatment of diarrhea.

In another aspect, the invention provides a method for the treatment of disorders or diseases related to the H3 histamine receptor, the method comprising administering to a subject in need thereof an effective amount of a compound of the general formula I as defined above, or of a pharmaceutical composition comprising such a compound.

In another aspect, the invention provides a method as described above, wherein the effective amount of the compound of the general formula I as defined above is in the range of from about 0.05 mg to about 2000 mg, preferably from about 0.1 mg to about 1000 mg, and more preferably from about 0.5 mg to about 500 mg per day.

In one aspect, the invention relates to compounds which exhibit histamine H3 receptor antagonistic activity or inverse agonistic activity and which may accordingly be useful in the treatment of a wide range of conditions and disorders in which histamine H3 receptor blockade is beneficial.

In another aspect, the invention provides a method for reduction of weight, the method comprising administering to a subject in need thereof an effective amount of a compound of formula I as defined above.

In another aspect, the invention provides a method for treatment of overweight or obesity, the method comprising administering to a subject in need thereof an effective amount of a compound of formula I.

In another aspect, the invention provides a method for suppression of appetite or for satiety induction, the method comprising administering to a subject in need thereof an effective amount of a compound of formula I.

In another aspect, the invention provides a method for prevention and/or treatment of disorders or diseases related to overweight or obesity, such as dyslipidaemia, coronary heart disease, gallbladder disease, osteoarthritis and various types of cancer, e.g., endometrial, breast, prostate or colon cancer, the method comprising administering to a subject in need thereof an effective amount of a compound of formula I.

In another aspect, the invention provides a method for prevention and/or treatment of eating disorders, such as bulimia and binge eating, the method comprising administering to a subject in need thereof an effective amount of a compound of formula I.

In another aspect, the invention provides a method for the treatment of IGT (Impaired glucose tolerance), the method comprising administering to a subject in need thereof an effective amount of a compound of formula I.

In another aspect, the invention provides a method for the treatment of type 2 diabetes, the method comprising administering to a subject in need thereof an effective amount of a compound of formula I.

In another aspect, the invention provides a method for the delaying or prevention of the progression from IGT to type 2 diabetes, the method comprising administering to a subject in need thereof an effective amount of a compound of formula I.

In another aspect, the invention provides a method for the delaying or prevention of the progression from non-insulin requiring type 2 diabetes to insulin requiring type 2 diabetes, the method comprising administering to a subject in need thereof an effective amount of a compound of formula I.

In another aspect, the invention relates to compounds which exhibit histamine H3 receptor agonistic activity and which may accordingly be useful in the treatment of a wide range of conditions and disorders in which histamine H3 receptor activation is beneficial.

Compounds of the present invention may also be used for the treatment of airway disorders (such as asthma), as antidiarrheals, and for the modulation of gastric acid secretion.

Furthermore, compounds of the present invention may be used for the treatment of diseases associated with the regulation of sleep and wakefulness, and for the treatment of narcolepsy and attention deficit disorders.

Moreover, compounds of the invention may be used as CNS stimulants or as sedatives.

The present compounds may also be used for the treatment of conditions associated with epilepsy. Additionally, compounds of the invention may be used for the treatment of motion sickness and vertigo. Furthermore, they may be useful as regulators of hypothalamo-hypophyseal secretion, as antidepressants, as modulators of cerebral circulation, and in the treatment of irritable bowel syndrome.

Further, compounds of the present invention may be used for the treatment of dementia and Alzheimer's disease.

Compounds of the present invention may also be useful for the treatment of allergic rhinitis, ulcer or anorexia.

Compounds of the present invention may furthermore be useful for the treatment of migraine [see, e.g., *The Journal of Pharmacology and Experimental Therapeutics* 1998; 287: 43-50] and for the treatment of myocardial infarction [see *Expert Opinion on Investigational Drugs* 2000; 9: 2537-42].

In a further aspect of the invention, treatment of a patient with a compound of the present invention is combined with diet and/or exercise.

In a further aspect of the invention, one of more compounds of the present invention is/are administered in combination with one or more further active substances in any suitable ratio(s). Such further active agents may, for example, be selected from antiobesity agents, antidiabetics, antidyslipidemic agents, antihypertensive agents, agents for the treatment of complications resulting from or associated with diabetes, and agents for the treatment of complications and disorders resulting from or associated with obesity.

Thus, in a further aspect of the invention one or more compounds of the present invention may be administered in combination with one or more antiobesity agents or appetite regulating agents. Such agents may, for example, be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR β agonists, AGRP (Agouti related protein) inhibitors, opioid antagonists (such as naltrexone), exendin-4, GLP-1 and ciliary neurotrophic factor.

In one embodiment of the invention, an antiobesity agent administered in combination with one or more compounds of the invention is leptin.

In another embodiment, such an antiobesity agent is dexamphetamine or amphetamine.

In another embodiment, such an antiobesity agent is fenfluramine or dexfenfluramine.

In still another embodiment, such an antiobesity agent is sibutramine.

In a further embodiment, such an antiobesity agent is orlistat.

In another embodiment, such an antiobesity agent is mazindol or phentermine.

In still another embodiment, such an antiobesity agent is phendimetrazine, diethylpropion, fluoxetine, bupropion, topiramate or ecopipam.

In yet a further aspect of the invention, one or more compounds of the present invention may be administered in combination with one or more antidiabetic agents. Relevant antidiabetic agents include insulin, insulin analogues and derivatives such as those disclosed in EP 0 792 290 (Novo Nordisk A/S), e.g., $N^{\epsilon B29}$-tetradecanoyl des(B30) human insulin, EP 0 214 826 and EP 0 705 275 (Novo Nordisk A/S), e.g., $Asp^{B28}$ human insulin, U.S. Pat. No. 5,504,188 (Eli Lilly), e.g., $Lys^{B28}$ $Pro^{B29}$ human insulin, EP 0 368 187 (Aventis), e.g., Lantus®, all of which are incorporated herein by reference, GLP-1 derivatives, such as those disclosed in WO 98/08871 (Novo Nordisk A/S), incorporated herein by reference, as well as orally active hypoglycaemic agents.

The orally active hypoglycaemic agents preferably comprise imidazolines, sulfonylureas, biguanides, meglitinides, oxadiazolidinediones, thiazolidinediones, insulin sensitizers, α-glucosidase inhibitors, agents acting on the ATP-dependent potassium channel of the β-cells, e.g., potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists, such as one of those disclosed in WO 99/01423 and WO 00/39088 (Novo Nordisk A/S and Agouron Pharmaceuticals, Inc.), both of which are incorporated herein by reference, GLP-1 agonists, such as those disclosed in WO 00/42026 (Novo Nordisk A/S and Agouron Pharmaceuticals, Inc.), incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention, one or more compounds of the present invention may be administered in combination with insulin or an insulin analogue or derivative, such as $N^{\epsilon B29}$-tetradecanoyl des(B30) human insulin, $Asp^{B28}$ human insulin, $Lys^{B28}$ $Pro^{B29}$ human insulin, Lantus®, or a mix-preparation comprising one or more of these.

In a further embodiment of the invention, one or compounds of the present invention may be administered in combination with a sulfonylurea, e.g., tolbutamide, chlorpropamide, tolazamide, glibenclamide, glipizide, glimepiride, glicazide or glyburide.

In another embodiment of the invention, one or more compounds of the present invention may be administered in combination with a biguanide, e.g., metformin.

In yet another embodiment of the invention, one or more compounds of the present invention may be administered in combination with a meglitinide, e.g., repaglinide or nateglinide.

In still another embodiment of the invention, one or more compounds of the present invention may be administered in combination with a thiazolidinedione insulin sensitizer, e.g., troglitazone, ciglitazone, pioglitazone, rosiglitazone, isaglitazone, darglitazone, englitazone, CS-011/CI-1037 or T 174, or a compound disclosed in WO 97/41097, WO 97/41119, WO 97/41120, WO 00/41121 and WO 98/45292, all of which are incorporated herein by reference.

In still another embodiment of the invention, one or more compounds of the present invention may be administered in combination with an insulin sensitizer, e.g., such as GI 262570, YM-440, MCC-555, JTT-501, AR-H039242, KRP-297, GW-409544, CRE-16336, AR-H049020, LY510929, MBX-102, CLX-0940, GW-501516, or a compound disclosed in WO 99/19313, WO 00/50414, WO 00/63191, WO 00/63192 or WO 00/63193 or in WO 00/23425, WO 00/23415, WO 00/23451, WO 00/23445, WO 00/23417, WO 00/23416, WO 00/63153, WO 00/63196, WO 00/63209, WO 00/63190 or WO 00/63189 (Novo Nordisk A/S), all of which are incorporated herein by reference.

In a further embodiment of the invention, one or more compounds of the present invention may be administered in combination with an α-glucosidase inhibitor, e.g., voglibose, emiglitate, miglitol or acarbose.

In another embodiment of the invention, one or more compounds of the present invention may be administered in combination with an agent acting on the ATP-dependent potassium channel of the 6-cells, e.g., tolbutamide, glibenclamide, glipizide, glicazide, BTS-67582 or repaglinide.

In yet another embodiment of the invention, one or more compounds of the present invention may be administered in combination with nateglinide.

In still another embodiment, one or more compounds of the present invention may be administered in combination with an antihyperlipidemic agent or antilipidemic agent, e.g., cholestyramine, colestipol, clofibrate, gemfibrozil, lovastatin, pravastatin, simvastatin, probucol or dextrothyroxine.

In still another embodiment of the invention, one or more compounds of the present invention may be administered in combination with an antilipidemic agent, e.g., cholestyramine, colestipol, clofibrate, gemfibrozil, lovastatin, pravastatin, simvastatin, probucol or dextrothyroxine.

In another aspect of the invention, one or more compounds of the present invention may be administered in combination with more than one of the above-mentioned compounds, e.g., in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, one or more compounds of the present invention may be administered in combination with one or more antihypertensive agents. Examples of antihypertensive agents are 6-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: *The Science and Practice of Pharmacy*, $19^{th}$ Edition, Gennaro, Ed., Mack Publishing Co., Easton, Pa., 1995.

It should be understood that any suitable combination of compounds according to the invention with diet and/or exercise, one or more of the above-mentioned compounds and optionally one or more other active substances are considered to be within the scope of the present invention.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in *J Pharm Sci* 1977; 66: 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. Alternatively, the free base may be dissolved in a suitable solvent containing the appropriate acid, and the salt isolated by evaporating the solvent or otherwise separating the salt and solvent.

Compounds of the present invention may form solvates with standard low molecular weight solvents using methods well known to the person skilled in the art. Such solvates are also to be understood as being within the scope of the present invention.

The invention also encompasses prodrugs of the present compounds which following administration undergo chemical conversion by metabolic processes before becoming active pharmacological substances. In general, such prodrugs will be functional derivatives of the present compounds which are readily convertible in vivo into the required compound of the formula I. Conventional procedures for the selection and preparation of suitable prodrug derivatives are described, for example, in *Design of Prodrugs*, ed. H. Bundgaard, Elsevier, 1985.

This invention also encompasses active metabolites of the present compounds.

Combining one or more of the individual embodiments described herein, optionally also with one or more of the individual claims below, results in further embodiments and the present invention relates to all possible combinations of said embodiments and claims.

In one embodiment, this invention relates to compounds of formula I with the definitions given herein, with the proviso that when $R^1$ is hydrogen, $C_{1-6}$-alkyl, $C_{2-6}$-alkenyl, $C_{3-8}$-cycloalkyl or $C_{3-8}$-cycloalkyl-$C_{1-6}$-alkyl, $R^2$ is hydrogen or $C_{1-6}$-alkyl; or $R^1$ and $R^2$ together with the atoms they are connected to form a nitrogen containing ring, optionally another heterocyclyl group; m is 0 (zero), 1 or 2; one of the four substituents $R^3$, $R^4$, $R^5$ and $R^6$ is any of the groups halogen, hydroxy, cyano or $C_{1-6}$-alkyl and three of the four substituents $R^3$, $R^4$, $R^5$ and $R^6$ are hydrogen, then X is different from —S—, and, in another embodiment, this invention relates to the use of such compounds as medicament and, in a still further embodiment, this invention relates to the use of such compounds for the treatment of any specific disease mentioned herein or any specific condition mentioned herein.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques, such as those disclosed in Remington: *The Science and Practice of Pharmacy*, 19$^{th}$ Edition, Gennaro, Ed., Mack Publishing Co., Easton, Pa., 1995.

The pharmaceutical compositions may be specifically formulated for administration by any suitable route, such as the oral, rectal, nasal, pulmonary, topical (including buccal and sublingual), transdermal, intracisternal, intraperitoneal, vaginal or parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings, such as enteric coatings, or they can be formulated so as to provide controlled release of the active ingredient, such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also to be understood as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferably from about 0.05 to about 10 mg/kg body weight per day, administered in one or more doses, such as from 1 to 3 doses. The exact dosage will depend upon the frequency and mode of administration, the sex, age, weight and general condition of the subject treated, the nature and severity of the condition treated and any concomitant diseases to be treated, and other factors evident to those skilled in the art.

The formulations may conveniently be presented in unit dosage form by methods known to those skilled in the art. A typical unit dosage form for oral administration one or more times per day, such as from 1 to 3 times per day, may contain from 0.05 to about 1000 mg, preferably from about 0.1 to about 500 mg, and more preferably from about 0.5 mg to about 200 mg of a compound (or a salt or other derivative thereof as set forth above), according to the invention.

For parenteral routes, such as intravenous, intrathecal, intramuscular and similar administration, typical doses are of the order of about half the dose employed for oral administration.

The compounds of this invention are generally utilized as the free substance or as a pharmaceutically acceptable salt thereof. One example is an acid addition salt of a compound having a free base functionality. When a compound of the formula I contains a free base functionality, such salts are prepared in a conventional manner by treating a solution or suspension of the free base form of the compound of formula I with a chemical equivalent (acid-base equivalent) of a pharmaceutically acceptable acid. Representative examples of relevant inorganic and organic acids are mentioned above. Physiologically acceptable salts of a compound of the invention having a hydroxy group include the anion of said compound in combination with a suitable cation, such as sodium or ammonium ion.

For parenteral administration, solutions of the novel compounds of the formula I in sterile aqueous solution, aqueous propylene glycol or sesame or peanut oil may be employed. Such aqueous solutions should be suitably buffered if necessary, and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylenes or water. Similarly, the carrier or diluent may include any sustained release material known in the art, such as glyceryl monostearate or glyceryl distearate, alone or mixed with a wax. The pharmaceutical compositions formed by combining the novel compounds of the formula I and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier may vary widely, but will usually be from about 25 mg to about 1 g. If a liquid carrier is used, the preparation may be in the form of a syrup, emulsion, soft gelatine capsule or sterile injectable liquid, such as an aqueous or non-aqueous liquid suspension or solution.

A typical tablet, which may be prepared by conventional tabletting techniques, may in the core contain 5.0 mg of a compound of the invention, 67.8 mg of lactosum Ph. Eur., 31.4 mg of cellulose, microcrystalline (Avicel), 1.0 mg of Amberlite®IRP88 (i.e., Polacrillin potassium NF, tablet disintegrant, Rohm and Haas) and magnesii stearas Ph. Eur. q.s. with a coating of approximately 9 mg of hydroxypropyl methylcellulose and approximately 0.9 mg of Mywacett 9-40 T (being acylated monoglyceride used as plasticizer for film coating).

If desired, the pharmaceutical composition of this invention may comprise the compound of the formula I in combination with one or more further pharmacologically active substances, e.g., substances chosen among those described in the foregoing.

Briefly, the compounds of this invention can be prepared in a manner known per se or analogous with known processes.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law).

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents. The mentioning herein of references is no admission that they constitute prior art.

Herein, the word "comprise" is to be interpreted broadly meaning "include", "contain" or "comprehend" (EPO guidelines C 4.13).

This invention includes all modifications and equivalents of the subject matter recited in the claims appended hereto as permitted by applicable law.

The following examples are offered by way of illustration, not by limitation.

EXAMPLES

The representative examples mentioned above are specific embodiments of this invention. In the examples below, the following terms are intended to have the following, general meanings: d is day(s), g is gram(s), h is hour(s), Hz is hertz, kD is kiloDalton(s), L is liter(s), M is molar, mbar is millibar, mg is milligram(s), min is minute(s), mL is milliliter(s), mM is millimolar, mmol is millimole(s), mol is mole(s), N is normal, ppm is parts per million, psi is pounds per square inch, APCI is atmospheric pressure chemical ionization, ESI is electrospray ionization, I.v. is intravenous, m/z is mass to charge ratio, mp/Mp is melting point, MS is mass spectrometry, HPLC is high pressure liquid chromatography, RP is reverse phase, HPLC-MS is high pressure liquid chromatography-mass spectrometry, NMR is nuclear magnetic resonance spectroscopy, p.o. is per oral, $R_f$ is relative TLC mobility, rt is room temperature, s.c. is subcutaneous, TLC is thin layer chromatography, $t_r$ is retention time, BOP is (1benzotriazolyloxy)tris(dimethylamino)phosphoniumhexafluorophosphate, CDI is carbonyldiimidazole, DCM is dichloromethane, $CH_2Cl_2$, methylenechloride, DBU is 1,8-diazabicyclo[5.4.0]undec-7-ene, DEAD is diethyl azodicarboxylate, DIC is 1,3-diisopropyl-carbodiimide, DIPEA is N,N-diisopropylethylamine, DMA is N,N-dimethylacetamide, DMF is N,N-dimethylformamide, DMPU is N,N'-dimethylpropyleneurea, 1,3-dimethyl-2-oxohexahydropyrimidine, DMSO is dimethylsulfoxide, EDAC is 1-ethyl-3-(3-dimethylaminopropyl)carbodiimide hydrochloride, $Et_2O$ is diethyl ether, EtOAc is ethyl acetate, HMPA is hexamethylphosphoric acid triamide, HOAt is 1-hydroxy-7-azabenzotriazole, HOBt is 1-hydroxybenzotriazole, LAH is lithium aluminum hydride ($LiAlH_4$), LDA is lithium diisopropylamide, MeCN is acetonitrile, MeOH is methanol, NMM is N-methyl-morpholine (4-methylmorpholine), NMP is N-methylpyrrolidin-2-one, TEA is triethylamine, TFA is trifluoroacetic acid, THF is tetrahydrofuran, THP is tetrahydropyranyl, TTFH is fluoro-N,N,N',N'-tetramethylformamidinium hexafluorophosphate, $CDCl_3$ is deuterio chloroform, $CD_3OD$ is tetradeuterio methanol and DMSO-$d_6$ is hexadeuterio dimethylsulfoxide.

Briefly, the compounds of this invention can be prepared in a manner known per se or analogous with known processes.

General Experimental Procedures

NMR spectra were recorded on a Bruker 300 or 400 MHz spectrometer. Shifts (δ) are given in parts per million (ppm) down field from tetramethylsilane as internal reference standard.

HPLC Method A.

The RP-analyses was performed on a Shimadzu LC-20 using a YMC-ODS, 5.0 µm, 4.6×50 mm; gradient elution, 0% to 30% solvent B (0.1% TFA in acetonitrile) in solvent A (0.1% TFA in water) within 6 min, and then kept for 2 min, 2.5 mL/min, detection at 220 nm, temperature 30° C.

HPLC Method B.

The RP-analyses was performed on a Shimadzu LC-20 using a YMC-ODS, 5.0 µm, 4.6×50 mm; gradient elution, 0% to 60% solvent B (0.1% TFA in acetonitrile) in solvent A (0.1% TFA in water) within 8 min, and then kept for 2 min, 2.5 mL/min, detection at 220 nm, temperature 30° C.

The examples below and the general procedures described herein refer to intermediate compounds and final products for general formula I identified in the specification and in the synthesis schemes. The preparation of the compounds of general formula I of the present invention is described in detail using the following examples. Occasionally, the reaction may not be applicable as described to each compound included within the disclosed scope of the invention. The compounds for which this occurs will be readily recognised by those skilled in the art. In these cases, the reactions can be successfully performed by conventional modifications known to those skilled in the art which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds or by the General Procedures A through G described herein. The following examples are offered by way of illustration, not by limitation.

General Procedure A

Compounds of formula I, wherein X, $R^1$, $R^2$, $R^3$, $R^4$, $R^5$, $R^6$ and m is as defined for formula I, (which compounds here are designated formula Ia) can be prepared as outlined below:

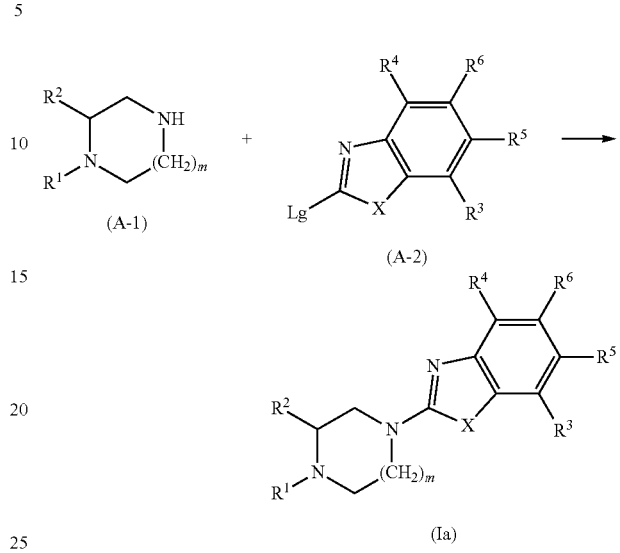

An amine of formula A-1, wherein $R^1$, $R^2$ and m is as defined herein, may be reacted with a substituted benzothiazole of the formula A-2 wherein $R^3$, $R^4$, $R^5$, and $R^6$ each is as defined herein, and Lg represents a leaving group such as methylthio, chlorine, bromine or iodine, to give a compound of formula Ia. This reaction may be carried out in a suitable solvent like, for example, dimethylsulfoxide, at a temperature of up to reflux. Compounds of formula A-2 may be prepared from, e.g., the corresponding 2-amino- or 2-mercapto substituted heterocycles according to known procedures.

General Procedure B

Compounds of formula I, wherein X, $R^1$, $R^2$, $R^3$, $R^4$, $R^5$, $R^6$ and m is as defined for formula I, (which compounds here are designated formula Ib) can be prepared as outlined below:

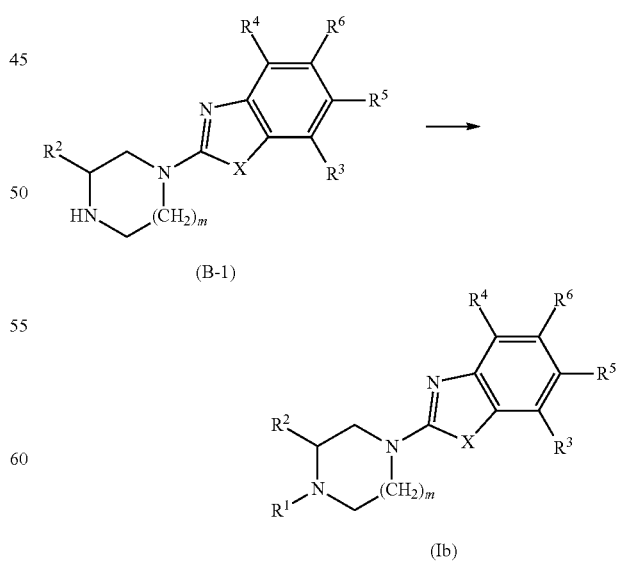

An amine of formula B-1, wherein X, $R^1$, $R^2$, $R^3$, $R^4$, $R^5$, $R^6$ and m each is as defined herein may be reacted with an aliphatic halogenide, to give a compound of formula Ib. This reaction may be carried out in a suitable solvent like, for example, dimethylformamide, dimethylsulfoxide, acetonitril or 2-butanone, at a temperature of up to reflux. The reaction may be carried out in the presence of a base such as, for example, sodium hydride, potassium carbonate or N,N-diisopropylethylamine, and a catalyst like, for example, potassium iodide. Compounds of formula B-1 may be prepared according to other General Procedure(s) described herein.

General Procedure C

Compounds of formula I, wherein X, $R^1$, $R^2$, $R^3$, $R^4$, $R^5$, $R^6$ and m is as defined for formula I, (which compounds here are designated formula Ic) can be prepared as outlined below:

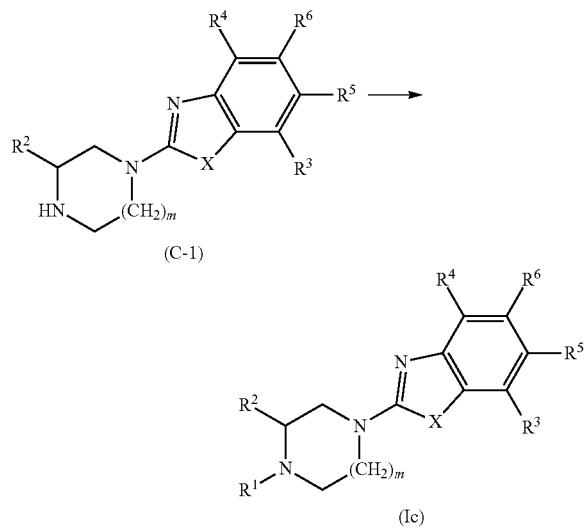

An amine of formula C-1, wherein X, $R^1$, $R^2$, $R^3$, $R^4$, $R^5$, $R^6$ and m each is as defined herein may be reacted with a ketone or aldehyde in the presence of a reducing agent, to give a compound of formula Ic. This reaction may be carried out in a suitable solvent like, for example, tetrahydrofuran or 1,2-dichloroethane, at a temperature of up to reflux. The reducing agent may be, for example, $NaCNBH_3$ or $NaBH(OAc)_3$, eventually in the presence of a acidic catalyst like, for example, acetic acid. Compounds of formula C-1 may be prepared according to other General Procedure(s) described herein.

General Procedure D

Compounds of formula I, wherein one of $R^3$, $R^4$, $R^5$ or $R^6$ is —(C=O)—$NR^7R^8$ and $R^7$ and $R^8$ are as defined for formula I, (which compounds here are designated formula Id) can be prepared as outlined below:

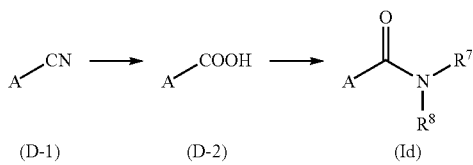

A carboxylic acid of formula D-2 may be reacted with an amine of formula $R^7R^8NH$ to give an amide of formula Id. This reaction may be carried out by activation of the carboxylic acid with, for example, HOBt/EDAC in a suitable solvent like, for example, THF and at a temperature of up to reflux. A carboxylic acid of formula D-2 may be prepared by hydrolysis of a nitrile of formula D-1. This reaction may be carried out under strong acidic conditions, for example, in 6 N hydrochloric acid at a temperature of up to reflux. Compounds of formula D-1 may be prepared according to other General Procedure(s) described herein.

General Procedure E

Compounds of formula I, wherein one of $R^3$, $R^4$, $R^5$ or $R^6$ is —$CH_2$—$NR^7R^8$ and $R^7$ and $R^8$ are as defined for formula I, (which compounds here are designated formula Ie) can be prepared as outlined below:

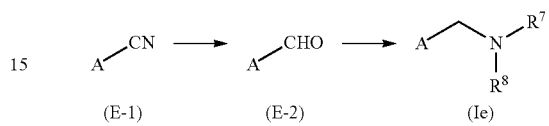

A carboxaldehyde of formula E-2 may be reacted with an amine of formula $R^7R^8NH$ under reducing conditions to give an amine of formula Ie. This reaction may be carried out in a suitable solvent like, for example, tetrahydrofuran or 1,2-dichloroethane, at a temperature of up to reflux. The reducing agent may be, for example, $NaCNBH_3$ or $NaBH(OAc)_3$, eventually in the presence of a acidic catalyst like, for example, acetic acid. A carboxaldehyde of formula E-2 may be prepared by reduction of a nitrile of formula E-1. This reaction may be carried out in a suitable solvent like, for example, tetrahydrofuran or 1,2-dichloroethane, at a temperature of up to reflux. The reducing agent may be, for example, DIBAH. Compounds of formula E-1 may be prepared according to other General Procedure(s) described herein.

General Procedure F

Compounds of formula I, wherein one of $R^3$, $R^4$, $R^5$ or $R^6$ is a substituted 1,2,4-oxadiazol-3-yl as defined for formula I, (which compounds here are designated formula If) can be prepared as outlined below:

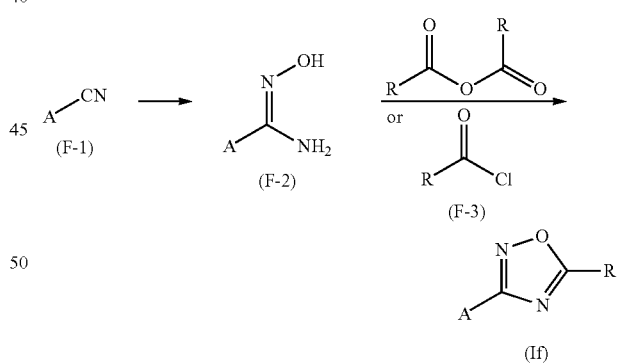

A hydroxyamidine of formula F-2 may be reacted with a carboxylic acid chloride or anhydride of formula F-3 to give a compound of formula Id. This reaction may be carried out in a suitable solvent like, for example, N,N-dimethylacetamide or acetic acid, at a temperature of up to reflux. Compounds of formula F-2 may be prepared by reaction of a nitril of formula F-1 with hydroxylamine. This reaction may be carried out in a suitable solvent like, for example, ethanol and water, at a temperature of up to reflux in the presence of a base like, for example, potassium carbonate. Compounds of formula F-1 may be prepared according to other General Procedures described herein.

General Procedure G

Compounds of formula I, wherein one of $R^3$, $R^4$, $R^5$ or $R^6$ is cyano, (which compounds here are designated formula Ig) can be prepared as outlined below:

A bromide of formula G-1 may be reacted with copper(I) cyanide in the presence of a catalyst like, for example, copper (I)iodide to give a nitrile of formula Ie. This reaction may be carried out in a suitable solvent like, for example, N-methylpyrrolidone at a temperature of up to reflux. Compounds of formula G-1 may be prepared according to other General Procedure(s) described herein.

General Procedure H

Compounds of formula I, wherein one of $R^3$, $R^4$, $R^5$ or $R^6$ is —NH(C=O)—R, (which compounds here are designated formula Ih) can be prepared as outlined below:

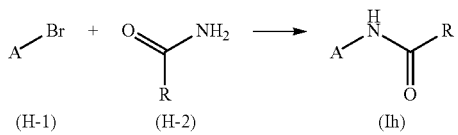

A bromide of formula H-1 may be reacted with a carboxamide of formula H-2 in the presence of a catalyst like, for example, $Pd(OAc)_2$, to give an acylated amine of formula Ih. This reaction may be carried out in a suitable solvent like, for example, 1,4-dioxane in the presence of a base like, for example, $Cs_2CO_3$, at a temperature of up to reflux. Compounds of formula H-1 may be prepared according to other General Procedure(s) described herein.

General Procedure I

Compounds of the formula I, wherein one of $R^3$, $R^4$, $R^5$ or $R^6$ is A', (which compounds here are designated formula Ii), can be prepared as outlined below:

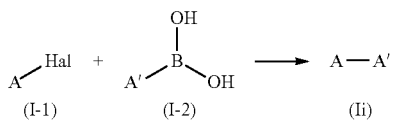

A compound of formula I-1, wherein Hal represents chlorine, bromine or iodine, may be reacted with a (hetero)aromaticboronic acid derivative of the formula I-2, or a corresponding boronic acid ester derivative, to give a compound of formula Ii. This reaction may be carried out in a suitable solvent like, for example, acetonitrile/water, at a temperature of up to 150° C. in the presence of a suitable catalyst like, for example, bistriphenylphosphinpalladium(II)di-chloride and sodium carbonate. This reaction may also be performed in the other way round starting from reactants wherein the halogen and boronic acid moieties have been interchanged. This reaction may be carried out under similar conditions as described above. Compounds of formula I-1 may be may be prepared according to other General Procedure(s) described herein.

General Procedure N

Compounds of the formula I, wherein $R^3$, $R^4$, $R^5$ or $R^6$ is a cyclic sulphonamide and wherein p is 1-4, as defined for formula I, which compounds here are designated formula In, can be prepared as outlined below:

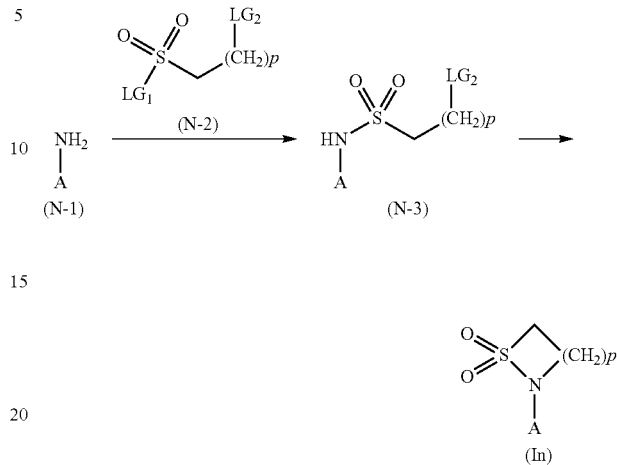

An aromatic amine of formula N-1 may be reacted with an activated sulfonic acid of formula N-2, wherein p is 1-4 and $LG_1$ and $LG_2$ represents suitable leaving groups such as, for example, halogen, to give a compound of formula N-3. This reaction may be carried out in a suitable solvent like, for example, DMF, at a temperature of up to reflux and in the presence of a base like, for example, TEA. A compound of formula N-3 may be ring-closed to give a compound of formula In. This reaction may be carried out in a suitable solvent like, for example, DMF, at a temperature of up to reflux and in the presence of a base like, for example, NaH. Compounds of formula N-1 may be may be prepared according to other General Procedure(s) described herein.

General Procedure O

Compounds of formula I, wherein one of $R^3$, $R^4$, $R^5$ or $R^6$ is —$CH_2$—$NR^7R^8$ and $R^7$ and $R^8$ are as defined for formula I, (which compounds here are designated formula Io) can be prepared as outlined below:

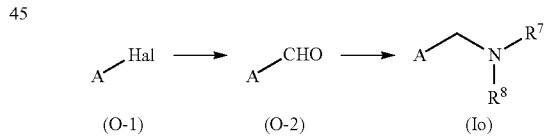

A carboxaldehyde of formula O-2 may be reacted with an amine of formula $R^7R^8NH$ under reducing conditions to give an amine of formula Io. This reaction may be carried out in a suitable solvent like, for example, tetrahydrofuran or 1,2-dichloroethane, at a temperature of up to reflux. The reducing agent may be, for example, $NaCNBH_3$ or $NaBH(OAc)_3$, eventually in the presence of a acidic catalyst like, for example, acetic acid. A carboxaldehyde of formula O-2 may be prepared from a halogenide of formula O-1 by reaction with a strong base like, for example, n-butyllithium followed by addition of a formylating agent like, for example, DMF. This reaction may be carried out in a suitable solvent like, for example, tetrahydrofuran at a temperature down to −78° C.

Compounds of formula O-1 may be prepared according to other General Procedure(s) described herein.

Example 1

General Procedure A

6-Chloro-2-(4-cyclopentylpiperazin-1-yl)benzothiazole, hydrochloride

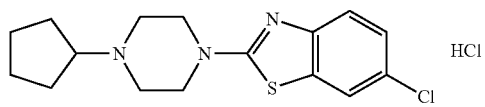 [SMILES: Clc1ccc2nc(N3CCN(C4CCCC4)CC3)sc2c1 ; Cl]

A mixture of 2,6-dichlorobenzothiazole (0.39 g, 1.9 mmol), 1-cyclopentylpiperazine (0.22 g, 1.4 mmol) and dimethylsulfoxide (2.0 mL) was stirred at 130° C. for 23 h. The reaction mixture was allowed to cool and water (50 mL) and potassium carbonate (1 g) was added. The resulting mixture was extracted with a mixture of ethyl acetate and dichloromethane and filtered. The filtrate was separated and the organic extract was washed with brine (2×) and dried (MgSO$_4$). The volatiles were evaporated to give a solid residue which was dissolved into a mixture of ethanol (30 mL) and 1 N hydrochloric acid (2.5 mL). Toluene was added and the mixture was concentrated. Ethanol and toluene was added and the mixture was concentrated again. This afforded a solid which was treated with ethanol (50 mL) and heated to reflux temperature. The resulting mixture was left overnight for crystallization. This afforded after filtration and drying 0.35 g (69%) of 6-chloro-2-(4-cyclopentylpiperazin-1-yl)-benzothiazole, hydrochloride.

Example 2

General Procedure A 2-(4-Isopropylpiperazin-1-yl)-6-methoxybenzothiazole, hydrochloride

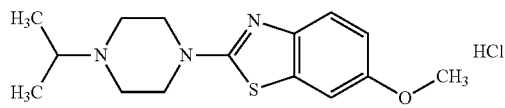 [SMILES: COc1ccc2nc(N3CCN(C(C)C)CC3)sc2c1 ; Cl]

A mixture of 2-chloro-6-methoxybenzothiazole (0.20 g, 1.0 mmol) and 1-isopropylpiperazine (0.26 g, 2.0 mmol) was stirred at 120° C. for 2 h. The reaction mixture was allowed to cool and worked up by extraction with ethyl acetate. The organic extract was washed with a NaHCO$_3$ solution and water (3×). The organic phase was extracted with 0.25 M hydrochloric acid (10 mL). The acidic aqueous extract was concentrated and re-evaporated with ethanol. The residue was crystallized from a mixture of ethanol and ethyl acetate to give 260 mg (80%) of 2-(4-isopropylpiperazin-1-yl)-6-methoxybenzothiazole, hydrochloride.

$^1$H-NMR (400 MHz, DMSO-d$_6$) δ 11.7 (brs, 1H), 7.52 (d, 1H), 7.49 (d, 1H), 6.97 (dd, 1H), 4.23-4.15 (m, 2H), 3.88-3.75 (m, 5H), 3.55-3.47 (m, 3H), 3.28-3.15 (m, 2H), 1.32 (d, 6H).

Example 3

General Procedure A 2-(4-Cyclopropylpiperazin-1-yl)-6-methoxybenzothiazole, hydrochloride

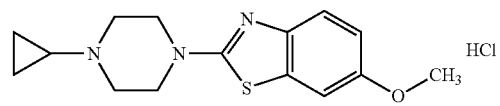 [SMILES: COc1ccc2nc(N3CCN(C4CC4)CC3)sc2c1 ; Cl]

A mixture of 2-chloro-6-methoxybenzothiazole (0.20 g, 1.0 mmol) and 1-cyclopropyl-piperazine (0.25 g, 2.0 mmol) was stirred at 120° C. overnight. The reaction mixture was allowed to cool and dissolved in a mixture of ethyl acetate a NaHCO$_3$ solution. The phases were separated and the organic phase was washed with water (3×) and then extracted with 0.25 M hydrochloric acid (20 mL). The acidic aqueous extract was concentrated and re-evaporated with ethanol. The residue was crystallized from a mixture of ethanol and ethyl acetate to give 60 mg (18%) of 2-(4-cyclopropylpiperazin-1-yl)-6-methoxybenzothiazole, hydrochloride.

$^1$H-NMR (400 MHz, DMSO-d$_6$) δ 11.3 (brs, 1H), 7.48 (d, 1H), 7.45 (d, 1H), 6.93 (dd, 1H), 4.18-4.06 (m, 2H), 3.89-3.75 (m, 5H), 3.68-3.52 (m, 2H), 3.44-3.33 (m, 2H), 2.94-2.86 (m, 1H), 1.21-1.15 (m, 2H), 0.85-0.79 (m, 2H).

Example 4

General Procedure A 2-(6-Methoxybenzothiazol-2-yl)octahydropyrido[1,2-a]pyrazine, hydrochloride

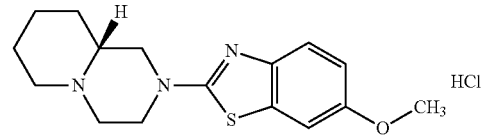 [SMILES: COc1ccc2nc(N3CCN4CCCC[C@@H]4C3)sc2c1 ; Cl]

A mixture of 2-chloro-6-methoxybenzothiazole (0.17 g, 1.0 mmol), octahydropyrido[1,2-a]-pyrazine (0.21 g, 1.0 mmol), DIPEA (0.51 mL) and dimethylsulfoxide (1 mL) was stirred at 115° C. overnight. The reaction mixture was allowed to cool and dissolved in a mixture of ethyl acetate and a NaHCO$_3$ solution. The phases were separated and the organic phase was washed with water (3×) and then extracted with 0.25 M hydrochloric acid (20 mL). The acidic aqueous extract was concentrated and re-evaporated with ethanol. The residue was crystallized from a mixture of ethanol and ethyl acetate to give 193 mg (57%) of 2-(6-methoxybenzothiazol-2-yl)octahydropyrido[1,2-a]pyrazine, hydrochloride.

$^1$H-NMR (400 MHz, DMSO-d$_6$) δ 11.2 (brs, 1H), 7.48 (d, 1H), 7.44 (d, 1H), 6.93 (dd, 1H), 4.15-4.08 (m, 2H), 3.77 (s, 3H), 3.71-3.62 (m, 1H), 3.46-3.32 (m, 4H), 3.24-3.13 (m, 1H), 3.02-2.91 (m, 1H), 1.98-1.76 (m, 4H), 1.70-1.58 (m, 1H), 1.54-1.42 (m, 1H).

Example 5

General Procedure B 2-(4-Isopropylpiperazin-1-yl)benzothiazole-6-carbonitrile

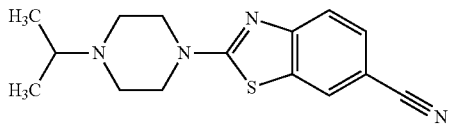 [SMILES: CC(C)N1CCN(c2nc3ccc(C#N)cc3s2)CC1]

Step A:

2-Chlorobenzothiazole-6-carbonitrile

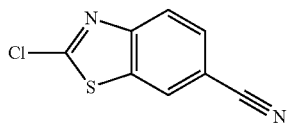 [SMILES: N#Cc1ccc2nc(Cl)sc2c1]

To a mixture of 4-aminobenzonitrile (23.6 g, 0.2 mol) and ammonium rhodanate (30.4 g, 0.4 mol) was added glacial acetic acid (600 mL) and the resulting solution was cooled to 13.5° C. on an ice-bath. A mixture of bromine and glacial acetic acid was added drop-wise and slowly. The resulting mixture was stirred for 1 hour at 13.5° C. and filtered. The filter cake was washed with glacial acetic (6×100 mL) and placed in hot water (1000 mL) with stirring. The mixture was filtered and pH of the filtrate was adjusted to 7 with a saturated sodium carbonate solution. The precipitate was isolated and dried to give 19.5 g (56%) of 2-amino-benzothiazole-6-carbonitrile. A mixture of concentrated hydrochloric acid (113 mL) and water (52 mL) was heated at 90° C. while 2-aminobenzothiazole-6-carbonitrile (19 g, 0.108 mol) was added. The mixture was cooled to −5° C. on an ice-bath and a solution of sodium nitrite (7.72 g, 0.112 mol) in water (20 mL) was added drop-wise, keeping the temperature below than 0° C. When addition was complete the mixture was stirred for 0.5 hour and a solution of $CuCl_2$ (16 g) in water (108 mL) was added drop-wise. When addition was complete the mixture was stirred for 10 min, and the ice-bath was removed. Stirring was continued for 2 h and the mixture was cooled to room temperature. The mixture was filtered and the solid was washed to neutrality with water and dried. This afforded 12.8 g (61%) of 2-chlorobenzothiazole-6-carbonitrile. $^1$H-NMR δ 8.14 (s, 1H), 8.03 (d, 1H), 7.75 (d, 1H).

Step B:

A solution of 2-chlorobenzothiazole-6-carbonitrile (14.9 g, 0.077 mol) in DMF (250 mL) was added drop-wise at 10° C. to a mixture of anhydrous piperazine (60 g, 0.698 mol) and DMF (300 mL). Then the mixture was stirred for 2 h. Water (1,550 mL) was added and the mixture was extracted with dichloromethane (5×500 mL). The combined organic extracts was washed with water (6×500 mL), dried ($Na_2SO_4$), filtered and evaporated to give a residue which was re-crystallised from ethyl acetate. This afforded 10.5 g (56%) of 2-(piperazin-1-yl)benzothiazole-6-carbonitrile. A mixture of this piperazine derivative (19.4 g, 0.08 mol), sodium iodide (1.94 g), triethylamine (9.6 g, 0.095 mol) and DMF (80 mL) was heated with stirring to give a red liquid. A solution of 2-bromopropane (14.7 g, 0.12 mol) in DMF (80 mL) was added drop-wise at 117° C. within in 1 h. The reaction mixture was stirred at 110-117° C. for another 3 h and then allowed to cool to room temperature. Water (110 mL) was added and the mixture was filtered. The filter cake was washed until the filtrate was colourless and then dried. The solid was dissolved in DMF (250 mL) and filtered to remove a solid residue. Water (1000 mL) was added to the filtrate with stirring to give a precipitate. The solid was isolated, washed with water and dried to give 9.4 g (41%) of 2-(4-Isopropylpiperazin-1-yl)-benzothiazole-6-carbonitrile.

$^1$H-NMR δ 8.25 (s, 1H), 7.61 (d, 1H), 7.45 (d, 1H), 3.55 (t, 4H), 2.68 (m, 1H), 2.51 (m, 4H), 0.93 (d, 6H).

Example 6

General Procedure D

[2-(4-Isopropylpiperazin-1-yl)benzothiazol-6-yl] piperidin-1-ylmethanone, trifluoroacetate

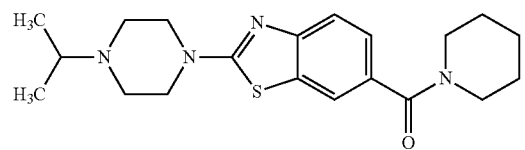

CF$_3$COOH

To a solution of 2-(4-isopropylpiperazin-1-yl)benzothiazole-6-carboxylic acid (800 mg, 2.1 mmol) in THF (14 mL) was added HOBt (342 mg, 2.5 mmol), EDAC (807 mg, 4.2 mmol), triethylamine (1.7 g, 17 mmol) and piperidine (718 mg, 8.5 mmol) at room temperature. The reaction mixture was stirred at 40-50° C. for 12 h under a nitrogen atmosphere. The mixture was concentrated in vacuo and the residue was purified by column chromatography on silica gel eluting with a gradient of $CH_2Cl_2$/MeOH (100:1->50:1) to give the crude product, which was further purified by preparative HPLC to give 167 mg (21%) of [2-(4-isopropylpiperazin-1-yl)benzothiazol-6-yl]piperidin-1-ylmethanone as a trifluoroacetate salt.

$^1$NMR (300 MHz, $D_2O$) δ 7.64 (d, 1H), 7.43 (d, 2H), 7.28 (dd, 1H), 4.08-4.28 (m, 2H), 3.42-3.62 (m, 7H), 3.08-3.35 (m, 4H), 1.48-1.59 (m, 4H), 1.36-1.40 (m, 2H), 1.23 (d, 6H).

Example 7

General Procedure D 2-(4-Isopropylpiperazin-1-yl)benzothiazole-6-carboxylic acid dimethylamide, trifluoroacetate

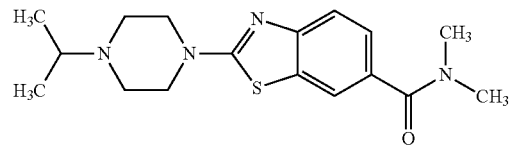

CF$_3$COOH

To a solution of 2-(4-isopropylpiperazin-1-yl)benzothiazole-6-carboxylic acid (800 mg, 2.1 mmol) in THF (14 mL) was added HOBt (342 mg, 2.5 mmol), EDAC (807 mg, 4.2 mmol), triethylamine (1.7 g, 17 mmol) and dimethylamine hydrochloride (689 mg, 8.5 mmol) at room temperature. The reaction mixture was stirred at 40-50° C. for 12 h under a nitrogen atmosphere. The mixture was concentrated in vacuo and the residue was purified by column chromatography on silica gel with a gradient of CH$_2$Cl$_2$/MeOH (100:1->50:1) as eluent to give the crude product, which was further purified by preparative HPLC to give 178 mg (25%) of [2-(4-Isopropylpiperazin-1-yl)benzothiazol-6-carboxylic acid dimethylamide as a trifluoroacetate salt.

$^1$H NMR (300 MHz, D$_2$O) δ 7.66 (d, 1H), 7.42 (d, 2H), 7.32 (dd, 1H), 4.08-4.22 (m, 2H), 3.42-3.65 (m, 5H), 3.11-3.28 (m, 2H), 2.92 (s, 3H), 2.83 (s, 3H), 1.21 (d, 6H),

Example 8

General Procedure D

[2-(4-Isopropylpiperazin-1-yl)benzothiazol-6-yl]morpholin-4-ylmethanone, trifluoroacetate

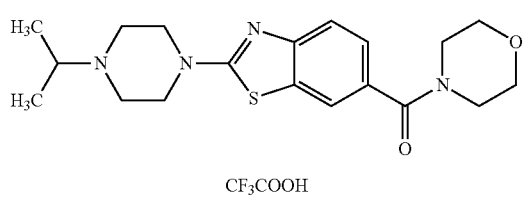

CF$_3$COOH

To a solution of 2-(4-isopropylpiperazin-1-yl)benzothiazole-6-carboxylic acid (800 mg, 2.1 mmol) in THF (14 mL) was added HOBt (342 mg, 2.5 mmol), EDAC (807 mg, 4.2 mmol), triethylamine (1.7 g, 17 mmol) and morpholine (735 mg, 8.4 mmol) at room temperature. The reaction mixture was stirred at 40-50° C. for 12 h under a nitrogen atmosphere. The mixture was concentrated in vacuo and the residue was purified by column chromatography on silica gel with a gradient of CH$_2$Cl$_2$/MeOH (100:1->50:1) as eluent to give the crude product, which was further purified by preparative HPLC to give 224 mg (28%) of [2-(4-isopropyl-piperazin-1-yl)benzothiazol-6-yl]morpholin-4-ylmethanone as a trifluoroacetate salt.

$^1$NMR (300 MHz, D$_2$O) δ 7.64 (s, 1H), 7.40 (d, 2H), 7.29 (dd, 1H), 4.02-4.23 (m, 2H), 3.49-3.69 (m, 11H), 3.35-3.49 (m, 2H), 3.07-3.28 (m, 2H), 1.19 (s, 6H)

Example 9

General Procedure E 2-(4-Isopropylpiperazin-1-yl)-6-piperidin-1-ylmethylbenzothiazole

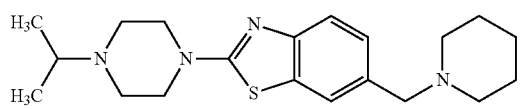

Step A:

2-(4-Isopropylpiperazin-1-yl)benzothiazole-6-carboxalhyde

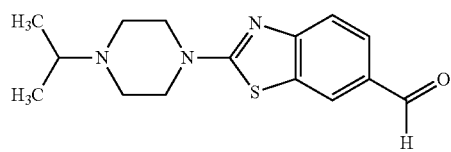 [SMILES: CC(C)N1CCN(c2nc3ccc(C=O)cc3s2)CC1]

To a solution of 2-(4-isopropylpiperazin-1-yl)benzothiazole-6-carbonitrile (5.0 g, 0.0175 mol) in THF (150 mL) at −78° C., DIBAL-H (175 mL, 0.0175 mol) was added dropwise. After the addition, the mixture was allowed to warm to −40° C. and was stirred for one hour at that temperature. A mixture of H$_2$O/THF (1:4, 250 mL) was added dropwise. The mixture was allowed to warm to room temperature and then filtered. The volatiles were evaporated from the filtrate. The residue was purified by column chromatography on silica gel, eluting with CH$_2$Cl$_2$/MeOH (20:1), to give 2.5 g (49%) of 2-(4-isopropylpiperazin-1-yl)benzothiazole-6-carboxaldehyde.

$^1$H NMR (300 MHz, CDCl$_3$) δ 1.10 (d, 6H), 2.69 (t, 4H), 2.81-2.85 (M, 1H), 3.74 (t, 4H), 7.58 (d, 1H), 7.79 (dd, 1H), 8.12 (d, 1H), 9.92 (s, 1H).

Step B:

To a solution of 2-(4-isopropylpiperazin-1-yl)benzothiazole-6-carboxaldehyde (0.5 g, 1.73 mmol) and AcOH (11 mg, 0.173 mmol) in THF (5 mL), piperazine (0.34 ml, 3.46 mmol) and NaCNBH$_3$ (132 mg, 2.08 mmol) were added in turn. The reaction mixture was heated at 63° C. for 12 hours. The solvent was removed and the mixture was extracted with ethyl acetate, washed with water and brine and dried (MgSO$_4$). The volatiles were evaporated and the residue was purified by column chromatography on silica gel, eluting with ethyl acetate and methanol (10:1) to yield 160 mg (26%) of 2-(4-isopropylpiperazin-1-yl)-6-piperidin-1-yl-methylbenzothiazole.

$^1$NMR (300 MHz, CD$_3$OD) δ 1.10 (d, 6H), 1.59 (m, 2H), 1.72-1.76 (m, 4H), 2.70 (t, 4H), 2.72-2.79 (m, 1H), 2.92 (brs, 4H), 3.65 (t, 4H), 4.03 (s, 2H), 7.35 (dd, 1H), 7.49 (d, 1H), 7.75 (s, 1H).

Example 10

General Procedure E 2-(4-Isopropylpiperazin-1-yl)-6-(morpholin-4-ylmethyl)benzothiazole, trifluoroacetate

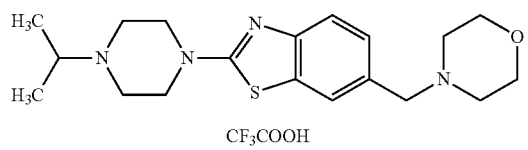 [SMILES: CC(C)N1CCN(c2nc3ccc(CN4CCOCC4)cc3s2)CC1 ; "CF3COOH"]

CF$_3$COOH

To a solution of 2-(4-isopropylpiperazin-1-yl)benzothiazole-6-carboxaldehyde (0.5 g, 1.73 mmol) and AcOH (11 mg, 0.173 mmol) in THF (5 mL), morpholine (0.31 mL, 3.46 mmol) and NaCNBH$_3$ (132 mg, 2.08 mmol) were added in turn. The reaction mixture was heated at 63° C. for 12 hours. The solvent was removed and the residue was extracted with ethyl acetate, washed with water and brine and dried (MgSO₄). The volatiles were evaporated and the residue was purified by preparative HPLC to yield 130 mg (21%) of 2-(4-isopropylpiperazin-1-yl)-6-(morpholin-4-ylmethyl) benzothiazole as a trifluoroacetate salt.

¹H NMR (300 MHz, D₂O) δ 1.25 (d, 6H), 3.07-3.32 (m, 6H), 3.49-3.66 (m, 7H), 3.96 (d, 2H), 4.20 (d, 2H), 4.31 (s, 2H), 7.37 (dd, 1H), 7.49 (d, 1H), 7.75 (s, 1H).

Example 11

General Procedure E

[2-(4-Isopropylpiperazin-1-yl)benzothiazol-6-ylmethyl]dimethylamine, trifluoroacetate

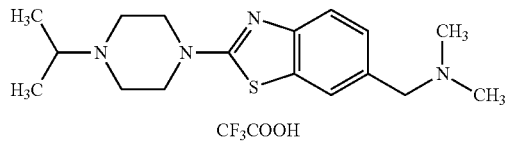

CF₃COOH

To a solution of 2-(4-isopropylpiperazin-1-yl)benzothiazole-6-carboxaldehyde (0.7 g, 2.42 mmol) and AcOH (291 mg, 4.84 mmol) in THF, dimethylamine hydrochloride (397 mg, 4.84 mmol) and NaCNBH₃ (245 mg, 3.88 mmol) were added in turn. The reaction mixture was heated at 63° C. for 12 hours. The solvent was removed and the residue was extracted with ethyl acetate, washed with water and brine and dried (MgSO₄). The volatiles were evaporated and the residue was purified by preparative HPLC to yield 250 mg (32%) of [2-(4-isopropylpiperazin-1-yl)benzothiazol-6-ylmethyl] dimethylamine as a trifluoroacetate salt.

¹H NMR (300 MHz, D₂O) δ 1.22 (d, 6H), 2.69 (s, 6H), 3.12-3.22 (m, 2H), 3.47-3.51 (m, 5H), 4.14-4.20 (m, 4H), 7.32 (dd, 1H), 7.46 (d, 1H), 7.71 (s, 1H).

Example 12

General Procedure F 2-(4-Isopropylpiperazin-1-yl)-6-(5-methyl-[1,2,4]oxadiazol-3-yl)benzothiazole, trifluoroacetate

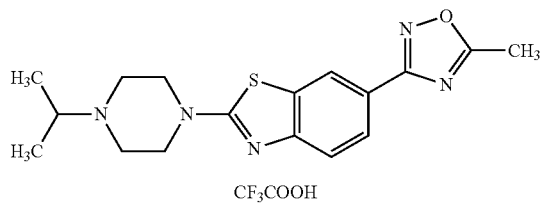 [SMILES: Cc1nc(-c2ccc3nc(N4CCN(C(C)C)CC4)sc3c2)no1 ; "CF3COOH"]

CF₃COOH

Step A:

N-hydroxy-2-(4-isopropylpiperazin-1-yl)benzothiazole-6-carboxamidine

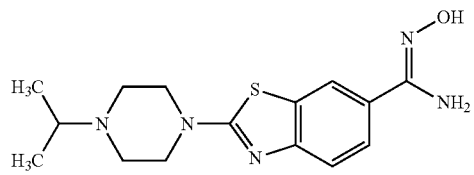 [SMILES: CC(C)N1CCN(c2nc3ccc(/C(N)=N/O)cc3s2)CC1]

To a solution of 2-(4-isopropylpiperazin-1-yl)benzothiazole-6-carbonitrile (5.0 g, 17.5 mmol) in ethanol (50 mL) was added hydroxylamine hydrochloride (3.6 g, 52.4 mmol), water (8 mL) and potassium carbonate (7.2 g, 52.4 mmol). The reaction mixture was heated overnight at reflux. The mixture was allowed to cool and then concentrated in vacuo. The residue was dissolved into THF (30 mL) and then filtered. The filtrate was concentrated in vacuo to give 4 g of crude N-hydroxy-2-(4-isopropylpiperazin-1-yl)benzothiazole-6-carboxamidine.

¹H NMR (300 MHz, DMSO-d₆): δ 9.50 (s, 1H), 7.98 (s, 1H), 7.55 (d, 1H), 7.36 (d, 1H), 5.73 (s, 2H), 3.47-3.52 (m, 4H), 2.61-2.72 (m, 1H), 2.49-2.59 (m, 4H), 0.94 (d, 6H).

Step B:

A solution of N-hydroxy-2-(4-isopropylpiperazin-1-yl) benzothiazole-6-carboxamidine (700 mg, 2.19 mmol) in acetic anhydride (20 mL) was heated at 130° C. for 6 h. The solvent was removed under reduced pressure and the residue was purified by preparative HPLC to give 125 mg (16.7%) of 2-(4-isopropylpiperazin-1-yl)-6-(5-methyl-[1,2,4]oxadiazol-3-yl)benzo-thiazole as a trifluoroacetate salt.

¹H NMR (400 MHz, CD₃OD) δ 8.38 (s, 1H), 8.01 (dd, 1H), 7.62 (d, 1H), 4.21-4.59 (m, 2H), 3.31-3.83 (m, 7H), 2.64 (s, 3H), 1.42 (d, 6H).

Example 13

General Procedure F 2-(4-Isopropylpiperazin-1-yl)-6-(5-phenyl-[1,2,4]oxadiazol-3-yl)benzothiazole

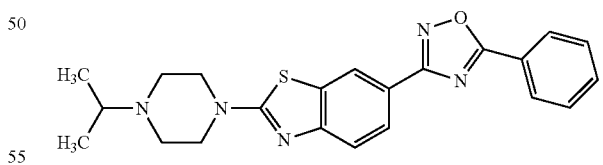

To a solution of N-hydroxy-2-(4-isopropylpiperazin-1-yl) benzothiazole-6-carboxamidine (650 mg, 2.04 mmol) in acetic acid (40 mL) was added benzoylchloride (3 mL). The reaction mixture was stirred overnight at room temperature and then refluxed for 2 h. The reaction mixture was concentrated in vacuo and the residue was dissolved into 0.5 N hydrochloric acid (30 mL). The aqueous solution was extracted with diethyl ether (3×15 mL). The organic layer was discarded and the aqueous phase was basified to pH 13 with 4 N sodium hydroxide and then extracted with ethyl acetate (4×10 mL). The combined organic extracts were evaporated and the residue was recrystallized three times from a mixture of $CH_2Cl_2$ and MeOH to give 189 mg (26%) of 2-(4-isopropylpiperazin-1-yl)-6-(5-phenyl-[1,2,4]oxadiazol-3-yl)benzothiazole.

$^1$H NMR (300 MHz, CDCl$_3$) δ 8.41 (s, 1H), 8.21 (d, 2H), 8.11 (d, 1H), 7.48-7.72 (m, 4H), 3.57-3.82 (m, 4H), 2.70-2.92 (m, 1H), 2.53-2.70 (m, 4H), 1.08 (d, 6H).

Example 14

General Procedure F 2-(4-Isopropylpiperazin-1-yl)-6-(5-pyridin-4-yl-[1,2,4]oxadiazol-3-yl)benzothiazole

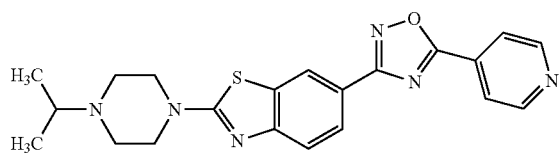 [SMILES: CC(C)N1CCN(c2nc3ccc(-c4noc(-c5ccncc5)n4)cc3s2)CC1]

To a solution of N-hydroxy-2-(4-isopropylpiperazin-1-yl)benzothiazole-6-carboxamidine (1.30 g, 4.07 mmol) in acetic acid (50 mL) was added isonicotinoyl chloride (1.42 g, 10.0 mmol). The reaction mixture was stirred overnight at room temperature and then heated at refluxed for 8 h. The reaction mixture was concentrated in vacuo and the residue was dissolved into 0.5 N hydrochloric acid (40 mL). The aqueous solution was extracted with diethyl ether (3×15 mL). The organic extracts were discarded and the aqueous phase was basified to pH 13 with 4 N sodium hydroxide and then extracted with ethyl acetate (4×10 mL). The combined organic extracts were evaporated and the residue was recrystallized from a mixture of $CH_2Cl_2$ and MeOH to give 175 mg (11%) of 2-(4-isopropylpiperazin-1-yl)-6-(5-pyridin-4-yl-[1,2,4]oxadiazol-3-yl)benzothiazole.

$^1$H NMR (300 MHz, CDCl$_3$) δ 8.88 (dd, 2H), 8.41 (d, 1H), 8.03-8.12 (m, 3H), 7.62 (d, 1H), 3.70 (t, 4H), 2.72-2.87 (m, 1H), 2.67 (t, 4H), 1.08 (d, 6H).

Example 15

General Procedure G 2-(4-Cyclopentylpiperazin-1-yl)benzothiazole-6-carbonitrile

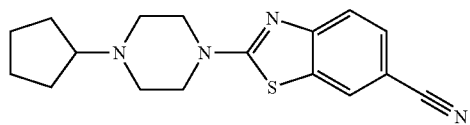 [SMILES: N#Cc1ccc2nc(N3CCN(C4CCCC4)CC3)sc2c1]

Step A:

6-Bromo-2-(4-cyclopentylpiperazin-1-yl)benzothiazole

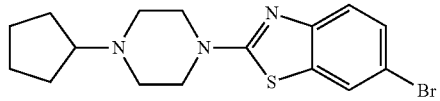 [SMILES: Brc1ccc2nc(N3CCN(C4CCCC4)CC3)sc2c1]

To a solution of 6-bromo-2-chlorobenzothiazole (3 g, 12.1 mmol) in ethanol (50 mL) was added triethylamine (5.04 mL, 36.3 mmol) and 1-cyclopentylpiperazine (1.86 g, 12.1 mmol). The reaction mixture was heated at reflux for 16 h and then concentrated under reduced pressure. The residue was extracted with ethyl acetate and the combined organic extracts were washed with brine, dried (Na$_2$SO$_4$) and concentrated under reduced pressure to afford 4.3 g (99%) of 6-bromo-2-(4-cyclopentylpiperazin-1-yl)benzothiazole.

Step B:

To a solution of 6-bromo-2-(4-cyclopentylpiperazin-1-yl)benzothiazole (0.54 g, 1.50 mmol) in N-methylpyrrolidin-2-one (100 mL) was added copper(I)iodide (344 mg, 1.80 mmol) and copper(I)cyanide (270 mg, 3.0 mmol). The mixture was heated at 160° C. for 4 h, then allowed to cool to room temperature and filtered. The filtercake was washed with ethyl acetate and the filtrate was extracted with ethyl acetate. The combined organic extracts were washed with brine, dried (Na$_2$SO$_4$) and concentrated under reduced pressure. The residue was purified by preparative HPLC to afford 140 mg (30%) of 2-(4-cyclopentylpiperazin-1-yl)benzothiazole-6-carbonitrile.

$^1$H NMR (300 MHz, CDCl$_3$) δ 7.86 (s, 1H), 7.55 (d, 2H), 3.85-3.75 (t, 4H), 2.82-2.64 (m, 5H), 1.95-1.55 (m, 8H).

Example 16

General Procedure E

[2-(4-Cyclopropylpiperazin-1-yl)benzothiazol-6-ylmethyl]dimethylamine, trifluoroacetate

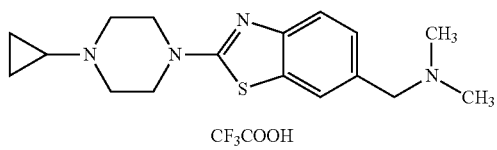 [SMILES: CN(C)Cc1ccc2nc(N3CCN(C4CC4)CC3)sc2c1 ; "CF3COOH"]

To a solution of 2-(4-cyclopropylpiperazin-1-yl)benzothiazole-6-carboxaldehyde (500 mg, 1.7 mmol) in methanol (14 mL) and THF (28 mL) was added dimethylamine hydrochloride (277 mg, 3.4 mmol), acetic acid (22 mg, 0.4 mmol) and NaCNBH$_3$ (158 mg, 2.7 mmol). The mixture was stirred at 63° C. overnight. Then the resulting mixture was concentrated under reduced pressure and the residue was diluted with dichloromethane (15 mL). The mixture was washed with brine and the organic phase was dried (MgSO$_4$) and concentrated under reduced pressure. The residue was purified by preparative HPLC to give 367 mg (32%) of [2-(4-cyclopropylpiperazin-1-yl)benzothiazol-6-ylmethyl]dimethyl-amine as a trifluoroacetate salt.

¹H NMR (300 MHz, D₂O). δ 7.75 (d, 1H), 7.50 (d, 1H), 7.36 (dd, 2H), 4.24 (s, 2H), 4.15-3.15 (m, 8H), 2.85-2.75 (m, 1H), 2.73 (s, 6H), 0.98-0.88 (m, 4H).

Example 17

General Procedure E 2-(4-Cyclopropylpiperazin-1-yl)-6-(pyrrolidin-1-ylmethyl)benzothiazole, trifluoroacetate

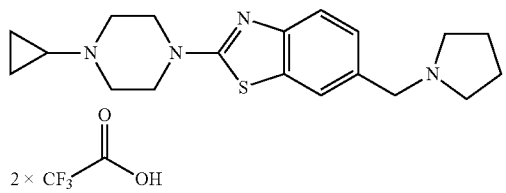

To a solution of 2-(4-cyclopropylpiperazin-1-yl)benzothiazole-6-carboxaldehyde (500 mg, 1.7 mmol) in MeOH (14 mL) and THF (28 mL) was added pyrrolidine (242 mg, 3.4 mmol), acetic acid (22 mg, 0.4 mmol) and NaCNBH₃ (158 mg, 2.7 mmol). The mixture was stirred at 63° C. overnight. Then the mixture was concentrated under reduced pressure and dichloromethane (15 mL) was added. The mixture was washed with brine and the organic phase was dried (MgSO₄) and concentrated under reduced pressure. The residue was purified by preparative HPLC to give 318 mg (27%) of 2-(4-cyclopropylpiperazin-1-yl)-6-(pyrrolidin-1-ylmethyl)-benzothiazole as a trifluoroacetate salt.

¹H NMR (400 MHz, D₂O). δ 7.80 (s, 1H), 7.53 (d, 1H), 7.42 (d, 1H), 4.34 (s, 2H), 4.30-3.48 (m, 8H), 3.48-3.35 (m, 2H), 3.19-3.05 (m, 2H), 2.90-2.80 (m, 1H), 2.15-1.97 (m, 2H), 1.97-1.80 (m, 2H), 1.05-0.88 (m, 4H).

HPLC (Method B): t_r=2.02 min (97.9%).

Example 18

General Procedure E 2-(4-Cyclopropylpiperazin-1-yl)-6-(morpholin-4-ylmethyl)benzothiazole, trifluoroacetate

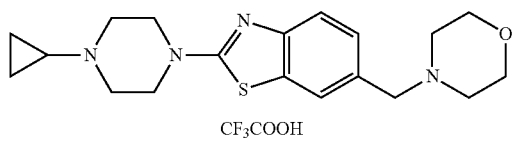

To a solution of 2-(4-cyclopropylpiperazin-1-yl)benzothiazole-6-carboxaldehyde (500 mg, 1.7 mmol) in MeOH (14 mL) and THF (28 mL) was added morpholine (296 mg, 3.4 mmol), acetic acid (22 mg, 0.4 mmol) and NaCNBH₃ (158 mg, 2.7 mmol). The mixture was stirred at 63° C. overnight. Then the resulting mixture was concentrated under reduced pressure and the residue was diluted with dichloromethane (15 mL). The mixture was washed with brine, dried (MgSO₄) and concentrated under reduced pressure. The residue was purified by preparative HPLC to give 306 mg (31%) of 2-(4-cyclopropylpiperazin-1-yl)-6-(morpholin-4-ylmethyl)benzothiazole as a trifluoroacetate salt.

¹H NMR (300 MHz, D₂O). δ 7.75 (d, 1H), 7.49 (d, 1H), 7.37 (dd, 1H), 4.30 (s, 2H), 4.20-3.40 (m, 12H), 3.35-3.25 (m, 2H), 3.18-3.02 (m, 2H), 2.85-2.75 (m, 1H), 0.98-0.88 (m, 4H).

HPLC (Method B): t_r=2.70 min (95.1%).

Example 19

General Procedure E 2-(4-Cyclopropylpiperazin-1-yl)-6-(piperidin-1-ylmethyl)benzothiazole, trifluoroacetate

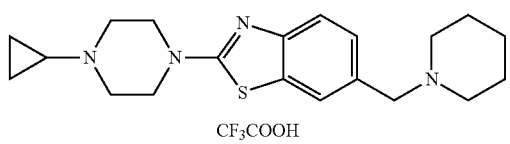 [SMILES: c1cc2nc(N3CCN(C4CC4)CC3)sc2cc1CN1CCCCC1 ; "CF3COOH"]

Step A:

2-(4-Cyclopropylpiperazin-1-yl)benzothiazole-6-carbonitrile

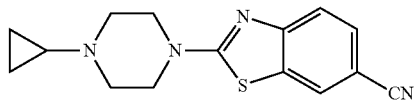 [SMILES: N#Cc1ccc2nc(N3CCN(C4CC4)CC3)sc2c1]

A suspension of 2-chlorobenzothiazole-6-carbonitrile (3.5 g, 18 mmol), 1-cyclopropyl-piperazine (3.63 g, 28.8 mmol) and ammonium chloride (0.96 g, 18 mmol) in butan-1-ol (112 mL) was heated at reflux for 48 h. The solvent was removed under reduced pressure and the residue was diluted with water (30 mL). The mixture was made alkaline with potassium carbonate and extracted with CH₂Cl₂ (3×20 mL). The combined organic extracts were concentrated to give a residue which was purified by column chromatography on silica gel (20% ethyl acetate in petroleum ether) to give 2.2 g (43 5) of 2-(4-cyclopropylpiperazin-1-yl)-benzothiazole-6-carbonitrile.

Step B:

2-(4-Cyclopropylpiperazin-1-yl)benzothiazole-6-carbaldehyde

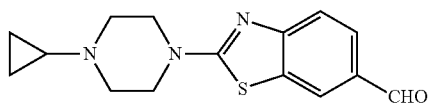 [SMILES: O=Cc1ccc2nc(N3CCN(C4CC4)CC3)sc2c1]

To a solution of 2-(4-cyclopropylpiperazin-1-yl)benzothiazole-6-carbonitrile (2 g, 7 mmol) in toluene was added DIBAH (15.5 mL, 15.5 mmol, 1M in toluene) dropwise at room temperature and stirring was continued for 1 h at room temperature. The reaction mixture was quenched with H₂SO₄ (5% solution in water). The mixture was filtered and the filtrate was extracted with ethyl acetate (3×20 mL). The combined organic extracts were concentrated to give 1.7 g (85%) of 2-(4-cyclopropylpiperazin-1-yl)benzothiazole-6-carboxaldehyde.

¹H NMR (300 MHz, CDCl₃) δ 9.92 (s, 1H), 8.12 (d, 1H), 7.79 (dd, 1H), 7.57 (d, 1H), 3.66 (t, 4H), 2.75 (t, 4H), 1.75-1.65 (m, 1H), 0.55-0.40 (m, 4H).

Step C:

To a solution of 2-(4-cyclopropylpiperazin-1-yl)benzothiazole-6-carboxaldehyde (500 mg, 1.7 mmol) in MeOH (14 mL) and THF (28 mL) was added piperidine (290 mg, 3.4 mmol), acetic acid (22 mg, 0.4 mmol) and NaCNBH₃ (158 mg, 2.7 mmol). The mixture was stirred at 63° C. overnight. The reaction mixture was concentrated under reduced pressure and CH₂Cl₂ (15 mL) was added to the residue. The mixture was washed with brine, dried (MgSO₄) and concentrated under reduced pressure. The residue was purified by preparative HPLC to give 332 mg (28%) of 2-(4-cyclopropylpiperazin-1-yl)-6-(piperidin-1-ylmethyl)benzothiazole as a trifluoroacetate salt.

¹H NMR (400 MHz, D₂O) δ 7.84 (s, 1H), 7.57 (d, 1H), 7.50 (d, 1H), 4.28 (s, 2H), 4.24-3.50 (m, 8H), 3.45-3.32 (m, 2H), 2.98-2.80 (m, 3H), 1.95-1.80 (m, 2H), 1.80-1.70 (m, 1H), 1.70-1.52 (m, 2H), 1.49-1.30 (m, 1H), 1.10-0.90 (m, 4H).

HPLC (Method B): t,=2.78 min (99%).

Example 20

General Procedure H

N-[2-(4-Cyclopropylpiperazin-1-yl)benzothiazol-6-yl]-acetamide, trifluoroacetate

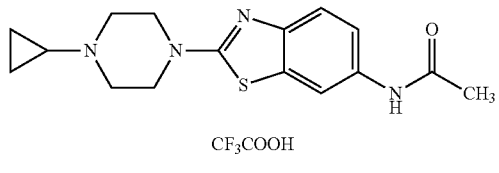 [SMILES: CC(=O)Nc1ccc2nc(N3CCN(C4CC4)CC3)sc2c1 ; "CF3COOH"]

CF₃COOH

Step A:

6-Bromo-2-(4-cyclopropylpiperazin-1-yl)benzothiazole

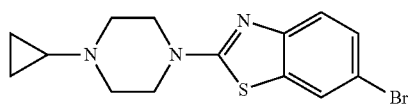 [SMILES: Brc1ccc2nc(N3CCN(C4CC4)CC3)sc2c1]

To a solution of 6-bromo-2-chlorobenzothiazole (8.2 g, 33 mmol) in EtOH (115 mL) was added Et₃N (16.7 g, 165 mmol), followed by 1-cyclopropylpiperazine (5 g, 39.6 mmol). The mixture was heated at reflux for 12 h. Then the mixture was evaporated to remove EtOH. Water (120 mL) was added to the residue and the mixture was extracted with CH₂Cl₂ (3×50 mL). The combined organic extracts were washed with brine, dried (Na₂SO₄) and concentrated to give a residue, which was purified by column chromatography on silica gel eluting with a mixture of EtOAc/petroleum ether (1:10 with 0.1% NH₄OH added) to give 3.46 g (31%) 6-bromo-2-(4-cyclopropylpiperazin-1-yl)benzothiazole.

¹H NMR (300 MHz, CDCl₃): δ 7.70 (t, 1H), 7.38 (dd, 2H), 3.60 (d, 4H), 2.80 (d, 4H), 1.68 (d, 1H), 0.50-0.39 (m, 4H).

Step B:

A mixture of 6-bromo-2-(4-cyclopropylpiperazin-1-yl)benzothiazole (480 mg, 1.42 mmol), acetamide (251 mg, 4.26 mmol), Pd(OAc)₂ (15.9 mg, 0.071 mmol), Cs₂CO₃ (694 mg, 2.13 mmol) and xantphos (62 mg, 0.107 mmol) in 1,4-dioxane (10 mL) was heated at reflux for 12 h. Water (5 mL) was added and the mixture was filtered. The filtrate was extracted with EtOAc (3×5 mL). The combined organic extracts were washed with brine, dried (Na₂SO₄) and concentrated to give a residue, which was purified by the preparative HPLC to give 108 mg (24%) of N-[2-(4-cyclopropylpiperazin-1-yl)benzothiazol-6-yl]acetamide as a trifluoroacetate salt.

¹H NMR (300 MHz, D₂O): δ 7.82 (s, 1H), 7.40 (d, 1H), 7.28 (d, 1H), 4.20-3.30 (m, 8H), 2.81-2.78 (m, 1H), 2.02 (s, 3H), 0.91-0.89 (d, 4H).

HPLC (Method B): t,=3.60 min (95.4%).

Example 21

General Procedure D

[2-(4-Cyclopropylpiperazin-1-yl)benzothiazol-6-yl]-(4-methylpiperazin-1-yl)methanone, trifluoroacetate

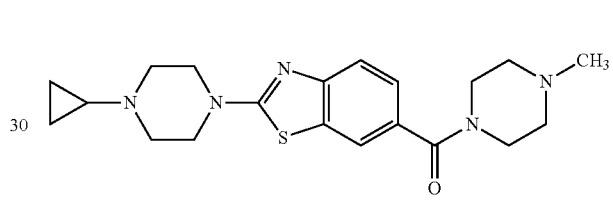

CF₃COOH

Step A:

2-(4-Cyclopropylpiperazin-1-yl)benzothiazole-6-carboxylic acid

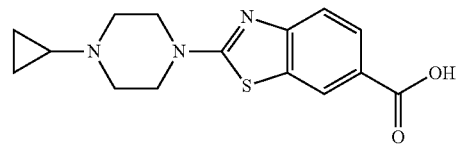 [SMILES: O=C(O)c1ccc2nc(N3CCN(C4CC4)CC3)sc2c1]

A mixture of 2-(4-cyclopropylpiperazin-1-yl)benzothiazole-6-carbonitrile (500 mg, 1.7 mmol) and concentrated HCl (5 mL) was heated at reflux overnight. The solvent was removed under reduced pressure to give crude 2-(4-cyclopropylpiperazin-1-yl)benzothiazole-6-carboxylic acid.

Step B:

To a suspension of 2-(4-cyclopropylpiperazin-1-yl)benzothiazole-6-carboxylic acid (530 mg, 1.76 mmol), 1-methylpiperazine (350 mg, 3.54 mmol) and DIEA (0.92 mL, 5.28 mmol) in DMF was added PyBop (1.8 g, 3.52 mmol). The resulting solution was stirred overnight at rt. The solvent was removed under reduced pressure and the residue was diluted with water and dichloromethane. The phases were separated and the organic phase was dried (Na₂SO₄) and concentrated to give the crude product, which was purified by preparative HPLC. This afforded 296 mg (20%) of give [2-(4-cyclopropylpiperazin-1-yl)benzothiazol-6-yl]-(4-methylpiperazin-1-yl)methanone as a trifluoroacetate salt.

$^1$H NMR (400 MHz, CD$_3$OD): δ 7.78 (s, 1H), 7.51 (d, 1H), 7.38 (d, 1H), 3.89-3.49 (m, 8H), 2.78 (t, 4H), 2.58-2.38 (m, 4H), 2.32 (s, 3H), 1.79-1.62 (m, 1H), 0.58-0.42 (m, 4H).
HPLC (Method B): t$_r$=5.27 min (95.9%).

Example 22

General Procedure I 2-(4-Cyclopropylpiperazin-1-yl)-6-(3,4-dimethoxyphenyl)benzothiazole

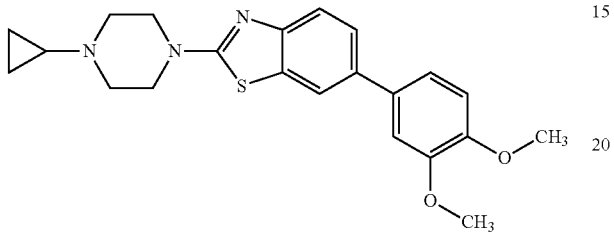

To a solution of 6-bromo-2-(4-cyclopropylpiperazin-1-yl) benzothiazole (500 mg, 1.48 mmol) and 3,4-dimethoxyphenylboronic acid (323 mg, 1.78 mmol) in THF—H$_2$O (20 mL, 5:1) was added Pd$_2$(dba)$_3$ (240 mg, 0.148 mmol), followed by P(t-Bu)$_3$BF$_4$ (86 mg, 0.296 mmol) and K$_3$PO$_4$.H$_2$O (1.97 g, 7.4 mmol). The mixture was heated at 60° C. for 3 h. The mixture was filtered and the filtrate was evaporated. the residue was diluted with water (5 mL) and extracted with CH$_2$Cl$_2$ (3×5 mL). The combined organic extracts were dried (Na$_2$SO$_4$) and concentrated to give the crude product, which was purified by column chromatography on silica gel eluting with CH$_2$Cl$_2$/MeOH (1:50). This afforded 258 mg (49%) of 2-(4-cyclopropyl-piperazin-1-yl)-6-(3,4-dimethoxybenzo)benzothiazole.
$^1$H NMR (400 MHz, CD$_3$OD): δ 7.78 (s, 1H), 7.58 (d, 1H), 7.48 (d, 1H), 7.16-7.11 (m, 2H), 6.94 (d, 1H), 3.96 (s, 3H), 3.93 (s, 3H), 3.63 (t, 4H), 2.76 (t, 4H), 1.69 (m, 1H), 0.52 (m, 4H).
HPLC (Method B): t$_r$=5.71 min (96.5%).

Example 23

General Procedure I 2-(4-Cyclopropylpiperazin-1-yl)-6-(6-methoxypyridin-3-yl)benzothiazole

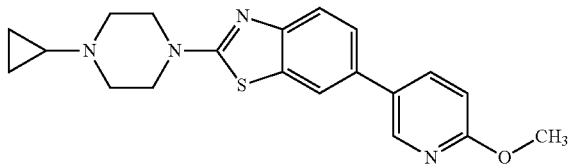 [SMILES: COc1ccc(-c2ccc3nc(N4CCN(C5CC5)CC4)sc3c2)cn1]

To a solution of 6-bromo-2-(4-cyclopropylpiperazin-1-yl) benzothiazole (400 mg, 1.18 mmol) and 2-methoxy-5-pyridineboronic acid (217 mg, 1.42 mmol) in THF—H$_2$O (16 mL, 5:1) was added Pd$_2$(dba)$_3$ (191 mg, 0.118 mmol), followed by P(t-Bu)$_3$BF$_4$ (68 mg, 0.236 mmol) and K$_3$PO$_4$.H$_2$O (1.57 g, 5.9 mmol). The mixture was heated to 60° C. for 3 h. The mixture was filtered and the filtrate was evaporated. the residue was diluted with water (5 mL) and extracted with CH$_2$Cl$_2$ (3×5 mL). The combined organic extracts were dried (Na$_2$SO$_4$) and concentrated to give the crude product, which was purified by column chromatography on silica gel eluting with CH$_2$Cl$_2$/MeOH (1:50). This afforded 253 mg (58%) of 2-(4-cyclopropyl-piperazin-1-yl)-6-(6-methoxypyridin-3-yl)benzothiazole.
$^1$H NMR (300 MHz, CDCl$_3$): δ 8.38 (d, 1H), 7.80 (dd, 1H), 7.74 (d, 1H), 7.59 (d, 1H), 7.46 (d, 1H), 6.81 (d, 1H), 3.98 (s, 3H), 3.646 (m, 4H), 2.77 (m, 4H), 1.61 (m, 1H), 0.50 (m, 4H).
HPLC (Method B): t$_r$=4.12 min (96.5%).

Example 24

General Procedure I 6-(5-Chloro-2-methoxypyridin-4-yl)-2-(4-cyclopropylpiperazin-1-yl)benzothiazole, trifluoroacetate

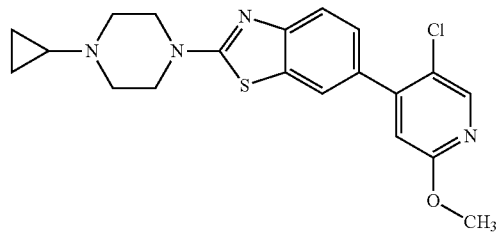

CF$_3$COOH

To a solution of 6-bromo-2-(4-cyclopropylpiperazin-1-yl) benzothiazole (500 mg, 1.48 mmol) and 5-chloro-2-methoxypyridin-4-yl-4-boronic acid (334 mg, 1.78 mmol) in DMF (20 mL) was added PdCl$_2$(dppf) (108 mg, 0.148 mmol), followed by CH$_3$COOK (581 mg, 5.92 mmol). The mixture was heated at 80° C. for 2 h, filtered and the volatiles evaporated. Water (5 mL) was added and the mixture was extracted with CH$_2$Cl$_2$ (3×5 mL). The combined organic extracts were dried (Na$_2$SO$_4$) and concentrated. The residue was purified by the preparative HPLC to give 35 mg (6%) of 6-(5-chloro-2-methoxypyridin-4-yl)-2-(4-cyclopropylpiperazin-1-yl)benzothiazole as a trifluoroacetate salt.
$^1$H NMR (300 MHz, D$_2$O): δ 7.99 (s, 1H), 7.61 (s, 1H), 7.37 (d, 2H), 6.58 (s, 1H), 4.00-3.40 (m, 11H), 2.82-2.67 (m, 1H), 1.03-0.83 (m, 4H).
HPLC (Method B): t$_r$=4.83 min (98.5%).

Example 25

General Procedure E 2-(6-Piperidin-1-ylmethylbenzothiazol-2-yl)octahydro-pyrido[1,2-a]pyrazine, trifluoroacetate

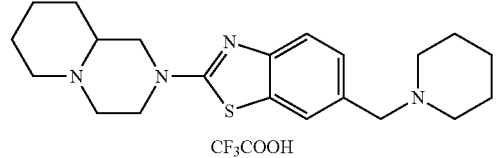 [SMILES: c1cc2nc(N3CCN4CCCCC4C3)sc2cc1CN1CCCCC1 ; "CF3COOH"]

CF$_3$COOH $^1$H NMR (300 MHz, D$_2$O): δ 7.76 (d, 1H), 7.51 (d, 1H), 7.39 (dd, 1H), 4.30-4.10 (m, 4H), 3.70-3.20 (m, 8H), 3.05-2.75 (m, 3H), 2.00-1.25 (m, 12H).
HPLC (Method B): t$_r$=2.90 min (98.8%).

Example 26

General Procedure I

N-{4-[2-(4-Cyclopropylpiperazin-1-yl)benzothiazol-6-yl]phenyl}-acetamide, trifluoroacetate

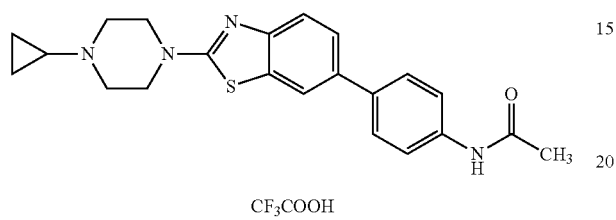

CF$_3$COOH

To a solution of 6-bromo-2-(4-cyclopropylpiperazin-1-yl)benzothiazole (500 mg, 1.48 mmol) and 4-acetamidophenylboronic acid (319 mg, 1.78 mmol) in a 5:1 mixture of THF and H$_2$O (20 mL) was added Pd$_2$(dba)$_3$ (240 mg, 0.148 mmol), followed by P(t-Bu)$_3$BF$_4$ (86 mg, 0.296 mmol) and K$_3$PO$_4$.H$_2$O (1.97 g, 7.4 mmol). The mixture was heated at 60° C. for 3 h, filtered and the volatiles were evaporated. Water (5 mL) was added and the mixture was extracted with CH$_2$Cl$_2$ (3×20 mL). The combined organic extracts were dried (Na$_2$SO$_4$) and concentrated. The residue was purified by the preparative HPLC to give 42 mg (7%) of N-{4-[2-(4-cyclopropylpiperazin-1-yl)benzothiazol-6-yl]phenyl}-acetamide as a trifluoroacetate salt.
$^1$H NMR (300 MHz, CD$_3$OD): δ 7.98 (s, 1H), 7.78-7.55 (m, 6H), 4.05-3.85 (m, 4H), 3.70-3.46 (m, 4H), 3.05-2.88 (m, 1H), 2.15 (s, 3H), 1.15-1.00 (m, 4H).
HPLC (Method B): t$_r$=4.17 min (96.0%).

Example 27

General Procedure E

Cyclopropyl-[2-(4-cyclopropylpiperazin-1-yl)benzothiazol-6-ylmethyl]-amine, trifluoroacetate

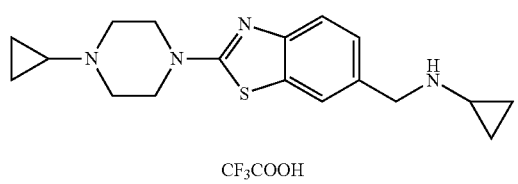 [SMILES: c1cc2nc(N3CCN(C4CC4)CC3)sc2cc1CNC1CC1 ; "CF3COOH"]

CF$_3$COOH

To a solution of 2-(4-cyclopropylpiperazin-1-yl)benzothiazole-6-carbaldehyde (400 mg, 1.39 mmol) and cyclopropylamine (159 mg, 2.78 mmol) in a 1:3 mixture of CH$_3$OH and THF (40 mL) was added AcOH (417 mg, 6.95 mmol), followed by NaCNBH$_3$ (140 mg, 2.22 mmol). The mixture was heated at reflux for 12 h and then the volatiles were evaporated. Water (10 mL) was added and the mixture was extracted with CH$_2$Cl$_2$ (3×15 mL). The combined organic extracts were dried (Na$_2$SO$_4$) and concentrated. The residue was purified by the preparative HPLC to give 362 mg (79%) of cyclopropyl-[2-(4-cyclopropylpiperazin-1-yl)-benzothiazol-6-ylmethyl]-amine as a trifluoroacetate salt.
$^1$H NMR (300 MHz, CD$_3$OD): δ 7.87 (d, 1H), 7.60 (d, 1H), 7.46 (dd, 1H), 4.38 (s, 2H), 4.10-3.85 (m, 4H), 3.65-3.55 (m, 4H), 2.95-2.85 (m, 1H), 2.85-2.72 (m, 1H), 1.15-0.80 (m, 8H).
HPLC (Method B): t$_r$=2.63 min (99.8%).

Example 28

General Procedure N 2-(4-Cyclopropylpiperazin-1-yl)-6-(1,1-dioxo-1λ$^6$-isothiazolidin-2-ylmethyl)benzothiazole

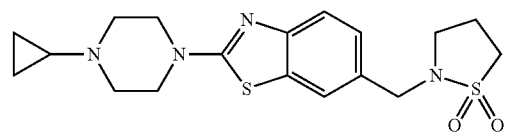 [SMILES: O=S1(=O)CCCN1Cc1ccc2nc(N3CCN(C4CC4)CC3)sc2c1]

Step A:

Synthesis of 6-aminomethyl-2-(4-cyclopropylpiperazin-1-yl)benzothiazole

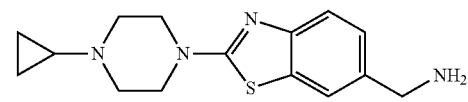 [SMILES: NCc1ccc2nc(N3CCN(C4CC4)CC3)sc2c1]

To a solution of 2-(4-cyclopropylpiperazin-1-yl)benzothiazole-6-carbonitrile (1 g, 3.52 mmol) in MeOH-THF (120 mL, 5:3) was added NH$_4$OH (15 mL) and Raney Ni (200 mg). The mixture was stirred for 12 h at rt under 50 psi H$_2$ atmosphere. After filtration, the mixture was concentrated to give 6-aminomethyl-2-(4-cyclopropylpiperazin-1-yl)benzothiazole (500 mg, 49.3%), which was used in the next step without further purification.

Step B:

3-chloropropane-1-sulfonic acid [2-(4-cyclopropylpiperazin-1-yl)benzothiazol-6-ylmethyl]-amide

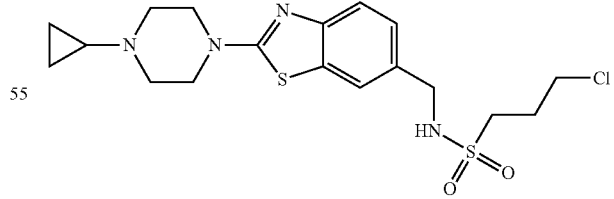

To a solution of 6-aminomethyl-2-(4-cyclopropylpiperazin-1-yl)benzothiazole (500 mg, 1.74 mmol) in CH$_2$Cl$_2$ (15 mL) was added triethylamine (879 mg, 8.2 mmol). The mixture was stirred at 0° C. for 5 min and then 3-chloropropane-1-sulfonyl chloride (308 mg, 1.74 mmol) was added dropwise. The mixture was stirred at 0° C. for 1 h and then allowed gradually to reach rt. Then the mixture was stirred for another 1 h at rt. The volatiles were evaporated and the residue was extracted with CH$_2$Cl$_2$. This afforded a crude product, which was purified by column chromatography on silica gel (elute: 5% CH$_2$Cl$_2$ in methanol) to give 3-chloro-propane-1-sulfonic acid [2-(4-cyclopropylpiperazin-1-yl)benzothiazol-6-ylmethyl]amide 300 mg (39.5%).

$^1$H NMR (400 MHz, CDCl$_3$): δ 7.60 (s, 1H), 7.51 (d, 1H), 7.25 (d, 1H), 4.58-4.48 (m, 1H), 4.34 (d, 2H), 3.68-3.58 (m, 6H), 3.10 (t, 2H), 2.80-2.70 (m, 4H), 2.30-2.20 (m, 2H), 1.75-1.68 (m, 1H), 0.55-0.42 (m, 4H).

Step C:

A mixture of 3-chloropropane-1-sulfonic acid [2-(4-cyclopropylpiperazin-1-yl)benzothiazol-6-ylmethyl]amide (300 mg, 0.70 mmol) and potassium hydroxide (396 mg, 7.0 mmol) in EtOH (5 mL) was heated at reflux for 1 h. The volatiles were evaporated and the residue was extracted with CH$_2$Cl$_2$, washed with brine and concentrated in vacuo. The crude residue was purified by column chromatography on silica gel (elute: 5% CH$_2$Cl$_2$ in methanol) to give 2-(4-cyclopropylpiperazin-1-yl)-6-(1,1-dioxo-1$\lambda^6$-isothiazolidin-2-ylmethyl)benzothiazole 193 mg (49%).

$^1$H NMR (400 MHz, D$_2$O): δ 7.84 (d, 1H), 7.62 (s, 1H), 7.39 (d, 1H), 4.45-4.30 (m, 4H), 3.90-3.68 (m, 5H), 3.55-3.40 (m, 4H), 3.35 (t, 2H), 2.48-2.35 (m, 2H), 1.45 (d, 6H).

Example 29

General Procedure N 2-(4-Cyclopropylpiperazin-1-yl)-6-(1,1-dioxo-1$\lambda^6$-isothiazolidin-2-yl)benzothiazole

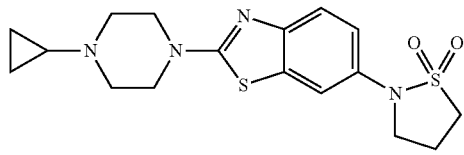 [SMILES: O=S1(=O)CCCN1c1ccc2nc(N3CCN(C4CC4)CC3)sc2c1]

Step A:

2-(4-Cyclopropylpiperazin-1-yl)benzothiazol-6-ylamine

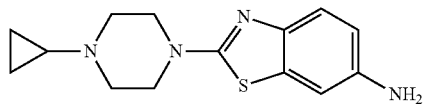

To a solution of N-[2-(4-cyclopropylpiperazin-1-yl)benzothiazol-6-yl]-acetamide (679 mg, 2.15 mmol) in EtOH (36 mL) was added concentrated hydrochloric acid (7.2 mL). The mixture was heated at reflux for 2 h. After cooling, the mixture was neutralized with 15% sodium hydroxide. The volatiles were removed under reduced pressure and the residue was dissolved in methanol (10 mL). The mixture was filtered and the filtrate was concentrated in vacuo to give 512 mg (87%) of 2-(4-cyclopropylpiperazin-1-yl)benzothiazol-6-ylamine.

$^1$H NMR (300 MHz, CDCl$_3$): δ 7.36 (d, 1H), 6.95 (d, 1H), 6.68 (dd, 1H), 3.65-3.50 (m, 6H), 2.80-2.70 (m, 4H), 1.52-1.42 (m, 1H), 0.52-0.42 (m, 4H).

Step B:

To a solution of 2-(4-cyclopropylpiperazin-1-yl)benzothiazol-6-ylamine (500 mg, 1.82 mmol) in DMF (10 mL) was added NaH (220 mg, 5.46 mmol) at 0° C. The mixture was allowed to warm to rt and then stirred for 30 min. A solution of 3-chloropropane-1-sulfonyl chloride (450 mg, 2.55 mmol) in DMF (2 mL) was added and the reaction mixture was stirred for 2 h. The resulting mixture was extracted with ethyl acetate (3×20 mL). The combined organic extracts were dried (Na$_2$SO$_4$) and concentrated under reduced pressure to give a residue which was purified by column chromatography on silica gel (elute: 2% dichloromethane in methanol). This afforded 217 mg (31%) of 2-(4-cyclopropylpiperazin-1-yl)-6-(1,1-dioxo-1$\lambda^6$-isothiazolidin-2-yl)benzothiazole.

$^1$H NMR (300 MHz, CDCl$_3$): δ 7.61 (d, 1H), 7.51 (d, 1H), 7.20 (dd, 1H), 3.78 (t, 2H), 3.65-3.55 (m, 4H), 3.38 (t, 2H), 2.80-2.70 (m, 4H), 2.60-2.48 (m, 2H), 1.72-1.65 (m, 1H), 0.55-0.41 (m, 4H).

HPLC (Method A): t$_r$=2.19 min (95%).

Example 30

General Procedure A 2-(4-Isopropylpiperazin-1-yl)benzothiazole-5-carbonitrile, trifluoroacetate

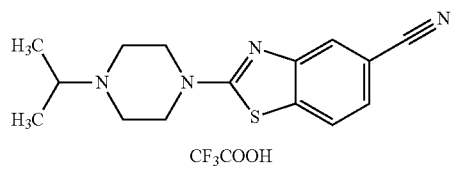

Step A:

2-Thioxo-2,3-dihydrobenzothiazole-5-carbonitrile

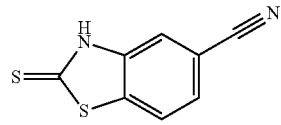

A mixture of 3-amino-4-chlorobenzonitrile (200 mg, 1.32 mmol) and potassium o-ethyl-xanthate (422 mg, 2.64 mmol) in N-methyl-2-pyrrolidone (1.5 mL) was heated at 140° C. for 2 h. After cooling, the mixture was poured into ice-water. Then concentrated hydrochloric acid (0.2 mL) was added. The solid was collected, washed with water and dried to give 2-thioxo-2,3-dihydrobenzothiazole-5-carbonitrile 250 mg (99%).

$^1$H NMR (400 MHz, CDCl$_3$): δ 7.53-7.50 (m, 2H); 7.49 (s, 1H).

Step B:

2-Methylsulfanylbenzothiazole-5-carbonitrile

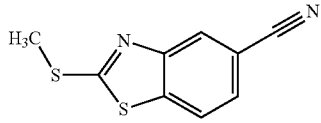

To a solution of 2-thioxo-2,3-dihydrobenzothiazole-5-carbonitrile (260 mg, 1.35 mmol) in EtOH (10.8 mL) was added Et₃N (137 mg, 1.35 mmol) and methyliodide (192 mg, 1.35 mmol). The mixture was heated at reflux for 1 h. The volatiles were evaporated and the residue was extracted with CH₂Cl₂ (3×10 mL). The combined organic extracts were washed with brine, dried (Na₂SO₄) and concentrated to give 2-methylsulfanylbenzothiazole-5-carbo-nitrile 271 mg (97%).

¹H NMR (300 MHz, CDCl₃): δ 8.13 (s, 1H), 7.84 (d, 1H), 7.52 (dd, 1H), 2.82 (s, 3H).

Step C:

A mixture of 2-methylsulfanylbenzothiazole-5-carbonitrile (500 mg, 2.43 mmol), 1-isopropyl-piperazine (3.11 g, 24.3 mmol) and pyridine (1.92 g, 24.3 mmol) was heated at 160° C. for 5 h. After removing pyridine, the mixture was extracted with CH₂Cl₂ (3×10 mL). The combined organic extracts were washed with brine, dried (Na₂SO₄) and concentrated to give a residue which was purified by the preparative HPLC. This afforded 81 mg (12%) of 2-(4-isopropyl-piperazin-1-yl)benzothiazole-5-carbonitrile as a trifluoroacetate salt.

¹H NMR (400 MHz, D₂O): δ 7.74 (d, 1H), 7.68 (s, 1H), 7.38 (d, 1H), 4.30-4.20 (m, 2H), 3.60-3.50 (m, 5H), 3.30-3.20 (m 2H), 1.29 (d, 6H).

HPLC (Method B): t_r=3.95 min (97.0%).

Example 31

General Procedure E 2-(4-Isopropylpiperazin-1-yl)-5-pyrrolidin-1-ylmethylbenzothiazole, trifluoroacetate

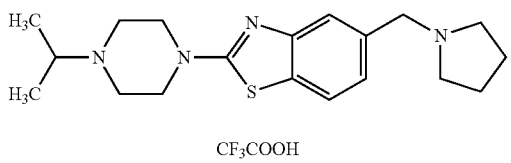 [SMILES: CC(C)N1CCN(c2nc3cc(CN4CCCC4)ccc3s2)CC1 ; "CF3COOH"]

To a solution of 2-(4-isopropylpiperazin-1-yl)benzothiazole-5-carbaldehyde (270 mg, 0.93 mmol) and pyrrolidine (133 mg, 1.86 mmol) in CH₃OH/THF (12 mL, 1:2) was added acetic acid (179 mg, 2.98 mmol) and NaCNBH₃ (173 mg, 2.98 mmol). The mixture was heated at reflux for 12 h. The volatiles were removed and the residue was diluted with water (5 mL). The resulting mixture was extracted with CH₂Cl₂ (3×10 mL). The combined organic extracts were dried (Na₂SO₄) and concentrated under reduced pressure to give a residue which was purified by the preparative HPLC. This afforded 306 mg (48%) of 2-(4-isopropylpiperazin-1-yl)-5-pyrrolidin-1-ylmethylbenzothiazole as a trifluoroacetate salt.

¹H NMR (400 MHz, D₂O): δ 7.78 (d, 1H), 7.56 (d, 1H), 7.28 (dd, 1H), 4.36 (s, 2H), 4.30-4.20 (m, 2H), 3.70-3.52 (m, 5H), 3.48-3.38 (m, 2H), 3.35-3.25 (m, 2H), 3.18-3.05 (m, 2H), 2.12-2.00 (m, 2H), 1.90-1.80 (m, 2H), 1.29 (d, 6H).

HPLC (Method B): t_r=2.28 min (98.3%).

Example 32

General Procedure O

[2-(4-Isopropylpiperazin-1-yl)benzothiazol-5-ylmethyl]dimethyl-amine, trifluoroacetate

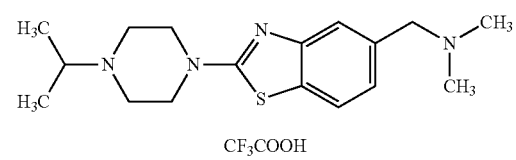

Step A:

5-Bromobenzothiazole-2-thiol

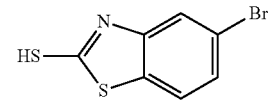

To a solution of 5-bromo-2-fluorobenzenamine (200 mg, 1.28 mmol) in N-methyl-2-pyrrolidine (1.5 mL) was added potassium o-ethyl carbonodithioate (410 mg, 2.56 mmol). The mixture was heated at 140° C. for 2 h. The reaction mixture was poured into a large amount of water, acidified with concentrated hydrochloric acid, and filtered to give 5-bromo-benzothiazole-2-thiol 300 mg (95%).

Step B:

5-bromo-2-(methylthio)benzo[d]thiazole

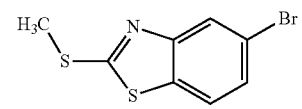

To a solution of 5-bromobenzo[d]thiazole-2-thiol (24 mg, 0.098 mmol) in EtOH (1.5 mL) was added triethylamine (10 mg, 0.098 mmol) and methyliodide (14 mg, 0.098 mmol). The mixture was heated at reflux for 1.5 h. Then the mixture was extracted with dichloromethane (3×10 mL). The combined organic extracts were washed with brine, dried (Na₂SO₄) and concentrated to give 5-bromo-2-(methylthio) benzothiazole 20 mg (80%).

¹H NMR (400 MHz, CDCl₃): δ 8.02 (s, 1H), 7.60 (d, 1H), 7.39 (d, 1H), 2.79 (s, 3H).

Step C:

5-bromo-2-(4-isopropylpiperazin-1-yl)benzothiazole

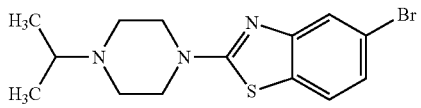

A mixture of 5-bromo-2-(methylthio)benzothiazole (200 mg, 0.77 mmol), 1-isopropyl-piperazine (985 mg, 7.7 mmol) and pyridine (610 mg, 7.7 mmol) was heated at 160° C. for 36 h. The reaction mixture was concentrated under reduced pressure and the residue was extracted with dichloromethane (3×10 mL). The combined organic extracts were washed with brine, dried ($Na_2SO_4$) and concentrated. The residue was purified by column chromatography on silica gel (eluent: 2% EtOAc in Petroleum ether) to give 200 mg (77%) of 5-bromo-2-(4-isopropylpiperazin-1-yl)benzothiazole.

Step D:

2-(4-Isopropylpiperazin-1-yl)benzothiazole-5-carbaldehyde

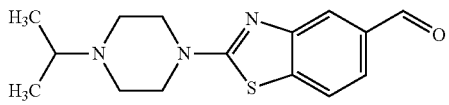

To a solution of 5-bromo-2-(4-isopropylpiperazin-1-yl)benzothiazole (300 mg, 0.88 mmol) in dry THF was added n-BuLi dropwise over 10 min at −78° C. After 30 min, DMF was added dropwise at −78° C. The reaction mixture was then stirred for 1.5 h at −78° C., quenched with water and extracted with ethyl acetate to give a residue which was purified by column chromatography on silica gel (eluent: 1% dichloromethane in methanol). This afforded 240 mg (94%) of 2-(4-isopropylpiperazin-1-yl)benzothiazole-5-carbaldehyde.

$^1$H NMR (400 MHz, $CDCl_3$): δ 10.03 (s, 1H), 7.98 (s, 1H), 7.72 (d, 1H), 7.60 (d, 1H), 3.66 (s, 4H), 2.85-2.75 (m, 1H), 2.70-2.60 (m, 4H), 1.09 (d, 6H).

Step E:

To a solution of 2-(4-isopropylpiperazin-1-yl)benzothiazole-5-carbaldehyde (500 mg, 1.73 mmol) and dimethylamine hydrochloride (282 mg, 3.46 mmol) in THF (27.5 mL) and MeOH (13.7 mL) was added acetic acid (166 mg, 2.77 mmol), followed by $NaCNBH_3$ (160 mg, 2.77 mmol). The mixture was heated at reflux overnight. The mixture was concentrated under reduced pressure, neutralized with an aqueous solution of $Na_2CO_3$ to pH 7, and filtered. The residue was extracted with dichloromethane (3×10 mL). The combined organic extracts were washed with brine, dried ($Na_2SO_4$) and concentrated. The residue was purified by preparative HPLC to give 251 mg (46%) of [2-(4-isopropylpiperazin-1-yl)benzothiazol-5-yl-methyl]dimethylamine as a trifluoroacetate salt.

$^1$H NMR (400 MHz, $D_2O$): δ 7.78 (d, 1H), 7.54 (s, 1H), 7.21 (d, 1H), 4.29 (s, 2H), 4.23 (d, 2H), 3.65-3.50 (m, 5H), 3.32-3.20 (m, 2H), 2.774 (s, 6H), 1.29 (d, 6H).

HPLC (Method B): $t_r$=2.05 min (96.0%).

Example 33

General Procedure D

[2-(4-Isopropylpiperazin-1-yl)benzothiazol-5-yl]pyrrolidin-1-ylmethanone, trifluoroacetate

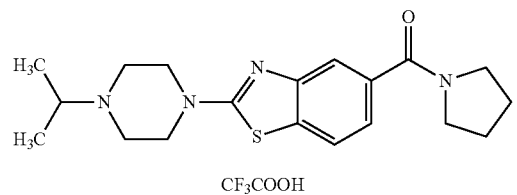

Step A:

2-(4-Isopropylpiperazin-1-yl)benzothiazole-5-carboxylic acid

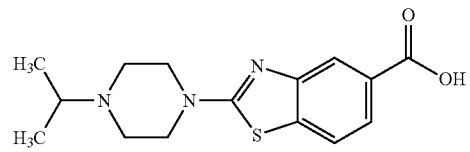

A solution of 2-(4-isopropylpiperazin-1-yl)benzothiazole-5-carbonitrile (300 mg, 1.04 mmol) in concentrated hydrochloric acid (10 mL) was heated at reflux for 3 h. The mixture was concentrated under reduced pressure to give 315 mg (99%) of 2-(4-isopropylpiperazin-1-yl)-benzothiazole-5-carboxylic acid, which was used directly in the next step.

Step B:

A solution of 2-(4-isopropylpiperazin-1-yl)benzothiazole-5-carboxylic acid (530 mg, 1.75 mmol), pyrrolidine (149 mg, 2.10 mmol) and DIEA in THF (7.3 mL) was stirred for 30 min at rt. Then PyBOP was added and the reaction mixture was stirred at rt overnight. The mixture was concentrated and the residue was neutralized with an aqueous solution of $Na_2CO_3$ to pH 7. Then the mixture was extracted with dichloromethane (3×10 mL). The combined organic extracts were washed with brine, dried ($Na_2SO_4$) and concentrated. The residue was purified with preparative HPLC to give 490 mg (78%) of (2-(4-isopropylpiperazin-1-yl)benzothiazol-5-yl)(pyrrolidin-1-yl)methanone as a trifluoroacetate salt.

$^1$H NMR (400 MHz, $D_2O$): δ 7.77 (d, 1H), 7.53 (s, 1H), 7.25 (d, 1H), 4.24 (d, 2H), 3.65-3.50 (m, 5H), 3.49 (t, 2H), 3.36 (t, 2H), 3.25 (s, 2H), 1.95-1.85 (m, 2H), 1.83-1.73 (m, 2H), 1.29 (d, 6H).

HPLC (Method B): $t_r$=2.86 min (96.9%).

Example 34

General Procedure N 5-(1,1-Dioxo-1λ$^6$-isothiazolidin-2-ylmethyl)-2-(4-isopropylpiperazin-1-yl)benzothiazole, trifluoroacetate

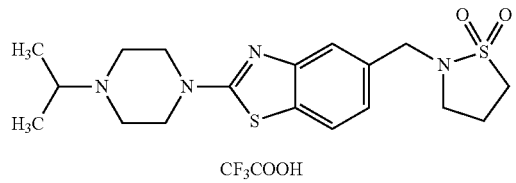

CF$_3$COOH

Step A:

5-Aminomethyl-[2-(4-isopropylpiperazin-1-yl)benzothiazole

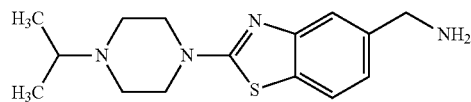

To a solution of 2-(4-isopropylpiperazin-1-yl)benzothiazole-5-carbonitrile (500 mg, 1.75 mmol) in MeOH-THF (66 mL, 3:5) was added NH$_4$OH (7 mL) and Raney Ni (100 mg). The mixture was stirred for 12 h at rt under a H$_2$ atmosphere. The mixture was filtered and the filtrate was concentrated to give 5-aminomethyl-[2-(4-isopropylpiperazin-1-yl)benzothiazole 507 mg (100%), which was used in the next step without further purification.

$^1$H NMR (300 MHz, CDCl$_3$): δ 7.54 (d, 1H), 7.49 (s, 1H), 7.03 (dd, 1H), 3.90 (s, 2H), 3.70-3.62 (m, 4H), 2.85-2.75 (s, 1H), 2.70-2.60 (m, 4H), 1.08 (d, 6H).

Step B:

To a solution of 5-aminomethyl-[2-(4-isopropylpiperazin-1-yl)benzothiazole (439 mg, 1.51 mmol) in DMF (10 mL) was added NaH (181 mg, 4.53 mmol) at 0° C. The mixture was allowed to warm to rt. After 30 min, a solution of 3-chloropropane-1-sulfonic acid (373 mg, 2.11 mmol) in DMF (1.67 mL) was added at rt. The reaction mixture was stirred at rt for 2 h and then quenched with water. The volatiles were removed and the residue was extracted with ethyl acetate. The organic extract was washed with brine and concentrated. The residue was purified by the preparative HPLC to give 267 mg (45%) of 5-(1,1-dioxo-1λ$^6$-iso-thiazolidin-2-ylmethyl)-2-(4-isopropylpiperazin-1-yl)benzothiazole as a trifluoroacetate salt.

$^1$H NMR (400 MHz, D$_2$O): δ 7.84 (d, 1H), 7.62 (s, 1H), 7.39 (d, 1H), 4.45-4.30 (m, 4H), 3.90-3.68 (m, 5H), 3.55-3.40 (m, 4H), 3.35 (t, 2H), 2.48-2.35 (m, 2H), 1.45 (d, 6H).

HPLC (Method B): t$_r$=2.76 min (95.6%).

Example 35

General Procedure A 2-(4-Cyclopropylpiperazin-1-yl)benzooxazole-5-carbonitrile

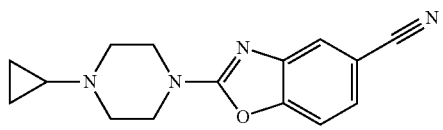 [SMILES: N#Cc1ccc2oc(N3CCN(C4CC4)CC3)nc2c1]

Step A:

4-Hydroxy-3-nitrobenzonitrile

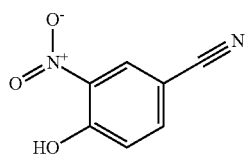 [SMILES: N#Cc1ccc(O)c([N+](=O)[O-])c1]

A mixture of nitric acid (1.16 g, 12 mmol) and glacial acetic acid (1 mL) was heated to 40° C. To this mixture was added rapidly a solution of 4-hydroxybenzonitrile (1 g, 8.4 mmol) in glacial acetic acid (4 mL) until the flask temperature rose to 50° C. Then the solution was added at a rate such that the temperature was maintained at 50-60° C. When addition was complete the mixture was stirred for another 20 min at 55° C., and then poured into ice-water (24 mL). The mixture was filtered and the solid was washed with water to give 4-hydroxy-3-nitrobenzonitrile 1.09 g (79%) as a solid.

$^1$H NMR (300 MHz, CDCl$_3$): δ 10.91 (s, 1H), 8.48 (d, 1H), 7.82 (dd, 1H), 7.28 (dd, 1H).

Step B:

3-Amino-4-hydroxybenzonitrile

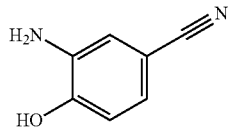

A mixture of 4-hydroxy-3-nitrobenzonitrile (100 mg, 0.61 mmol), palladium on charcoal (10 mg, 10%), EtOH (0.67 mL) and ethyl acetate (0.33 mL) was hydrogenated at rt for 2 h. Then the mixture was filtered and concentrated to give 3-amino-4-hydroxybenzonitrile 60 mg (73%) as a solid.

$^1$H NMR (300 MHz, CD$_3$OD): δ 6.92 (dd, 1H), 6.88 (d, 1H), 6.74 (dd, 1H).

Step C:

2-Thioxo-2,3-dihydrobenzooxazole-5-carbonitrile

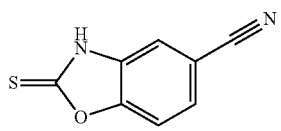 [SMILES: N#Cc1ccc2oc(=S)[nH]c2c1]

A mixture of 3-amino-4-hydroxybenzonitrile (50 mg, 0.37 mmol) and potassium O-ethyl-xanthate (65 mg, 0.41 mmol) in pyridine (0.75 mL) was heated at reflux for 2 h. After cooling, the mixture was poured into ice-water. Then concentrated hydrochloric acid (0.2 mL) was added. The solid was collected, washed with water and dried to give 2-thioxo-2,3-dihydro-benzooxazole-5-carbonitrile 30 mg (46%).

$^1$H NMR (400 MHz, DMSO-$d_6$): δ 7.80-7.62 (m, 3H).

Step D:

2-Chlorobenzooxazole-5-carbonitrile

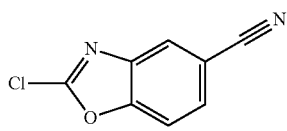 [SMILES: N#Cc1ccc2oc(Cl)nc2c1]

To a mixture of 2-thioxo-2,3-dihydrobenzooxazole-5-carbonitrile (2.56 g, 14.5 mmol) and thionylchloride (14.1 mL) was added two drops of DMF. The mixture was heated at 65-70° C. for 1 h. Then the mixture was cooled to rt and diluted with CH$_2$Cl$_2$. The solvent and excess thionylchloride were removed under reduced pressure. The residue was purified by column chromatography on silica gel (eluent: 20% EtOAc in Petroleum ether) to give 2-chlorobenzo-oxazole-5-carbonitrile 1.69 g (65%).

$^1$H NMR (400 MHz, DMSO-$d_6$): δ 7.80-7.62 (m, 3H).

Step E:

To a solution of 2-chlorobenzooxazole-5-carbonitrile (1.69 g, 9.5 mmol) in EtOH (34 mL) was added Et$_3$N (4.8 g, 47.5 mmol), followed by 1-cyclopropylpiperazine (1.44 g, 11.4 mmol) and the mixture was heated at reflux for 12 h. Then the volatiles were evaporated to remove EtOH and water (120 mL) was added. The mixture was extracted with CH$_2$Cl$_2$ (3×50 mL). The combined organic extracts were washed with brine, dried (Na$_2$SO$_4$) and concentrated. The residue was purified by column chromatography on silica gel (elute: 10% ethyl acetate in petroleum ether, 0.1% NH$_4$OH added) to give 1.34 g (53%) of 2-(4-cyclopropylpiperazin-1-yl)benzooxazole-5-carbonitrile.

$^1$H NMR (300 MHz, CD$_3$OD): δ 7.58 (d, 1H), 7.55-7.38 (m, 2H), 3.80-3.65 (m, 4H), 2.85-2.70 (m, 4H), 1.82-1.68 (m, 1H), 0.60-0.40 (m, 4H).

HPLC (Method B): t$_r$=2.10 min (99.7%).

Example 36

General Procedure D

[2-(4-Cyclopropylpiperazin-1-yl)benzoxazol-5-yl]pyrrolidin-1-ylmethanone, trifluoroacetate

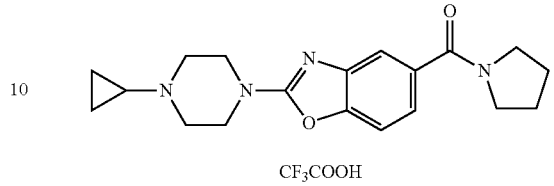

CF$_3$COOH

Step A:

2-(4-Cyclopropylpiperazin-1-yl)benzooxazole-5-carboxylic acid

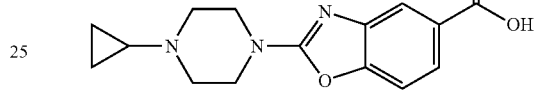

A mixture of 2-(4-cyclopropylpiperazin-1-yl)benzooxazole-5-carbonitrile (322 mg, 1.2 mmol) in concentrated hydrochloric acid (10 mL) was heated at reflux for 4 h. Then the reaction mixture was concentrated to give 2-(4-cyclopropylpiperazin-1-yl)benzooxazole-5-carboxylic acid (340 mg, 99%), which was used in the next step without further purification.

Step B:

To a mixture of 2-(4-cyclopropylpiperazin-1-yl)benzooxazole-5-carboxylic acid (340 mg, 1.18 mmol), pyrrolidine (102 mg, 1.44 mmol) and diisopropylethylamine (372 mg, 2.88 mmol) in THF (5 mL) was added PyBop (1.25 g, 2.4 mmol) portionwise at 25° C. After stirring for 15 h, the mixture was diluted with water and extracted with ethyl acetate (3×10 mL). The combined organic extracts were washed with brine, dried (Na$_2$SO$_4$) and concentrated. The residue was purified by the preparative HPLC to give 141 mg (35%) of [2-(4-cyclopropyl-piperazin-1-yl)benzooxazol-5-yl]pyrrolidin-1-ylmethanone as a trifluoroacetate salt.

$^1$H NMR (300 MHz, CD$_3$OD): δ 7.55-7.42 (m, 2H), 7.30 (dd, 1H), 4.20-3.53 (m, 10H), 3.30 (t, 2H), 3.02-2.88 (m, 1H), 2.08-1.85 (m, 4H), 1.12-0.98 (m, 4H).

HPLC (Method B): t$_r$=2.44 min (95.0%).

Example 37

General Procedure N 2-(4-Cyclopropylpiperazin-1-yl)-5-(1,1-dioxo-1λ$^6$-isothiazolidin-2-ylmethyl)benzoxazole, trifluoroacetate

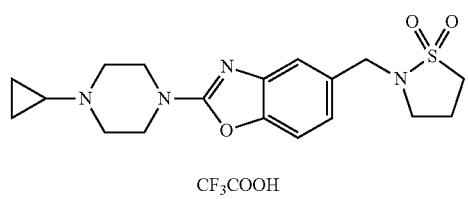 [SMILES: O=S1(=O)CCCN1Cc1ccc2oc(N3CCN(C4CC4)CC3)nc2c1 ; "CF3COOH"]

CF$_3$COOH

Step A:

5-Aminomethyl-[2-(4-cyclopropylpiperazin-1-yl)benzooxazole

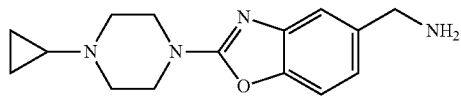 [SMILES: NCc1ccc2oc(N3CCN(C4CC4)CC3)nc2c1]

To a solution of 2-(4-cyclopropylpiperazin-1-yl)benzooxazole-5-carbonitrile (500 mg, 1.85 mmol) in MeOH-THF (12 mL, 5:3) was added NH$_4$OH (1.5 mL) and Raney Ni (100 mg). The mixture was stirred for 12 h at rt under a H$_2$ atmosphere. After filtration, the mixture was concentrated to give 5-aminomethyl-[2-(4-cyclopropylpiperazin-1-yl)benzooxazole (500 mg, 99%), which was used in the next step without further purification.

$^1$H NMR (400 MHz, CDCl$_3$): δ 7.28 (s, 1H), 7.19 (d, 1H), 6.96 (d, 1H), 3.88 (s, 2H), 3.75-3.62 (m, 4H), 2.78-2.68 (m, 4H), 1.72-1.65 (m, 1H), 0.56-0.40 (m, 4H).

Step B:

3-Chloropropane-1-sulfonic acid [2-(4-cyclopropylpiperazin-1-yl)benzooxazol-5-ylmethyl]

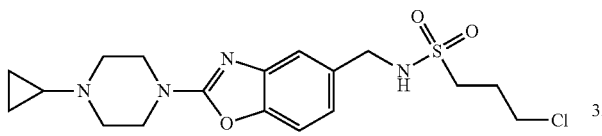

To a solution of 5-aminomethyl-[2-(4-cyclopropylpiperazin-1-yl)benzooxazole (500 mg, 1.84 mmol) in CH$_2$Cl$_2$ (15 mL) was added Et$_3$N (929 mg, 9.2 mmol). The mixture was stirred at 0° C. for 5 min and then 3-chloropropane-1-sulfonyl chloride (326 mg, 1.84 mmol) was added dropwise. The mixture was stirred at 0° C. for 1 h and brought gradually to rt. Then the mixture was stirred for another 1 h. The volatiles were removed and the residue was extracted with CH$_2$Cl$_2$. The resulting residue was purified by column chromatography on silica gel (elute: 5% CH$_2$Cl$_2$ in methanol) to give 3-chloropropane-1-sulfonic acid [2-(4-cyclopropyl-piperazin-1-yl)benzooxazol-5-ylmethyl]amide (315 mg, 42%).

$^1$H NMR (400 MHz, CDCl$_3$): δ 7.24 (s, 1H), 7.17 (d, 1H), 6.95 (d, 1H), 4.55-4.45 (m, 1H), 4.30 (d, 2H), 3.70-3.52 (m, 6H), 3.04 (t, 2H), 2.75-2.65 (m, 4H), 2.78-2.62 (m, 2H), 1.70-1.52 (m, 1H), 0.52-0.38 (m, 4H).

Step C:

A mixture of 3-chloropropane-1-sulfonic acid [2-(4-cyclopropylpiperazin-1-yl)benzooxazol-5-ylmethyl]amide (315 mg, 0.76 mmol) in EtOH (5 mL) and potassium hydroxide (430 mg, 7.6 mmol) was heated at reflux for 1 h. The volatiles were evaporated and the residue was extracted with CH$_2$Cl$_2$. The organic extract was washed with brine and concentrated to give a residue which was purified by the preparative HPLC. This afforded 97 mg (34%) of 2-(4-cyclopropylpiperazin-1-yl)-5-(1,1-dioxo-1λ$^6$-isothiazolidin-2-ylmethyl)benzooxazole as a trifluoroacetate salt.

$^1$H NMR (300 MHz, D$_2$O): δ 7.36 (dd, 1H), 7.32 (s, 1H), 7.17 (dd, 1H), 4.17 (s, 2H), 4.10-3.70 (m, 8H), 3.27 (t, 2H), 3.15 (t, 2H), 2.90-2.75 (m, 1H), 2.30-2.18 (m, 2H), 0.98-0.88 (m, 4H).

HPLC (Method B): t$_r$=2.26 min (95.7%).

Example 38

General Procedure E 2-(4-Cyclopropylpiperazin-1-yl)-5-pyrrolidin-1-ylmethylbenzoxazole

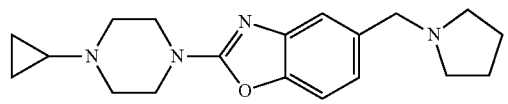 [SMILES: c1cc2oc(N3CCN(C4CC4)CC3)nc2cc1CN1CCCC1]

Step A:

2-(4-Cyclopropylpiperazin-1-yl)benzoxazole-5-carboxaldehyde

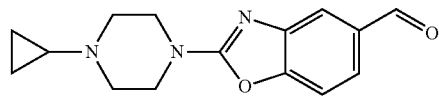 [SMILES: O=Cc1ccc2oc(N3CCN(C4CC4)CC3)nc2c1]

To a solution of 2-(4-cyclopropylpiperazin-1-yl)benzooxazole-5-carbonitrile (1.5 g, 5.6 mmol) in THF-toluene (50 mL, 2:1) was added DIBAL (16.8 mL, 16.8 mmol) dropwise at −78° C. under a nitrogen atmosphere. Then the mixture was allowed to warm to 20° C. and then stirred for 1 h. Methanol (5 mL) was added dropwise, followed by water (20 mL). The mixture was extracted with ethyl acetate (3×20 mL) and the combined organic extracts were dried (Na$_2$SO$_4$) and concentrated. The residue was purified by column chromatography on silica gel (elute: 2% dichloromethane in methanol) to give 1.1 g (72%) of 2-(4-cyclopropyl-piperazin-1-yl)benzooxazole-5-carboxaldehyde.

$^1$H NMR (300 MHz, CDCl$_3$): δ 9.99 (s, 1H), 7.82 (d, 1H), 7.60 (dd, 1H), 7.34 (dd, 1H), 3.78-3.68 (m, 4H), 2.78-2.69 (m, 4H), 1.75-1.65 (m, 1H), 0.58-0.40 (m, 4H).

Step B:

To a solution of 2-(4-cyclopropylpiperazin-1-yl)benzooxazole-5-carboxaldehyde (400 mg, 1.48 mmol) and pyrrolidine (210 mg, 2.96 mmol) in CH$_3$OH/THF (36 mL, 1:3) was added acetic acid (142 mg, 2.37 mmol), followed by NaCNBH$_3$ (137 mg, 2.37 mmol). The mixture was heated at reflux for 12 h. The volatiles were removed and the residue was diluted with water (5 mL). The resulting mixture was extracted with CH$_2$Cl$_2$ (3×10 mL) and the combined organic extracts were dried (Na$_2$SO$_4$) and concentrated. The residue was purified by column chromatography on silica gel (elute: 2% dichloromethane in methanol) to give 193 mg (40%) of 2-(4-cyclopropylpiperazin-1-yl)-5-pyrrolidin-1-ylmethylbenzooxazole.

$^1$H NMR (400 MHz, D$_2$O): δ 7.48 (m, 2H), 7.27 (dd, 1H), 4.43 (s, 2H), 4.12 (broad m, 4H), 3.51 (m, 2H), 3.20 (m, 2H), 2.93 (m, 1H), 2.17 (m, 2H), 1.98 (m, 2H), 1.05 (m, 4H).

Example 39

General Procedure E

[2-(4-Cyclopropylpiperazin-1-yl)benzoxazol-5-ylmethyl]dimethylamine, trifluoroacetate

CF$_3$COOH

To a solution of 2-(4-cyclopropylpiperazin-1-yl)benzooxazole-5-carboxaldehyde (350 mg, 1.29 mmol) and dimethylamine hydrochloride (210 mg, 2.58 mmol) in CH$_3$OH/THF (32 mL, 1:3) was added acetic acid (124 mg, 2.06 mmol), followed by NaCNBH$_3$ (120 mg, 2.06 mmol). The mixture was heated at reflux for 12 h. The volatiles were removed under reduced pressure and the residue was diluted with water (5 mL). The mixture was extracted with CH$_2$Cl$_2$ (3×10 mL) and the combined organic extracts were dried (Na$_2$SO$_4$) and concentrated. The residue was purified by the preparative HPLC to give 233 mg (60%) of [2-(4-cyclopropylpiperazin-1-yl)benzooxazol-5-ylmethyl]dimethylamine as a trifluoroacetate salt.

$^1$H NMR (300 MHz, D$_2$O): δ 7.41 (d, 1H), 7.36 (s, 1H), 7.18 (d, 1H), 4.25 (s, 2H), 4.20-3.25 (m, 8H), 2.86-2.78 (m, 1H), 2.72 (s, 6H), 1.00-0.88 (m, 4H).

HPLC (Method B): t$_r$=2.00 min (99.0%).

Example 40

2-(4-Cyclopropylpiperazin-1-yl)-6-(pyrrolidin-1-ylmethyl)benzothiazole, hydrochloride

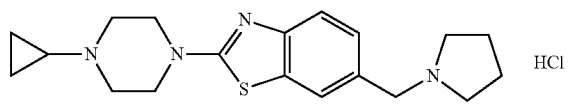 [SMILES: c1cc2nc(N3CCN(C4CC4)CC3)sc2cc1CN1CCCC1 ; Cl]

Pharmacological Methods

The ability of the compounds to interact with the histamine H3 receptor can be determined by the following in vitro binding assays.

Binding Assay I

Rat cerebral cortex is homogenized in ice cold K-Hepes, 5 mM MgCl$_2$ pH 7.1 buffer. After two differential centrifugations the last pellet is resuspended in fresh Hepes buffer containing 1 mg/ml bacitracin. Aliquots of the membrane suspension (400 μg/ml) are incubated for 60 min at 25° C. with 30 pM [$^{125}$I]-iodoproxifan (a known histamine H3 receptor antagonist) and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analyzed by non-linear regression analysis.

Binding Assay II

The H3-receptor agonist ligand R-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter. Male Wistar rats (150-200 g) are decapitated, and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM MgCl$_2$ pH 7.1 (KOH)+1 mg/ml bacitracin) using an Ultra-Turrax homogenizer for 30 seconds. The homogenate is centrifuged at 140 g in 10 min. The supernatant is transferred to a new test tube and centrifuged for 30 min at 23 000 g. Pellet is resuspended in 5-10 ml Hepes buffer, homogenized and centrifuged for 10 min at 23 000 g. This short centrifugation step is repeated twice. After the last centrifugation the pellet is resuspended in 2-4 ml Hepes buffer and the protein concentration is determined. The membranes are diluted to a protein concentration of 5 mg/ml using Hepes buffer, aliquoted and stored at −80° C. until use.

50 μl test-compound, 100 μl membrane (200 μg/ml), 300 μl Hepes buffer and 50 μl R-α-methyl[$^3$H]histamine (1 nM) are mixed in a test tube. The compounds to be tested are dissolved in DMSO and further diluted in H$_2$O to the desired concentrations. Radioligand and membranes are diluted in Hepes buffer+1 mg/ml bacitracin. The mixture is incubated for 60 min at 25° C. Incubation is terminated by addition of 5 ml ice-cold 0.9% NaCl, followed by rapid filtration through Whatman GF/B filters pre-treated for 1 hour with 0.5% polyethyleneimine. The filters are washed with 2×5 ml ice-cold NaCl. To each filter is added a 3 ml scintillation cocktail, and the retained radioactivity is measured with a Packard Tri-Carb beta counter.

IC$_{50}$ values are calculated by non-linear regression analysis of binding curves (6 points minimum) using the windows program GraphPad Prism, GraphPad software, USA.

Binding Assay III

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% CO$_2$. Before harvesting, the confluent cells are rinsed with PBS and incubated with Versene (proteinase, GIBCO-BRL) for approximately 5 min. The cells are flushed with PBS and DMEM and the cell suspension collected in a tube and centrifuged for 5-10 min at 1500 rpm in a Heraeus Sepatech Megafuge 1.0. The pellet is resuspended in 10-20 vol. Hepes buffer [20 mM Hepes, 5 mM MgCl$_2$, pH 7.1 (KOH)] and homogenized for 10-20 seconds using an Ultra-Turrax homogenizer. The homogenate is centrifuged for 30 min at 23 000 g. The pellet is resuspended in 5-10 ml Hepes buffer, homogenized 5-10 seconds with the Ultra-Turrax and centrifuged for 10 min at 23 000 g. Following this centrifugation step, the membrane pellet is resuspended in 2-4 ml Hepes buffer, homogenized with a syringe or Teflon homogenizer, and the protein concentration determined. The membranes are diluted to a protein concentration of 1-5 mg/ml in Hepes buffer, aliquoted and kept at −80° C. until use.

Aliquots of the membrane suspension are incubated for 60 min at 25° C. with 30 µM [$^{125}$I]-iodoproxifan (a known compound with high affinity for the H3 receptor) and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra 11 auto gamma counter. The radioactivity of the filters is indirectly proportional to the binding affinity of the tested compound. The results are analysed by non-linear regression analysis. When tested, the present compounds of the formula (I) generally show a high binding affinity to the histamine H3 receptor.

Preferably, the compounds according to the invention have an $IC_{50}$ value as determined by one or more of the assays of less than 10 µM, more preferably less than 1 µM, and still more preferably less than 500 nM, such as less than 100 nM.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G 418 at 37° C. and 5% $CO_2$.

The H3 receptor expressing cells are washed once with phosphate buffered saline (PBS) and harvested using versene (GIBCO-BRL). PBS is added and the cells are centrifuged for 5 min at 188 g. The cell pellet is resuspended in stimulation buffer to a concentration of $1 \times 10^6$ cells/ml. cAMP accumulation is measured using the Flash Plate® cAMP assay (NEN™ Life Science Products). The assay is generally performed as described by the manufacturer. Briefly, 50 µl cell suspension is added to each well of the Flashplate which also contained 25 µl 40 µM isoprenaline, to stimulate cAMP generation, and 25 µl of test compound (either agonists or inverse agonists alone, or agonist and antagonist in combination). The assay can be run in "agonist-mode" in which the test compound is added, in increasing concentration, on its own, to the cells, and cAMP is measured. If cAMP goes up, the compound in question is an inverse agonist; if cAMP does not change, it is a neutral antagonist, and if cAMP goes down, it is an agonist. The assay can also be run in the "antagonist-mode" in which a test compound is added, in increasing concentrations, together with increasing concentrations of a known H3 agonist (e.g. RAMHA). If the test compound is an antagonist, increasing concentrations of it cause a right-ward shift in the H3-agonist's dose-response curves. The final volume in each well is 100 µl. Test compounds are dissolved in DMSO and diluted in $H_2O$. The mixture is shaken for 5 min, and allowed to stand for 25 min at room temperature. The reaction is stopped with 100 µl "Detection Mix" per well. The plates are then sealed with plastic, shaken for 30 min, allowed to stand overnight, and finally the radioactivity is counted in the Cobra II auto gamma topcounter. $EC_{50}$ values are calculated by non-linear regression analysis of dose response curves (6 points minimum) using GraphPad Prism. Kb values are calculated by Schild plot analysis.

Functional Assay II

The ability of the compounds to bind and interact with the human H3 receptor as agonists, inverse agonists and/or antagonists, is determined by a functional assay, named [$^{35}$S] GTPγS assay. The assay measures the activation of G proteins by catalyzing the exchange of guanosine 5'-diphosphate (GDP) by guanosine 5'-triphosphate (GTP) at the -subunit. The GTP-bounded G proteins dissociate into two subunits, $G_{GTP}$ and Gβγ, which in turn regulate intracellular enzymes and ion channels. GTP is rapidly hydrolysed by the G-subunit (GTPases) and the G protein is deactivated and ready for a new GTP exchange cycle. To study the function of ligand-induced G protein coupled receptor (GPCR) activation by an increase in guanine nucleotide exchange at the G proteins, the binding of [$^{35}$S]-guanosine-5'-O-(3-thio)triphosphate [$^{35}$S] GTPγS, a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor. The cells are washed twice in PBS, harvested with PBS+1 mM EDTA, pH 7.4 and centrifuged at 1000 rpm for 5 min. The cell pellet is homogenized in 10 ml ice-cold Hepes buffer (20 mM Hepes, 10 mM EDTA pH 7.4 (NaOH)) using an Ultra-Turrax homogenizer for 30 seconds and centrifuged for 15 min at 20,000 rpm. Following this centrifugation step, the membrane pellet is resuspended in 10 ml ice-cold Hepes buffer (20 mM Hepes, 0.1 mM EDTA pH 7.4 (NaOH)) and homogenized as described above. This procedure is repeated twice except for the last homogenization step, the protein concentration is determined, and membranes are diluted to a protein concentration of 2 mg/ml, aliquoted and kept at −80° C. until use.

In order to study the presence and the potency of an inverse agonist/antagonist, the H3-receptor agonist ligand R-α-methyl histamine (RAMHA) is added. The ability of the test compound to counteract the effect of RAMHA is measured. When studying the effect of an agonist, RAMHA is not added to the assay medium. The test compound is diluted in the assay buffer (20 mM HEPES, 120 mM NaCl, 10 mM $MgCl_2$ pH 7.4 (NaOH)) at various concentrations followed by addition of $10^{-8}$ nM RAMHA (only in the case where an inverse agonist/antagonist is examined), 3 µM GDP, 2.5 µg membranes, 0.5 mg SPA beads and 0.1 nM [$^{35}$S] GTPγS, and incubation for 2 hours with gentle shaking at room temperature. The plates are centrifuged at 1500 rpm for 10 min and the radioactivity is measured using a Top-counter. The results are analyzed by non-linear regression and the $IC_{50}$ value is determined. RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by $10^{-8}$ M RAMHA is measured as a decrease in radioactivity signal. The $IC_{50}$ value determined for an antagonist is the ability of this compound to inhibit the effect of $10^{-8}$M RAMHA by 50%. In the agonist test, the ability of increasing amounts of test compound is measured as an increase in radioactivity signal. The $EC_{50}$ value determined for an agonist is the ability of this compound to increase the signal by 50% of the maximal signal that is obtained by $10^{-5}$ M RAMHA.

Preferably, the antagonists and agonists according to the invention have an $IC_{50}/EC_{50}$ value (as determined by one or more of the assays described above) of less than 10 µM, more preferably less than 1 µM, and still more preferably less than 500 nM, such as less than 100 nM.

The Open Cage Schedule-Fed Rat Model

The ability of the present compounds to reduce weight is determined using the in vivo open cage Schedule-fed rat model.

Sprague-Dawley (SD) male rats of an age of about 1½ to 2 months and a weight of about 200-250 g are purchased from Møllegård Breeding and Research Centre A/S (Denmark). On arrival they are allowed some days of acclimatisation before being placed in individual open plastic cages. They are habituated to the presence of food (Altromin pelleted rat chow) in their home cage for only 7 hours each day (from 07.30 to 14.30, seven days a week). Water is present ad libitum. Once the consumption of food has stabilised after 7 to 9 days, the animals are ready for use.

Each animal is used only once to avoid carry-over effects between treatments. During the test sessions, the test compound is administered intraperitoneally or orally 30 min before the start of the sessions. One group of animals is administered the test compound at different doses, and a control group of animals receives vehicle. Food and water intake are monitored at 1, 2 and 3 hours post administration.

Any side effects (manifested as barrel-rolling, bushy fur etc.) may rapidly be detected, since the animals are kept in transparent plastic cages to enable continuous monitoring.
Pharmacological Results:

|  | Functional assay II Human H3 GTPγS Ki [nM] | Open cage schedule-fed rat model, dose 15 mg/kg p.o., food intake at 3 h [% of vehicle] |
| --- | --- | --- |
| Example 17 | 1.8 | 81.2 |
| Example 27 | 0.9 | 82.9 |

What is claimed is:

1. A method of treating obesity comprising administering to a human subject a compound selected from the group consisting of:
[2-(4-isopropylpiperazin-1-yl)benzothiazol-6-yl]piperidin-1-ylmethanone,
2-(4-isopropylpiperazin-1-yl)benzothiazole-6-carboxylic acid dimethylamide,
[2-(4-isopropylpiperazin-1-yl)benzothiazol-6-yl]morpholin-4-ylmethanone,
2-(4-isopropylpiperazin-1-yl)-6-piperidin-1-ylmethyl-benzothiazole,
2-(4-isopropylpiperazin-1-yl)-6-(morpholin-4-ylmethyl)benzothiazole,
[2-(4-isopropylpiperazin-1-yl)benzothiazol-6-ylmethyl]dimethylamine,
[2-(4-cyclopropylpiperazin-1-yl)benzothiazol-6-ylmethyl]dimethylamine,
2-(4-cyclopropylpiperazin-1-yl)-6-(pyrrolidin-1-ylmethyl)benzothiazole,
2-(4-cyclopropylpiperazin-1-yl)-6-(morpholin-4-ylmethyl)benzothiazole,
2-(4-cyclopropylpiperazin-1-yl)-6-(piperidin-1-ylmethyl)benzothiazole,
cyclopropyl-[2-(4-cyclopropylpiperazin-1-yl)benzothiazol-6-ylmethyl]amine,
2-(4-isopropylpiperazin-1-yl)-5-(pyrrolidin-1-ylmethyl)benzothiazole,
[2-(4-isopropylpiperazin-1-yl)benzothiazol-5-ylmethyl]dimethylamine, and
[2-(4-isopropylpiperazin-1-yl)benzothiazol-5-yl]pyrrolidin-1-ylmethanone;
or a pharmaceutically acceptable salt thereof.

2. The method of claim 1, wherein the compound is 2-(4-cyclopropylpiperazin-1-yl)-6-(pyrrolidin-1-ylmethyl)benzothiazole or a pharmaceutically acceptable salt thereof.

3. The method of claim 1, wherein the compound is cyclopropyl-[2-(4-cyclopropylpiperazin-1-yl)benzothiazol-6-ylmethyl]amine or a pharmaceutically acceptable salt thereof.

4. The method of claim 1, wherein the compound is 2-(4-isopropylpiperazin-1-yl)-5-(pyrrolidin-1-ylmethyl)benzothiazole or a pharmaceutically acceptable salt thereof.

5. A method of reducing weight comprising administering to a human subject a compound selected from the group consisting of
[2-(4-isopropylpiperazin-1-yl)benzothiazol-6-yl]piperidin-1-ylmethanone,
2-(4-isopropylpiperazin-1-yl)benzothiazole-6-carboxylic acid dimethylamide,
[2-(4-isopropylpiperazin-1-yl)benzothiazol-6-yl]morpholin-4-ylmethanone,
2-(4-isopropylpiperazin-1-yl)-6-piperidin-1-ylmethyl-benzothiazole,
2-(4-isopropylpiperazin-1-yl)-6-(morpholin-4-ylmethyl)benzothiazole,
[2-(4-isopropylpiperazin-1-yl)benzothiazol-6-ylmethyl]dimethylamine,
[2-(4-cyclopropylpiperazin-1-yl)benzothiazol-6-ylmethyl]dimethylamine,
2-(4-cyclopropylpiperazin-1-yl)-6-(pyrrolidin-1-ylmethyl)benzothiazole,
2-(4-cyclopropylpiperazin-1-yl)-6-(morpholin-4-ylmethyl)benzothiazole,
2-(4-cyclopropylpiperazin-1-yl)-6-(piperidin-1-ylmethyl)benzothiazole,
cyclopropyl-[2-(4-cyclopropylpiperazin-1-yl)benzothiazol-6-ylmethyl]amine,
2-(4-isopropylpiperazin-1-yl)-5-(pyrrolidin-1-ylmethyl)benzothiazole,
[2-(4-isopropylpiperazin-1-yl)benzothiazol-5-ylmethyl]dimethylamine, and
[2-(4-isopropylpiperazin-1-yl)benzothiazol-5-yl]pyrrolidin-1-ylmethanone;
or a pharmaceutically acceptable salt thereof.

6. The method of claim 5, wherein the compound is 2-(4-cyclopropylpiperazin-1-yl)-6-(pyrrolidin-1-ylmethyl)benzothiazole or a pharmaceutically acceptable salt thereof.

7. The method of claim 5, wherein the compound is cyclopropyl-[2-(4-cyclopropylpiperazin-1-yl)benzothiazol-6-ylmethyl]amine or a pharmaceutically acceptable salt thereof.

8. The method of claim 5, wherein the compound is 2-(4-isopropylpiperazin-1-yl)-5-(pyrrolidin-1-ylmethyl)benzothiazole or a pharmaceutically acceptable salt thereof.

9. A method of suppressing appetite or inducing satiety comprising administering to a human subject a compound selected from the group consisting of:
[2-(4-isopropylpiperazin-1-yl)benzothiazol-6-yl]piperidin-1-ylmethanone,
2-(4-isopropylpiperazin-1-yl)benzothiazole-6-carboxylic acid dimethylamide,
[2-(4-isopropylpiperazin-1-yl)benzothiazol-6-yl]morpholin-4-ylmethanone,
2-(4-isopropylpiperazin-1-yl)-6-piperidin-1-ylmethyl-benzothiazole,
2-(4-isopropylpiperazin-1-yl)-6-(morpholin-4-ylmethyl)benzothiazole,
[2-(4-isopropylpiperazin-1-yl)benzothiazol-6-ylmethyl]dimethylamine,
[2-(4-cyclopropylpiperazin-1-yl)benzothiazol-6-ylmethyl]dimethylamine,
2-(4-cyclopropylpiperazin-1-yl)-6-(pyrrolidin-1-ylmethyl)benzothiazole, 2-(4-cyclopropylpiperazin-1-yl)-6-(morpholin-4-ylmethyl)benzothiazole,
2-(4-cyclopropylpiperazin-1-yl)-6-(piperidin-1-ylmethyl)benzothiazole,
cyclopropyl-[2-(4-cyclopropylpiperazin-1-yl)benzothiazol-6-ylmethyl]amine,
2-(4-isopropylpiperazin-1-yl)-5-(pyrrolidin-1-ylmethyl)benzothiazole,
[2-(4-isopropylpiperazin-1-yl)benzothiazol-5-ylmethyl]dimethylamine, and
[2-(4-isopropylpiperazin-1-yl)benzothiazol-5-yl]pyrrolidin-1-ylmethanone;

or a pharmaceutically acceptable salt thereof.

10. The method of claim 9, wherein the compound is 2-(4-cyclopropylpiperazin-1-yl)-6-(pyrrolidin-1-ylmethyl)benzothiazole or a pharmaceutically acceptable salt thereof.

11. The method of claim 9, wherein the compound is cyclopropyl-[2-(4-cyclopropylpiperazin-1-yl)benzothiazol-6-ylmethyl]amine or a pharmaceutically acceptable salt thereof.

12. The method of claim 9, wherein the compound is 2-(4-isopropylpiperazin-1-yl)-5-(pyrrolidin-1-ylmethyl)benzothiazole or a pharmaceutically acceptable salt thereof.

\* \* \* \* \*

UNITED STATES PATENT AND TRADEMARK OFFICE
CERTIFICATE OF CORRECTION

PATENT NO. : 8,772,285 B2  
APPLICATION NO. : 13/660045  
DATED : July 8, 2014  
INVENTOR(S) : Florencio Zaragoza Dorwald et al.

Page 1 of 1

It is certified that error appears in the above-identified patent and that said Letters Patent is hereby corrected as shown below:

On the title page, under Related U.S. Application Data, item (66), delete "Substitute for application No. PCT/EP2007/052751, filed" and insert therefor --filed as application No. PCT/EP2007/052751--

Signed and Sealed this
Twenty-third Day of September, 2014

Michelle K. Lee
*Deputy Director of the United States Patent and Trademark Office*